US012611115B2

(12) United States Patent
Sarkar et al.

(10) Patent No.: US 12,611,115 B2
(45) Date of Patent: Apr. 28, 2026

(54) DETERMINING LIKELIHOOD OF AN ADVERSE HEALTH EVENT BASED ON VARIOUS PHYSIOLOGICAL DIAGNOSTIC STATES

(71) Applicant: Medtronic, Inc., Minneapolis, MN (US)

(72) Inventors: Shantanu Sarkar, Roseville, MN (US); Jodi L. Redemske, Maple Grove, MN (US); Val D. Eisele, III, Little Canada, MN (US); Eduardo N. Warman, Maple Grove, MN (US); John E. Burnes, Blaine, MN (US); Jerry D. Reiland, Coon Rapids, MN (US); Brian B. Lee, Golden Valley, MN (US); Todd M. Zielinski, Ham Lake, MN (US); Matthew T Reinke, Roseville, MN (US)

(73) Assignee: Medtronic, Inc., Minneapolis, MN (US)

( * ) Notice: Subject to any disclaimer, the term of this patent is extended or adjusted under 35 U.S.C. 154(b) by 75 days.

(21) Appl. No.: 17/021,521

(22) Filed: Sep. 15, 2020

(65) Prior Publication Data

US 2021/0093254 A1      Apr. 1, 2021

Related U.S. Application Data

(60) Provisional application No. 62/906,991, filed on Sep. 27, 2019.

(51) Int. Cl.
*A61B 5/00*          (2006.01)
*A61B 5/0205*     (2006.01)
(Continued)

(52) U.S. Cl.
CPC ............ *A61B 5/053* (2013.01); *A61B 5/0205* (2013.01); *A61B 5/0538* (2013.01);
(Continued)

(58) Field of Classification Search
CPC ... A61B 5/0205; A61B 5/0538; A61B 5/7264; A61B 5/7275; G06K 9/6296
See application file for complete search history.

(56) References Cited

U.S. PATENT DOCUMENTS 3,724,455 A      4/1973   Unger
3,872,252 A      3/1975   Malchman et al.
(Continued)

FOREIGN PATENT DOCUMENTS

CN            1353619 A      6/2002
CN        102946800 A      2/2013
(Continued)

OTHER PUBLICATIONS

Murphy, Kevin. A Brief Introduction to Graphical Models and Bayesian Networks [online]. 1998 Retrieved from the Internet:< URL: https://www.cs.ubc.ca/~murphyk/Bayes/bnintro.html (Year: 1998).*
(Continued)

*Primary Examiner* — Allen Porter
*Assistant Examiner* — Moussa Haddad
(74) *Attorney, Agent, or Firm* — Shumaker & Sieffert, P.A.

(57)          ABSTRACT

Techniques for determining a likeliness that a patient may incur an adverse health event are described. An example technique may include utilizing a probability model that uses as evidence nodes various diagnostic states of physiological parameters, which may include one or more subcutaneous impedance parameters. The probability model may include a Bayesian Network that determines a posterior
(Continued)

probability of the adverse health event occurring within a predetermined period of time.

25 Claims, 11 Drawing Sheets

(51) Int. Cl.

| | |
|---|---|
| *A61B 5/053* | (2021.01) |
| *A61B 5/0538* | (2021.01) |
| *A61B 5/11* | (2006.01) |
| *G06F 18/20* | (2023.01) |

(52) U.S. Cl.

CPC ............ *A61B 5/1118* (2013.01); *A61B 5/686* (2013.01); *A61B 5/7264* (2013.01); *A61B 5/7275* (2013.01); *G06F 18/29* (2023.01)

(56) References Cited

U.S. PATENT DOCUMENTS

| | | | |
|---|---|---|---|
| 4,108,166 | A | 8/1978 | Schmid |
| 4,374,382 | A | 2/1983 | Markowitz |
| 4,823,797 | A | 4/1989 | Heinze et al. |
| 5,107,833 | A | 4/1992 | Barsness |
| 5,117,824 | A | 6/1992 | Keimel et al. |
| 5,168,871 | A | 12/1992 | Grevious |
| 5,271,395 | A | 12/1993 | Wahlstrand et al. |
| 5,292,343 | A | 3/1994 | Blanchette et al. |
| 5,314,450 | A | 5/1994 | Thompson |
| 5,324,315 | A | 6/1994 | Grevious |
| 5,354,319 | A | 10/1994 | Wybory et al. |
| 5,383,909 | A | 1/1995 | Keimel |
| 5,545,186 | A | 8/1996 | Olson et al. |
| 5,755,736 | A | 5/1998 | Gillberg et al. |
| 5,836,975 | A | 11/1998 | DeGroot |
| 5,876,353 | A | 3/1999 | Riff |
| 5,957,861 | A | 9/1999 | Combs et al. |
| 6,045,513 | A | 4/2000 | Stone et al. |
| 6,102,874 | A | 8/2000 | Stone et al. |
| 6,104,949 | A | 8/2000 | Crick et al. |
| 6,148,233 | A | 11/2000 | Owen et al. |
| 6,154,674 | A | 11/2000 | Meier |
| 6,221,011 | B1 | 4/2001 | Bardy |
| 6,263,243 | B1 | 7/2001 | Lang |
| 6,277,072 | B1 | 8/2001 | Bardy |
| 6,280,380 | B1 | 8/2001 | Bardy |
| 6,280,409 | B1 | 8/2001 | Stone et al. |
| 6,336,903 | B1 | 1/2002 | Bardy |
| 6,405,085 | B1 | 6/2002 | Graupner et al. |
| 6,449,509 | B1 | 9/2002 | Park et al. |
| 6,459,929 | B1 | 10/2002 | Hopper et al. |
| 6,463,326 | B1 | 10/2002 | Hartley et al. |
| 6,473,640 | B1 | 10/2002 | Erlebacher |
| 6,480,733 | B1 | 11/2002 | Turcott |
| 6,512,949 | B1 | 1/2003 | Combs et al. |
| 6,572,557 | B2 | 6/2003 | Tchou et al. |
| 6,595,927 | B2 | 7/2003 | Pitts-Crick et al. |
| 6,599,250 | B2 | 7/2003 | Webb et al. |
| 6,671,549 | B2 | 12/2003 | Van Dam et al. |
| 6,709,390 | B1 | 3/2004 | Marie Pop |
| 6,821,249 | B2 | 11/2004 | Casscells, III et al. |
| 6,866,629 | B2 | 3/2005 | Bardy |
| 6,895,275 | B2 | 5/2005 | Markowitz et al. |
| 6,907,288 | B2 | 6/2005 | Daum |
| 6,931,272 | B2 | 8/2005 | Burnes |
| 6,941,168 | B2 | 9/2005 | Girouard |
| 6,945,934 | B2 | 9/2005 | Bardy |
| 6,960,167 | B2 | 11/2005 | Bardy |
| 7,020,521 | B1 | 3/2006 | Brewer et al. |
| 7,127,290 | B2 | 10/2006 | Girouard et al. |
| 7,177,681 | B2 | 2/2007 | Zhu |
| 7,184,821 | B2 | 2/2007 | Belalcazar et al. |
| 7,248,916 | B2 | 7/2007 | Bardy |
| 7,248,919 | B2 | 7/2007 | Carlson et al. |
| 7,272,442 | B2 | 9/2007 | Freeberg |
| 7,308,309 | B1 | 12/2007 | Koh |
| 7,310,551 | B1 | 12/2007 | Koh et al. |
| 7,313,434 | B2 | 12/2007 | Belalcazar et al. |
| 7,336,996 | B2 | 2/2008 | Hartley et al. |
| 7,340,296 | B2 | 3/2008 | Stahmann et al. |
| 7,387,610 | B2 | 6/2008 | Stahmann et al. |
| 7,389,143 | B2 | 6/2008 | Hopper et al. |
| 7,424,321 | B2 | 9/2008 | Wariar et al. |
| 7,468,040 | B2 | 12/2008 | Hartley et al. |
| 7,469,697 | B2 | 12/2008 | Lee et al. |
| 7,499,748 | B2 | 3/2009 | Moffitt et al. |
| 7,499,750 | B2 | 3/2009 | Haefner et al. |
| 7,510,531 | B2 | 3/2009 | Lee et al. |
| 7,532,934 | B2 | 5/2009 | Lee et al. |
| 7,542,800 | B2 | 6/2009 | Libbus et al. |
| 7,561,923 | B2 | 7/2009 | Libbus et al. |
| 7,572,225 | B2 | 8/2009 | Stahmann et al. |
| 7,575,553 | B2 | 8/2009 | Stahmann et al. |
| 7,580,745 | B2 | 8/2009 | Pastore et al. |
| 7,587,238 | B2 | 9/2009 | Moffitt et al. |
| 7,606,622 | B2 | 10/2009 | Reeve |
| 7,617,003 | B2 | 11/2009 | Caparso et al. |
| 7,629,889 | B2 | 12/2009 | Sachanandani et al. |
| 7,643,877 | B2 | 1/2010 | Dujmovic, Jr. et al. |
| 7,657,312 | B2 | 2/2010 | Pastore et al. |
| 7,659,899 | B2 | 2/2010 | Paltashev et al. |
| 7,660,628 | B2 | 2/2010 | Libbus et al. |
| 7,672,724 | B2 | 3/2010 | Pastore et al. |
| 7,720,541 | B2 | 5/2010 | Stahmann et al. |
| 7,734,341 | B2 | 6/2010 | Shuros |
| 7,742,815 | B2 | 6/2010 | Salo et al. |
| 7,757,690 | B2 | 7/2010 | Stahmann et al. |
| 7,769,446 | B2 | 8/2010 | Moffitt et al. |
| 7,774,055 | B1 | 8/2010 | Min |
| 7,798,973 | B2 | 9/2010 | Stahmann |
| 7,801,591 | B1 | 9/2010 | Shusterman |
| 7,813,808 | B1 | 10/2010 | Doron et al. |
| 7,887,493 | B2 | 2/2011 | Stahmann et al. |
| 7,894,906 | B2 | 2/2011 | Shuros |
| 7,955,268 | B2 | 6/2011 | Huelskamp |
| 7,979,141 | B2 | 7/2011 | Caparso et al. |
| 7,986,994 | B2 | 7/2011 | Stadler et al. |
| 7,993,279 | B2 | 8/2011 | Hartley et al. |
| 8,024,050 | B2 | 9/2011 | Libbus et al. |
| 8,031,076 | B2 | 10/2011 | Sachanandani et al. |
| 8,032,215 | B2 | 10/2011 | Libbus et al. |
| 8,052,611 | B2 | 11/2011 | Wariar et al. |
| 8,062,227 | B2 | 11/2011 | Cho et al. |
| 8,096,954 | B2 | 1/2012 | Stahmann et al. |
| 8,103,341 | B2 | 1/2012 | Libbus et al. |
| 8,104,470 | B2 | 1/2012 | Lee et al. |
| 8,126,560 | B2 | 2/2012 | Scheiner et al. |
| 8,131,362 | B2 | 3/2012 | Moffitt et al. |
| 8,145,304 | B2 | 3/2012 | Moffitt et al. |
| 8,175,705 | B2 | 5/2012 | Libbus |
| 8,202,224 | B2 | 6/2012 | Gutfinger et al. |
| 8,209,033 | B2 | 6/2012 | Zhang et al. |
| 8,221,325 | B2 | 7/2012 | Stahmann et al. |
| 8,221,327 | B2 | 7/2012 | Lee et al. |
| 8,223,023 | B2 | 7/2012 | Sachanandani et al. |
| 8,251,061 | B2 | 8/2012 | Lee et al. |
| 8,255,046 | B2 | 8/2012 | Sarkar et al. |
| 8,303,513 | B2 | 11/2012 | Wariar et al. |
| 8,321,022 | B2 | 11/2012 | Stahmann et al. |
| 8,323,204 | B2 | 12/2012 | Stahmann et al. |
| 8,364,263 | B2 | 1/2013 | Patangay et al. |
| 8,369,943 | B2 | 2/2013 | Shuros et al. |
| 8,369,960 | B2 | 2/2013 | Tran et al. |
| 8,386,045 | B2 | 2/2013 | Zhao et al. |
| 8,401,672 | B2 | 3/2013 | Libbus et al. |
| 8,406,876 | B2 | 3/2013 | McCabe et al. |
| 8,414,497 | B2 | 4/2013 | Stahmann |
| 8,452,398 | B2 | 5/2013 | Libbus et al. |
| 8,457,734 | B2 | 6/2013 | Libbus et al. |
| 8,478,397 | B2 | 7/2013 | Libbus et al. |
| 8,480,581 | B2 | 7/2013 | Zhang et al. |
| 8,515,535 | B2 | 8/2013 | Hopper et al. |
| 8,522,779 | B2 | 9/2013 | Lee et al. |

(56) References Cited

U.S. PATENT DOCUMENTS

| | | | |
|---|---|---|---|
| 8,527,042 B2 | 9/2013 | Libbus et al. | |
| 8,548,585 B2 | 10/2013 | Ternes et al. | |
| 8,571,655 B2 | 10/2013 | Pastore et al. | |
| 8,591,423 B2 | 11/2013 | Doron | |
| 8,606,356 B2 | 12/2013 | Lee et al. | |
| 8,612,000 B2 | 12/2013 | Stahmann et al. | |
| 8,620,426 B2 | 12/2013 | Moffitt et al. | |
| 8,632,470 B2 | 1/2014 | Stahmann et al. | |
| 8,634,930 B2 | 1/2014 | Dalal et al. | |
| 8,682,430 B2 | 3/2014 | Libbus et al. | |
| 8,708,924 B2 | 4/2014 | Wariar et al. | |
| 8,725,260 B2 | 5/2014 | Shuros et al. | |
| 8,738,119 B2 | 5/2014 | Zhang et al. | |
| 8,744,565 B2 | 6/2014 | Zielinski et al. | |
| 8,750,982 B2 | 6/2014 | Thakur et al. | |
| 8,750,992 B2 | 6/2014 | Hopper et al. | |
| 8,750,998 B1 | 6/2014 | Ghosh et al. | |
| 8,755,892 B2 | 6/2014 | Amurthur et al. | |
| 8,768,718 B2 | 7/2014 | Cazares et al. | |
| 8,777,850 B2 | 7/2014 | Cho et al. | |
| 8,805,503 B2 | 8/2014 | Pastore et al. | |
| 8,897,881 B2 | 11/2014 | Libbus et al. | |
| 8,929,990 B2 | 1/2015 | Moffitt et al. | |
| 8,938,286 B2 | 1/2015 | Dumont et al. | |
| 8,954,146 B2 | 2/2015 | Hopper et al. | |
| 8,972,008 B2 | 3/2015 | Patangay et al. | |
| 9,002,448 B2 | 4/2015 | Libbus et al. | |
| 9,014,819 B2 | 4/2015 | Lee et al. | |
| 9,022,930 B2 | 5/2015 | Sachanandani et al. | |
| 9,089,691 B2 | 7/2015 | Libbus et al. | |
| 9,138,151 B2 | 9/2015 | Wariar et al. | |
| 9,147,041 B2 | 9/2015 | Amarasingham et al. | |
| 9,149,641 B2 | 10/2015 | Stahmann et al. | |
| 9,161,698 B2 | 10/2015 | Zhang et al. | |
| 9,173,615 B2 | 11/2015 | Katra et al. | |
| 9,186,522 B2 | 11/2015 | Ternes et al. | |
| 9,211,412 B2 | 12/2015 | McCabe et al. | |
| 9,216,289 B2 | 12/2015 | Libbus et al. | |
| 9,232,897 B2 | 1/2016 | Thakur et al. | |
| 9,259,568 B2 | 2/2016 | Zhao et al. | |
| 9,259,575 B2 | 2/2016 | Zhao et al. | |
| 9,277,885 B2 | 3/2016 | Hopper et al. | |
| 9,314,637 B2 | 4/2016 | Libbus | |
| 9,339,652 B2 | 5/2016 | Moffitt et al. | |
| 9,345,414 B1* | 5/2016 | Bardy | A61B 5/0006 |
| 9,403,007 B2 | 8/2016 | Mokelke et al. | |
| 9,610,445 B2 | 4/2017 | Thakur et al. | |
| 9,615,744 B2 | 4/2017 | Denison et al. | |
| 9,622,664 B2 | 4/2017 | An et al. | |
| 9,622,665 B2 | 4/2017 | Zhang et al. | |
| 9,629,548 B2 | 4/2017 | Sachanandani et al. | |
| 9,630,014 B2 | 4/2017 | Averina et al. | |
| 9,649,496 B2 | 5/2017 | Thakur et al. | |
| 9,662,073 B2 | 5/2017 | Zhang et al. | |
| 9,700,726 B2 | 7/2017 | Stahmann et al. | |
| 9,713,701 B2 | 7/2017 | Sarkar et al. | |
| 9,730,592 B2 | 8/2017 | Wariar et al. | |
| 9,814,424 B2 | 11/2017 | Zhang et al. | |
| 9,814,429 B2 | 11/2017 | Lee et al. | |
| 9,872,987 B2 | 1/2018 | Libbus et al. | |
| 9,962,548 B2 | 5/2018 | McCabe et al. | |
| 9,968,266 B2 | 5/2018 | An et al. | |
| 10,058,708 B2 | 8/2018 | Zhang et al. | |
| 10,092,186 B2 | 10/2018 | Hatlestad et al. | |
| 10,130,817 B2 | 11/2018 | Stolen et al. | |
| 10,143,385 B2 | 12/2018 | Sweeney et al. | |
| 10,182,768 B2 | 1/2019 | Zhang et al. | |
| 10,188,353 B2 | 1/2019 | Stolen et al. | |
| 10,226,634 B2 | 3/2019 | Averina et al. | |
| 10,251,563 B2 | 4/2019 | Sweeney et al. | |
| 10,271,797 B2 | 4/2019 | Zhang et al. | |
| 10,350,418 B2 | 7/2019 | An et al. | |
| 10,368,774 B2 | 8/2019 | Sharma et al. | |
| 10,441,179 B2 | 10/2019 | Wariar et al. | |
| 10,456,049 B2 | 10/2019 | Zhang et al. | |
| 10,502,747 B2 | 12/2019 | Stolen et al. | |
| 10,506,987 B2 | 12/2019 | An et al. | |
| 10,596,381 B2 | 3/2020 | Averina et al. | |
| 10,702,213 B2 | 7/2020 | Sharma et al. | |
| 10,750,996 B2 | 8/2020 | Wariar | |
| 10,893,824 B2 | 1/2021 | An et al. | |
| 10,952,681 B2 | 3/2021 | Sharma et al. | |
| 11,141,070 B2 | 10/2021 | Matsumoto | |
| 11,568,993 B2 | 1/2023 | Zaphrir et al. | |
| 11,998,303 B2 | 6/2024 | Sarkar et al. | |
| 2001/0011153 A1 | 8/2001 | Bardy | |
| 2001/0021801 A1 | 9/2001 | Bardy | |
| 2001/0039504 A1 | 11/2001 | Lindberg et al. | |
| 2002/0026104 A1 | 2/2002 | Bardy | |
| 2002/0035380 A1 | 3/2002 | Rissmann et al. | |
| 2003/0028221 A1 | 2/2003 | Zhu et al. | |
| 2003/0055461 A1 | 3/2003 | Girouard et al. | |
| 2003/0125611 A1 | 7/2003 | Bardy | |
| 2003/0149367 A1 | 8/2003 | Kroll et al. | |
| 2003/0216654 A1 | 11/2003 | Xu et al. | |
| 2003/0220580 A1 | 11/2003 | Alt | |
| 2004/0102712 A1 | 5/2004 | Belalcazar et al. | |
| 2004/0122484 A1 | 6/2004 | Hatlestad et al. | |
| 2004/0122787 A1 | 6/2004 | Avinash et al. | |
| 2004/0172080 A1 | 9/2004 | Stadler et al. | |
| 2005/0124900 A1 | 6/2005 | Stadler et al. | |
| 2005/0124908 A1 | 6/2005 | Belalcazar et al. | |
| 2006/0010090 A1 | 1/2006 | Brockway et al. | |
| 2006/0020007 A1 | 1/2006 | Berlin | |
| 2006/0020295 A1 | 1/2006 | Brockway et al. | |
| 2006/0200007 A1 | 9/2006 | Brockway et al. | |
| 2006/0293609 A1 | 12/2006 | Stahmann et al. | |
| 2007/0142732 A1 | 6/2007 | Brockway et al. | |
| 2007/0156061 A1 | 7/2007 | Hess | |
| 2007/0239043 A1 | 10/2007 | Patel et al. | |
| 2007/0260285 A1 | 11/2007 | Libbus et al. | |
| 2008/0004664 A1 | 1/2008 | Hopper et al. | |
| 2008/0024293 A1 | 1/2008 | Stylos | |
| 2008/0027349 A1 | 1/2008 | Stylos | |
| 2008/0103399 A1 | 5/2008 | Patangay et al. | |
| 2008/0157980 A1 | 7/2008 | Sachanandani et al. | |
| 2008/0161657 A1 | 7/2008 | Kessels et al. | |
| 2008/0228090 A1 | 9/2008 | Wariar et al. | |
| 2008/0275349 A1 | 11/2008 | Halperin et al. | |
| 2009/0030292 A1 | 1/2009 | Bartnik et al. | |
| 2009/0043355 A1 | 2/2009 | Cazares et al. | |
| 2009/0281399 A1 | 11/2009 | Keel et al. | |
| 2010/0030086 A1 | 2/2010 | Zielinski et al. | |
| 2010/0030292 A1 | 2/2010 | Sarkar et al. | |
| 2010/0030293 A1 | 2/2010 | Sarkar et al. | |
| 2010/0113888 A1 | 5/2010 | Cho et al. | |
| 2010/0114241 A1 | 5/2010 | Donofrio et al. | |
| 2010/0152802 A1 | 6/2010 | Min | |
| 2010/0198097 A1 | 8/2010 | Sowelam | |
| 2011/0009760 A1 | 1/2011 | Zhang et al. | |
| 2012/0109243 A1 | 5/2012 | Hettrick et al. | |
| 2012/0157856 A1 | 6/2012 | An et al. | |
| 2012/0221069 A1 | 8/2012 | Rosenberg et al. | |
| 2012/0253207 A1 | 10/2012 | Sarkar et al. | |
| 2013/0116578 A1 | 5/2013 | An et al. | |
| 2013/0116583 A1 | 5/2013 | Min | |
| 2013/0172691 A1 | 7/2013 | Tran | |
| 2013/0197381 A1 | 8/2013 | Charlton et al. | |
| 2014/0276928 A1 | 9/2014 | Vanderpool et al. | |
| 2014/0330172 A1 | 11/2014 | Jovanov et al. | |
| 2014/0343439 A1 | 11/2014 | Sweeney et al. | |
| 2015/0126822 A1 | 5/2015 | Chavan et al. | |
| 2015/0157221 A1 | 6/2015 | An et al. | |
| 2015/0157273 A1* | 6/2015 | An | A61B 5/7275 |
| | | | 600/595 |
| 2015/0327776 A1* | 11/2015 | Zhang | G16H 50/20 |
| | | | 600/300 |
| 2016/0038093 A1 | 2/2016 | Sharma et al. | |
| 2016/0157769 A1 | 6/2016 | Min et al. | |
| 2016/0206250 A1 | 7/2016 | Sharma et al. | |
| 2016/0361026 A1 | 12/2016 | Sarkar et al. | |
| 2017/0021489 A1 | 1/2017 | Bylund et al. | |
| 2017/0181677 A1 | 6/2017 | Varsavsky et al. | |
| 2017/0238812 A1 | 8/2017 | Atlas | |

(56) References Cited

U.S. PATENT DOCUMENTS

| | | | |
|---|---|---|---|
| 2017/0245794 A1 | 8/2017 | Sharma et al. | |
| 2017/0265782 A1 | 9/2017 | Vollmer | |
| 2017/0303797 A1 | 10/2017 | Wariar et al. | |
| 2017/0354365 A1 | 12/2017 | Zhou | |
| 2017/0360320 A1 | 12/2017 | Sarkar et al. | |
| 2018/0021570 A1* | 1/2018 | An | A61N 1/362 |
| | | | 607/123 |
| 2018/0035898 A1 | 2/2018 | Gunderson | |
| 2018/0126172 A1 | 5/2018 | Sarkar et al. | |
| 2018/0168463 A1 | 6/2018 | Morris et al. | |
| 2019/0006985 A1 | 1/2019 | Twisselman | |
| 2019/0069851 A1 | 3/2019 | Sharma et al. | |
| 2019/0083030 A1* | 3/2019 | Thakur | A61B 5/7275 |
| 2019/0125273 A1 | 5/2019 | Sharma et al. | |
| 2019/0183339 A1* | 6/2019 | Shah | A61B 5/7275 |
| 2019/0336077 A1* | 11/2019 | Kuhn | A61B 5/7282 |
| 2020/0022588 A1 | 1/2020 | Wariar et al. | |
| 2020/0030612 A1 | 1/2020 | Song et al. | |
| 2020/0054238 A1 | 2/2020 | Gopinathan et al. | |
| 2020/0129099 A1 | 4/2020 | Mi et al. | |
| 2020/0337563 A1 | 10/2020 | Andersen | |
| 2020/0383597 A1 | 12/2020 | Rajagopal et al. | |
| 2020/0383647 A1* | 12/2020 | Freeman | A61B 5/02055 |
| 2021/0020294 A1 | 1/2021 | Bharmi et al. | |
| 2021/0093220 A1 | 4/2021 | Sarkar et al. | |
| 2021/0093253 A1 | 4/2021 | Sarkar et al. | |
| 2021/0093254 A1 | 4/2021 | Sarkar et al. | |
| 2021/0204874 A1 | 7/2021 | Thakur et al. | |
| 2021/0345935 A1 | 11/2021 | Gill et al. | |
| 2022/0193419 A1 | 6/2022 | Sarkar et al. | |

FOREIGN PATENT DOCUMENTS

| | | | | |
|---|---|---|---|---|
| CN | 105792739 A | 7/2016 | | |
| CN | 105792741 A | 7/2016 | | |
| CN | 105873504 A | 8/2016 | | |
| CN | 107921266 A | 4/2018 | | |
| CN | 108348745 A | 7/2018 | | |
| DE | 10148440 A1 | 4/2003 | | |
| EP | 1997427 A1 | 3/2008 | | |
| WO | 98033554 A1 | 8/1998 | | |
| WO | 200064336 A1 | 11/2000 | | |
| WO | 2001032260 A1 | 5/2001 | | |
| WO | 2004045406 A1 | 6/2004 | | |
| WO | 2005110051 A1 | 11/2005 | | |
| WO | 2005110051 A2 | 11/2005 | | |
| WO | 2006/070124 A1 | 7/2006 | | |
| WO | 2006081432 A1 | 8/2006 | | |
| WO | 2007079354 A2 | 7/2007 | | |
| WO | 2009063446 | 5/2009 | | |
| WO | 2010014066 A | 2/2010 | | |
| WO | 2010042855 A1 | 4/2010 | | |
| WO | 2011126823 A1 | 10/2011 | | |
| WO | 2013022760 A1 | 2/2013 | | |
| WO | 2013082126 A1 | 6/2013 | | |
| WO | 20150175207 A1 | 11/2015 | | |
| WO | WO-2015175207 A1 * | 11/2015 | | A61B 5/0205 |
| WO | 2016013684 A1 | 1/2016 | | |

OTHER PUBLICATIONS

Final Office Action from U.S. Appl. No. 16/119,329, dated Oct. 6, 2020, 8 pp.

Amendment in Response to Office Action mailed Oct. 6, 2020, from U.S. Appl. No. 16/119,329, filed Nov. 18, 2020, 8 pp.

Advisory Action from U.S. Appl. No. 16/119,329, dated Dec. 18, 2020, 3 pp.

Adamson et al., "Continuous Autonomic Assessment in Patients with Symptomatic Heart Failure . . . " Circulation Journal of American Heart Association, pp. 2389-2394. 110: 16, Lippincott Williams & Wilkins, Baltimore MD, Jun. 30, 2004.

Lusignan, et al. "Compliance and Effectiveness of 1 Year's Home Telemonitoring, The Report of a Pilot Study . . . " European Journal of Heart Failure, 3:723-730, Dec. 2001.

Baer, et al. "Electronic Home Monitoring of Congestive Heart Failure Patients: Design and Feasibility", Congestive Heart Failure, 5:105-113, May-Jun. 1999.

Wuerz et al., "Effects of Prehospital Medications on Mortality and Length of Stay in Congestive Heart Failure", Annals of Emergency Medicine 21:6 pp. 669-674, Jun. 1992.

Berman et al. "Transthoracic Electrical Impedance as a Guide to Intravascular Overload", Archives Surgery, 102, pp. 61-64 Jan. 1971.

Cowie et al., "Development and validation of an integrated diagnostic algorithm derived from parameters monitored in implantable devices for identifying patients at risk for heart failure hospitalization in an ambulatory setting," European Heart Journal, vol. 34, Mar. 19, 2013, pp. 2472-2480.

U.S. Appl. No. 16/450,250, filed Jun. 24, 2019, by Sarkar et al.

Yu et al., "Intrathoracic Impedance Monitoring in Patients With Heart Failure," Circulation, vol. 112, No. 6, Aug. 9, 2005, pp. 841-848.

Adamson et al., "Wireless Pulmonary Artery Pressure Monitoring Guides Management to Reduce Decompensation in Heart Failure With Preserved Ejection Fraction," Circ Hear Fail, Nov. 2014, pp. 935-944.

Prosecution History from U.S. Appl. No. 13/391,376, dated Nov. 2, 2016 through Apr. 25, 2018, 117 pp.

Prosecution History from U.S. Appl. No. 16/119,329, dated Sep. 25, 2018 through Jun. 30, 2020, 29 pp.

Prosecution History from U.S. Appl. No. 15/963,448, dated Dec. 20, 2019 through Mar. 24, 2020, 23 pp.

U.S. Appl. No. 17/021,489, filed Sep. 15, 2020, by Sarkar et al.

U.S. Appl. No. 17/021,564, filed Sep. 15, 2020, by Sarkar et al.

PCT/US2020/052078, The International Search Report and Written Opinion, mailed Jan. 12, 2021, 9 pages.

Athanasiou M. et al., "A Bayesian Network Model for the Diagnosis of the Caring Procedure for Wheelchair Users With Spinal Injury" Computer Methods and Programs in Biomedicine, Elsevier, Amsterdam, NL vol. 95, No. 2, Aug. 1, 2009, pp. S44-S54.

Response to Office Action mailed Oct. 6, 2020, and Advisory Action mailed Dec. 18, 2020, from U.S. Appl. No. 16/119,329, filed Dec. 28, 2020, 3 pp.

Notice of Allowance from U.S. Appl. No. 16/119,329, mailed Jan. 25, 2020, 7 pp.

Gholamhosseini et al., "Smartphone-based blood pressure monitoring for falls risk assessment: techniques and technologies," Human Monitoring, Smart Health and Assisted Living: Techniques and Technologies, May 31, 2017, pp. 203-215.

International Search Report and Written Opinion of International Application No. PCT/US2020/058624, mailed Feb. 8, 2021, 12 pp.

Response to Office Action dated Nov. 25, 2022 from U.S. Appl. No. 17/208,666, filed Jan. 31, 2023, 13 pp.

Gardner et al., "HeartLogic Multisensor Algorithm Identifies Patients During Periods of Significantly Increased Risk of Heart Failure Events," Circulation: Heart Failure, vol. 11, No. 7, Jul. 2018, 10 pp.

Office Action from U.S. Appl. No. 17/208,666 dated Nov. 25, 2022, 20 pp.

Sarkar et al., "A Dynamic Risk Score to Identify Increased Risk for Heart Failure Decompensation", IEEE Transactions on Biomedical Engineering, vol. 60, No. 1, Jan. 2013, pp. 147-150.

Final Office Action from U.S. Appl. No. 17/208,666 dated May 8, 2023, 18 pp.

Advisory Action from U.S. Appl. No. 17/208,666 dated Aug. 1, 2023, 2 pp.

Response to Final Office Action dated May 8, 2023 from U.S. Appl. No. 17/208,666, filed Jul. 6, 2023, 13 pp.

Office Action from U.S. Appl. No. 17/208,666 dated Sep. 27, 2023, 7 pp.

Prutchi et al., "Design and Development of Medical Electronic Instrumentation: A Practical Perspective of the Design, Construction, and Test of Medical Devices", John Wiley & Sons, Jan. 28, 2005, pp. 400-401.

Response to Office Action dated Sep. 27, 2023 from U.S. Appl. No. 17/208,666, filed Dec. 12, 2023, 11 pp.

(56) References Cited

OTHER PUBLICATIONS

Notice of Allowance from U.S. Appl. No. 17/208,666 dated Mar. 5, 2024, 7 pp.

Office Action from U.S. Appl. No. 17/208,666 dated Jul. 19, 2024, 12 pp.

Response to Office Action dated Jul. 19, 2024 from U.S. Appl. No. 17/208,666, filed Oct. 1, 2024, 17 pp.

Final Office Action from U.S. Appl. No. 17/208,666 dated Nov. 21, 2024, 13 pp.

Appeal Brief from U.S. Appl. No. 17/208,666, filed Mar. 26, 2025, 39 pp.

Giraud et al., "Respiratory change in ECG-wave amplitude is a reliable parameter to estimate intravascular volume status", Journal of clinical monitoring and computing, Springer Science+Business Media, Nov. 2, 2012, pp. 107-111.

Lara et al., "Accurate monitoring of intravascular fluid volume A novel application of intrathoracic impedance measures for the guidance of volume reduction therapy", IJC Heart & Vasculature, vol. 8, Elsevier Ireland Ltd., May 15, 2015, pp. 47-51.

Maisel, "B-Type Natriuretic Peptide Levels: Diagnostic and Prognostic in Congestive Heart Failure What's Next?", American Heart Association, Inc., vol. 105, No. 20, May 21, 2002, pp. 2328-2331.

Montgomery et al., "Monitoring intracellular, interstitial, and intravascular volume changes during fluid management procedures", Medical & biological engineering & computing, Oct. 1, 2013, pp. 1167-1175.

Office Action from U.S. Appl. No. 17/690,723 dated Mar. 6, 2025, 14 pp.

Prosecution History from U.S. Appl. No. 13/391,376, dated Feb. 21, 2014 through Dec. 4, 2018, 120 pp.

Prosecution History from U.S. Appl. No. 15/850,024, dated May 14, 2019 through Apr. 18, 2022, 169 pp.

Thakur et al., "Haemodynamic monitoring of cardiac status using heart sounds from an implanted cardiac device", ESC heart failure, vol. 4, No. 4, Jul. 4, 2017, pp. 605-613.

Small, R.S., Changes in Intrathoracic Impedance are Associated With Subsequent Risk of Hospitalizations for Acute Decompensated Heart Failure: Clinical Utility of Implanted Device Monitoring Without a Patient Alert, Journal of Cardiac Failure, Aug. 2009, 15(6):475-81.

Office Action from counterpart Chinese Application No. 202080067362.6 dated Apr. 11, 2025, 15 pp. Translation Attached.

Response to Office Action dated Mar. 6, 2025 from U.S. Appl. No. 17/690,723, filed Jun. 5, 2025, 15 pp.

U.S. Appl. No. 19/215,665, filed May 22, 2025, by Sarkar et al.

Advisory Action from U.S. Appl. No. 17/690,723 dated Oct. 2, 2025, 3 pp.

Response to Final Office Action dated Jul. 30, 2025 from U.S. Appl. No. 17/690,723, filed Sep. 18, 2025, 15 pp.

Decision of Rejection from counterpart Chinese Application No. 202080067362.6 dated Aug. 19, 2025, 7 pp. Only Translation available.

El-Matouat et al., "From continuous to discrete variables for Bayesian network classifiers", Smc 2000 conference proceedings. 2000 ieee international conference on systems, man and cybernetics. cybernetics evolving to systems, humans, organizations, and their complex interactions, vol. 4, IEEE, Oct. 8, 2000, pp. 2800-2805.

Fernandez et al., "Bayesian networks and influence diagrams as valid decision support tools in systolic heart failure management", Computers in Cardiology, IEEE, Sep. 2004, 4 pp.

Office Action from U.S. Appl. No. 19/215,665 dated Jul. 18, 2025, 13 pp.

Roberts et al., "Bayesian Networks for Cardiovascular Monitoring", 2006 International Conference of the IEEE Engineering in Medicine and Biology Society, IEEE, Aug. 30, 2006, pp. 205-209.

Sheppard et al., "Not-So-Naive Bayesian Networks and Unique Identification in Developing Advanced Diagnostics", 2006 IEEE Aerospace Conference, IEEE, Mar. 2006, 14 pp.

Final Office Action from U.S. Appl. No. 17/690,723 dated Jul. 30, 2025, 9 pp.

Response to Office Action dated Jul. 18, 2025 from U.S. Appl. No. 19/215,665, filed Oct. 20, 2025, 17 pp.

Final Office Action from U.S. Appl. No. 19/215,665 dated Nov. 5, 2025, 18 pp.

Office Action from U.S. Appl. No. 17/690,723 dated Nov. 20, 2025, 9 pp.

Advisory Action from U.S. Appl. No. 19/215,665 dated Jan. 15, 2026, 7 pp.

Response to Final Office Action dated Nov. 5, 2025 from U.S. Appl. No. 19/215,665, filed Jan. 5, 2026, 21 pp.

* cited by examiner

502 — DETERMINE PHYSIOLOGICAL PARAMETER VALUES

504 — IDENTIFY DIAGNOSTIC STATE FOR EACH PHYSIOLOGICAL PARAMETER

506 — ACCESS PROBABILITY MODEL

508 — DETERMINE CONDITIONAL LIKELIHOOD AND PRIOR PROBABILITY DATA

510 — EXECUTE PROBABILITY MODEL

512 — DETERMINE PROBABILITY SCORE

514 — DETERMINE HEALTH RISK STATUS

2

EXTERNAL
DEVICE
12

4

10

1002    RECEIVE PROBABILITY SCORE OR RISK
        ASSESSMENT FOR PATIENT

1004    DETERMINE INSTRUCTIONS FOR MEDICAL
        INTERVENTION BASED ON PROBABILITY
        SCORE OR RISK ASSESSMENT OF PATIENT

1006    TRANSMIT INSTRUCTIONS FOR MEDICAL
        INTERVENTION TO USER INTERFACE

DETERMINING LIKELIHOOD OF AN ADVERSE HEALTH EVENT BASED ON VARIOUS PHYSIOLOGICAL DIAGNOSTIC STATES

This application claims the benefit of U.S. Provisional Application No. 62/906,991, entitled "DETERMINING LIKELIHOOD OF AN ADVERSE HEALTH EVENT BASED ON VARIOUS PHYSIOLOGICAL DIAGNOSTIC STATES," filed Sep. 27, 2019, the entire contents of which are hereby incorporated in their entirety as though set forth fully herein.

CROSS-REFERENCE TO RELATED APPLICATIONS

This patent disclosure hereby incorporates by reference in its entirety the following applications filed on even date hereof; namely, U.S. application Ser. No. 17/021,489, entitled "DETERMINING HEART CONDITION STATUSES USING SUBCUTANEOUS IMPEDANCE MEASUREMENTS,", corresponding to Ser. No. 62/906,973; and U.S. application Ser. No. 17/021,564, entitled "DETERMINING HEALTH CONDITION STATUSES USING SUBCUTANEOUS IMPEDANCE MEASUREMENTS,", corresponding to Ser. No. 62/906,979.

FIELD

The disclosure relates to medical devices and, more particularly, medical devices for detecting or monitoring heart conditions.

BACKGROUND

A variety of medical devices have been used or proposed for use to deliver a therapy to and/or monitor a physiological condition of patients. As examples, such medical devices may deliver therapy and/or monitor conditions associated with the heart, muscle, nerve, brain, stomach or other organs or tissue. Medical devices that deliver therapy include medical devices that deliver one or both of electrical stimulation or a therapeutic agent to the patient. Some medical devices have been used or proposed for use to monitor heart failure or to detect heart failure events.

Heart failure (HF) is the most common cardiovascular disease that causes significant economic burden, morbidity, and mortality. In the United States alone, roughly 5 million people have HF, accounting for a significant number of hospitalizations. HF may result in cardiac chamber dilation, increased pulmonary blood volume, and fluid retention in the lungs. Generally, the first indication that a physician has of HF in a patient is not until it becomes a physical manifestation with swelling or breathing difficulties so overwhelming as to be noticed by the patient who then proceeds to be examined by a physician. This is undesirable since hospitalization at such a time would likely be required for a cardiac heart failure patient to remove excess fluid and relieve symptoms.

SUMMARY

This disclosure describes techniques for providing an early warning for various health or heart conditions (e.g., heart failure decompensation, worsening heart failure, or other cardiovascular-related conditions, such as edema). The disclosed technology uses prediction and probability modeling to determine a probability or likeliness indicator that an adverse health condition will occur or is occurring. In this manner, the disclosed techniques may allow detection or prediction of such events, e.g., even if there are no physical manifestations apparent. The probability or likelihood indication may include a probability score indication that provides a percentage or likeliness that a particular adverse health event will occur within a predetermined time period in the future (e.g., within the next 30 days or other desired period of time for knowing the likeliness).

In some examples, the probability score may be based on respective physiological parameter values corresponding to physiological parameters acquired from one or more medical devices. In some examples, the physiological parameters may include heart rate variability (HRV), night heart rate (NHR), day heart rate (DHR), patient activity (ACT), atrial fibrillation (AF), and/or ventricular rate. In addition, the physiological parameters may include subcutaneous tissue impedance values or subcutaneous tissue impedance scores. In other examples, the physiological parameters may include posture parameters, such as body posture (e.g., active angle), posture change, e.g., posture change count, nighttime rest to daytime active angle, respiration rate (RR), R-R intervals, respiratory effort, temperature, short term HRV, R-wave amplitude, heart sounds, and/or chronotropic incompetence. Other physiological parameters may include activity parameters, such as day activity, night activity, or stepping-out-of-bed count, cough parameters, such as cough magnitude and/or count, other accelerometer data values, etc.

In some examples, an IMD (e.g., an insertable monitoring device) may detect the maximum slew of S1, amplitude or energy of S1, S1-S2 interval, and amplitude or energy of S3 and how S3 changes over time as measured by the subcutaneously-inserted device (e.g., using a 3-axis accelerometer). Such parameters may be further incorporated as one diagnostic element of the risk score in the probability model (e.g., in a Bayesian framework). In this way, the IMD or an external device may incorporate heart sounds as a evidence node in a probability model as disclosed herein.

In addition, orthogonal clinical parameters may be included as input for the probability model. For example, B-type natriuretic peptide (BNP), measures of renal dysfunction, blood pressure, core body temperature, or other physiological parameters capable of identifying heart failure or other health threatening conditions may serve as input to the probability model.

In addition, the probability model may be able to input other known clinical-risk stratifiers, such as ejection fraction (EF), systolic vs. diastolic HF, history of hypertension, diabetes, COPD, anemia, sleep apnea, or atrial fibrillations, etc. In some examples, the probability model may be configured to modify a threshold for an individual parameter using, for example, one or more of the clinical-risk stratifiers. For example, the probability model may adjust a heart rate threshold to a higher value for a diastolic HF patient (e.g., EF>50%) compared to a systolic HF patient (EF<35%). In some examples, the probability model may change the prior probability for the probability model using, for example, one or more of the clinical-risk stratifiers.

Processing circuitry of a device (e.g., a remote server, tablet, implanted or patient-worn medical device, etc.) may determine respective values for each physiological parameter. The physiological parameter values may be obtained directly from various medical devices or may be obtained from one or more data servers. For example, the processing circuitry of an implantable medical device (IMD) may determine subcutaneous tissue impedance values and fluid indices to determine a subcutaneous tissue impedance score. In some examples, the processing circuitry of the IMD or another medical device may determine RR, NHR, patient activity, etc. The one or more medical devices may transmit the data to a data server (e.g., remote server, cloud server, etc.) for further processing according to the techniques disclosed herein.

In some examples, processing circuitry of a medical device may be configured to determine the RR or other respiratory parameter values of a patient based on fluctuations of the subcutaneous tissue impedance values. In other examples, another medical device may determine the RR of the patient based on subcutaneous tissue impedance values received from a subcutaneously implanted IMD. In some examples, processing circuitry of a medical device may determine RR using subcutaneous tissue impedance values in accordance with the techniques described in U.S. application Ser. No. 16/450,250 by Sarkar et al., entitled "SENSING RESPIRATION PARAMETERS BASED ON AN IMPEDANCE SIGNAL," filed on Jun. 24, 2019, and commonly-assigned and co-pending applications by Sarkar et al., entitled "DETERMINING HEART CONDITION STATUSES USING SUBCUTANEOUS IMPEDANCE MEASUREMENTS," and "DETERMINING HEALTH CONDITION STATUSES USING SUBCUTANEOUS IMPEDANCE MEASUREMENTS," both filed on even date herewith and incorporated herein by reference in their entirety.

In one non-limiting example, a medical device may be implanted subcutaneously within a patient in order to measure subcutaneous tissue impedances and transmit subcutaneous tissue impedance data and/or fluid indices to a data server or other external device. In such examples, the IMD, in conjunction with one or more other devices, such as the data server or external device, may use the subcutaneous tissue impedance data and/or fluid indices to determine a subcutaneous tissue impedance score that indicates how much risk a patient might have of experiencing a HF event or other health threat in the near term. In some examples, the IMD may determine the fluid indices, monitor fluctuations in subcutaneous tissue impedances (e.g., impedance changes in the interstitial fluid within a subcutaneous layer of the patient), and transmit subcutaneous tissue impedance scores to one or more other devices for further processing. In any event, the IMD and/or another medical device may use subcutaneous tissue impedance data to determine a subcutaneous tissue impedance score in accordance with techniques described in a commonly-assigned and co-pending application by Sarkar et al., entitled "DETERMINING HEART CONDITION STATUSES USING SUBCUTANEOUS IMPEDANCE MEASUREMENTS," filed on even date herewith, and incorporated herein by reference in its entirety. In some examples, the IMD may be configured to further determine the RR of a patient based on fluctuations (within a frequency range associated with respiration) of the subcutaneous tissue impedance values measured by the IMD as further discussed herein. In other examples, another medical device may determine the RR of the patient based on subcutaneous tissue impedance values received from an IMD.

Example medical devices, some of which are subcutaneously implantable or include subcutaneously implantable components, include pulse oximeters, blood pressure cuffs, defibrillators, pacemakers, cardioverters, thermometers, accelerometers, photoplethysmogram (PPG) probes, etc. In general, any physiological parameter that indicates a worsening health condition may be used to determine a probability score according to one or more of the various example techniques disclosed herein. Furthermore, an index that indicates worsening heart failure may be any index that is determined to indicate a trend in the parameter that reflects worsening heart failure. For example, just as impedance scores and respiration rates may be used to determine one or more evidence nodes for the probability model, other similar examples include indices or metrics of increased ventricular filling pressures or other morbidities associated with worsening HF experienced by a patient.

In one example, the disclosure provides a system for monitoring health events. In some examples, the system includes an implantable medical device (IMD) including a plurality of electrodes and configured for subcutaneous implantation in a patient, wherein the IMD is configured to determine one or more subcutaneous tissue impedance measurements via the electrodes. The system further includes processing circuitry coupled to the one or more storage devices. In some examples, the processing circuitry is configured to: determine a respective one or more values for each of a plurality of physiological parameters, the plurality of physiological parameters including one or more subcutaneous tissue impedance parameters determined from the one or more subcutaneous tissue impedance measurements, identify a diagnostic state for each of the physiological parameters based on the respective values, the diagnostic states defining a plurality of evidence nodes for a probability model, and determine, from the probability model, a probability score indicating a likelihood that the patient (a) is experiencing an adverse health event or (b) is likely to experience the adverse health event within a predetermined amount of time.

In another example, the disclosure provides a method including determining a respective one or more values for each of a plurality of physiological parameters, the plurality of physiological parameters including one or more subcutaneous tissue impedance parameters determined from one or more subcutaneous tissue impedance measurements, identifying a diagnostic state for each of the physiological parameters based on the respective values, the diagnostic states defining a plurality of evidence nodes for a probability model, and determining, from the probability model, a probability score indicating a likelihood that the patient (a) is experiencing an adverse health event or (b) is likely to experience the adverse health event within a predetermined amount of time.

In another example, the disclosure provides a computer-readable storage-medium having stored thereon instructions that, when executed, cause one or more processors to at least determine a respective one or more values for each of a plurality of physiological parameters, the plurality of physiological parameters including one or more subcutaneous tissue impedance parameters identified from one or more subcutaneous tissue impedance measurements, identify a diagnostic state for each of the physiological parameters based on the respective values, the diagnostic states defining a plurality of evidence nodes for a probability model, and determine, from the probability model, a probability score indicating a likelihood that the patient (a) is experiencing an adverse health event or (b) is likely to experience the adverse health event within a predetermined amount of time.

The disclosure also provides means for performing any of the techniques disclosed herein, as well as non-transitory computer-readable media including instructions that cause a programmable processor to perform any of the techniques disclosed herein.

The summary is intended to provide an overview of the subject matter described in this disclosure. It is not intended to provide an exclusive or exhaustive explanation of the systems, device, and methods described in detail within the accompanying drawings and description herein. Further details of one or more examples of this disclosure are set forth in the accompanying drawings and in the description below. Other features, objects, and advantages will be apparent from the description and drawings, and from the claims.

BRIEF DESCRIPTION OF THE DRAWINGS

Like reference characters denote like elements throughout the description and figures.

DETAILED DESCRIPTION

Figure 1:
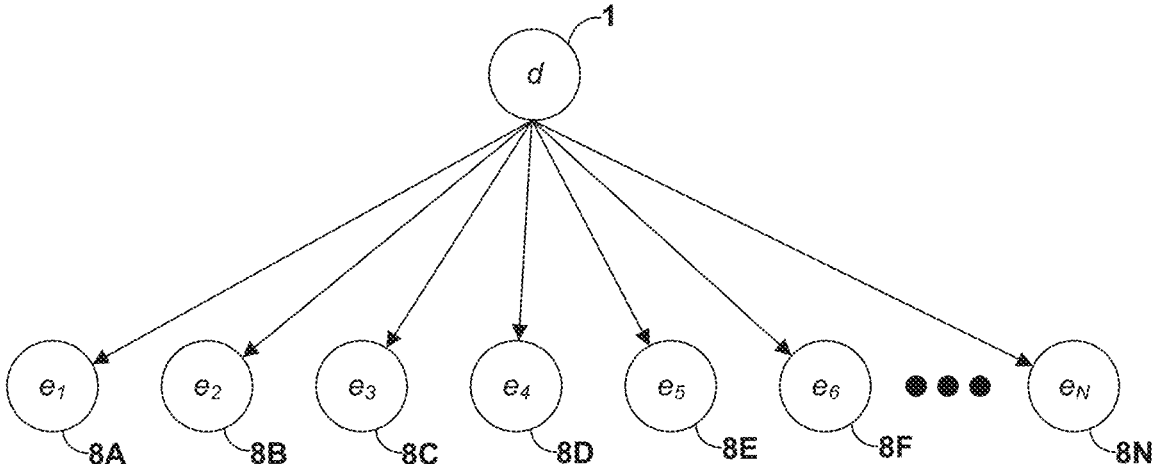
FIG. 1 is an example diagram of a probability framework including evidence nodes from diagnostic states of various physiological parameters and one parent node.

This disclosure describes techniques for providing an early warning for various health or heart conditions using prediction and probability modeling to determine a probability or likeliness indicator that an adverse health condition will occur or is occurring. In some examples, the probability score may be based on respective physiological parameter values corresponding to physiological parameters acquired from one or more medical devices. Processing circuitry of a device, e.g., a remote server, tablet, or one or more implanted, patient-worn, or external medical devices (which may have sensed values of one or more of the physiological parameters) may determine respective values for each physiological parameter, and determine the probability score based on the physiological parameter values.

In some examples, the prediction and/or probability modeling according to the techniques described herein may include Bayesian Belief Networks (BBN) or Bayesian machine learning (ML) models (these sometimes referred to as Bayesian Networks or Bayesian frameworks herein), Markov random fields, graphical models, artificial intelligence (AI) models (e.g., Naive Bayes classifiers), and/or other belief networks, such as sigmoid belief networks, deep belief networks (DBNs), etc. In other examples, the disclosed technology may leverage non-Bayesian prediction or probability modeling, such as frequentist inference modeling or other statistical models. In addition, known model-selection techniques, such as Bayesian information criterion (BIC) or Akaike information criterion (AIC), may be used to evaluate probability models prior to use.

In some examples, an integrated diagnostics model may be used to determine a number of criteria that are met based on each physiological parameter. For example, the probability model may determine that X of Y criteria have been met with respect to the physiological parameters. In such examples, Y may be the maximum number of criteria possible given the particular configuration of physiological parameters the probability model is using, and X may be a variable less than or equal to Y that increments based on the physiological parameters meeting certain criteria. In an illustrative example, the probability model may increment X in response to determining that the patient has an impedance score indicating a high diagnostic state and as such, may increment X.

Processing circuitry may determine, from the respective physiological parameter values, diagnostic states for each physiological parameter. A subcutaneous tissue impedance score, for example, may be used to determine a diagnostic state for the subcutaneous tissue impedance. Processing circuitry may compare the subcutaneous tissue impedance score to one or more risk thresholds to determine a diagnostic state of high (H) risk, medium (M) risk, or low (L) risk, in some examples. In some examples, processing circuitry may determine a joint diagnostic state based on multiple physiological parameters that are independent of one another.

In some examples, diagnostic states may include a finite number of potential diagnostic states for each physiological parameter (e.g., very high, high, medium, low, very low, etc.). For example, the diagnostic states may include states of high risk, medium risk, or low risk, for each physiological parameter. In some instances, one or more of the physiological parameters can have a different number of potential diagnostic states (e.g., one state, two states, three states, or more), whereas other physiological parameters may have a greater or lesser number of potential diagnostic states. For example, NHR may have three diagnostic states (H, M, and L), whereas AF may have less than three diagnostic states (H and L). In other examples, diagnostic states may include a continuum or sliding spectrum of diagnostic state values, rather than discrete states.

Diagnostic states of the physiological parameters may be independent for each physiological parameter. For example, a diagnostic state for a first set of one or more physiological parameters may be independent of diagnostic states associated with one or more other physiological parameters. In some examples, the probability mode framework, such as a BBN framework, may include additional physiological parameters, where the respective values of the physiological parameters are conditionally independent of one another. In an example, a high night heart rate may indicate an increase in sympathetic tone associated with a worsening condition. In addition, a decrease in impedance could reflect an increase in retained fluid. In such examples, each of these physiological parameters for impedance and night heart rate may provide indications of a heart failure event. In accordance with techniques of this disclosure, however, each of these conditionally independent parameters may provide stronger evidence when used together to predict an adverse health event.

In an illustrative example, two example physiological parameters may be conditionally independent of one another in the absence of an adverse health event. To illustrate, in the presence of the adverse health event, such as an HF event or fluid overload, the two example physiological parameter variables may be correlated or dependent on one another, but in the absence of the adverse health event, the two variables may change independently from one another, indicating that the two variables are conditionally independent of one another. For example, in some instances, RR will increase, whereas subcutaneous impedance will decrease during an adverse health event, such as HF, because HF may be the cause of these changes but not an effect of such changes. For example, an increase in RR does not cause HF, whereas RR may increase as a result of HF. In another example, RR may increase when a patient has anemia, whereas subcutaneous impedance may not change either way as a result of the anemia.

In some examples, processing circuitry may identify diagnostic states for physiological parameters that the processing circuitry has deemed relevant to the goal of the probability model. In a non-limiting example, if the goal is to determine the likelihood of a clinically-significant HF event (e.g., meriting a remote-care phone call or clinic visit or hospital admission) in the next 30 days, certain physiological parameters are more relevant to that probability determination than others, whereas a probability model for determining the likelihood of a preeclampsia-onset event in the next 60 days may require more or less physiological parameter inputs and may require a modified version of the previous probability model or a different probability model altogether.

The diagnostic states may serve as evidence nodes for the probability model. FIG. 1 represents an example probability model framework that includes a parent node 1 and a plurality of evidence nodes 8A-8N (collectively, "evidence nodes 8"). Parent node 1 represents the posterior probability (e.g., the probability that an adverse health event is to occur based on diagnostic states of evidence nodes 8). In an example, the adverse health event may include a HF event, where d=H, for illustration purposes. The probability model may include any number of evidence nodes 8, as illustrated by evidence node 8N. Each of evidence nodes 8 may correspond to one or more physiological parameters of a patient. As further discussed herein, each one of evidence nodes 8 may include a diagnostic state derived from one or more values that correspond to one or more physiological parameters. In examples involving discrete states of d, the posterior probability for the occurrence of the HF event (d=H) may be expressed as:

$$P(d = H \mid e_1, \ldots, e_N) = \frac{P(d = H) \prod_{i=1}^{N} P(e_i \mid d = H)}{\sum_{d_1} P(d) \prod_{i=1}^{N} P(e_i \mid d)}$$

In such examples, P(d) may represent a prior probability value, $P(e_i \mid d)$ may represent a conditional likelihood parameter, d represents parent node 1, and $e_1$-$e_N$ represent evidence nodes 8 in FIG. 1. Processing circuitry may determine the prior probability value and the conditional likelihood from existing physiological parameter values prior to clinical event d in previous clinical study data. In some examples, the conditional likelihood parameter may assume, using previous probability data, what probability distribution is likely to exist, such that the processing circuitry can assume what probability scores are unlikely based on previous probability data. In some examples, the prior probability value may include a probability distribution absent any diagnostic states to use as evidence nodes. In other words, the prior probability value is what processing circuitry may believe at a particular point of time, whereas the posterior probability is what processing circuitry may believe in the presence of incoming diagnostic information.

In some examples, the probability score may include a joint probability distribution. In an example, for a n-node Bayesian network (where $pa_i$ is the parent node of node $x_i$), the joint probability distribution may be expressed as:

$$P(x_i, \ldots, x_n) = \prod_{i}^{N} P(x_i \mid pa_i),$$

For example, a posterior probability may involve determining joint probability distributions and defining multiple combinations of conditional probabilities. A probability model may provide a framework for assumptions regarding the explicit relationship between parameter values to make these determinations more feasible. For example, Bayesian theory may assign explicit relationships between parameter values in order to determine posterior probability scores from the various evidence nodes 8 in FIG. 1.

For example, a posterior probability may include a posterior distribution. In some cases, the posterior distribution may include a Gaussian distribution. In other cases, the posterior distribution may include a non-Gaussian distribution.

In some examples, processing circuitry may determine and/or utilize conditional likelihood tables, BBN tables, prior probability values, etc., in accordance with the techniques described in U.S. application Ser. No. 13/391,376 by Sarkar et al., entitled "METHOD AND APPARATUS FOR MONITORING TISSUE FLUID CONTENT FOR USE IN AN IMPLANTABLE CARDIAC DEVICE," filed on Feb. 20, 2012, and is incorporated herein by reference in its entirety. For example, the conditional likelihood parameters may take the form of conditional likelihood tables defined for each diagnostic state for each physiological parameter. The posterior probability may then be tabulated for all possible combinations of diagnostic states to determine a posterior probability, or in some instances, a probability table, as described in U.S. application Ser. No. 13/391,376.

In some instances, a single evidence node may be derived from multiple physiological parameters, such as with a Multi-Variable Node (MVN). In an example, MVNs may be based on multiple physiological parameters, such as AF burden as a first physiological parameter and ventricular rate values as a second physiological parameter, where the physiological parameters factor into a single evidence node.

Processing circuitry may use the evidence nodes as input to a probability model to determine a posterior probability score. In such instances, the posterior probability score indicates a likelihood that a patient will experience an adverse health event within a predetermined period of time (e.g., within 30 days of determining the probability score). As discussed herein, the probability model may use as additional inputs the prior probability value and a conditional likelihood parameter to determine the posterior probability score. In some examples, processing circuitry may then update the probability model using the determined posterior probability score.

In some examples, the probability score is compared to one threshold for each of one or more risk levels (e.g., high risk threshold, medium risk threshold, low risk threshold). In an example, the probability score may be compared to two thresholds to provide hysteresis in the alert decision. In such examples, an alert may be generated when the probability score crosses a first, higher threshold. The alert is ended when the probability score subsequently crosses a second, lower threshold. By generating alerts in this manner, a device may generate fewer "sporadic" alerts that may be misinterpreted by the patient or a clinician when the probability score fluctuates near the higher, alert threshold value. In addition, the device may provide hysteresis alerts for a plurality of risk levels. For example, medium and/or low risk alerts may also have hysteresis thresholds.

Figure 2:
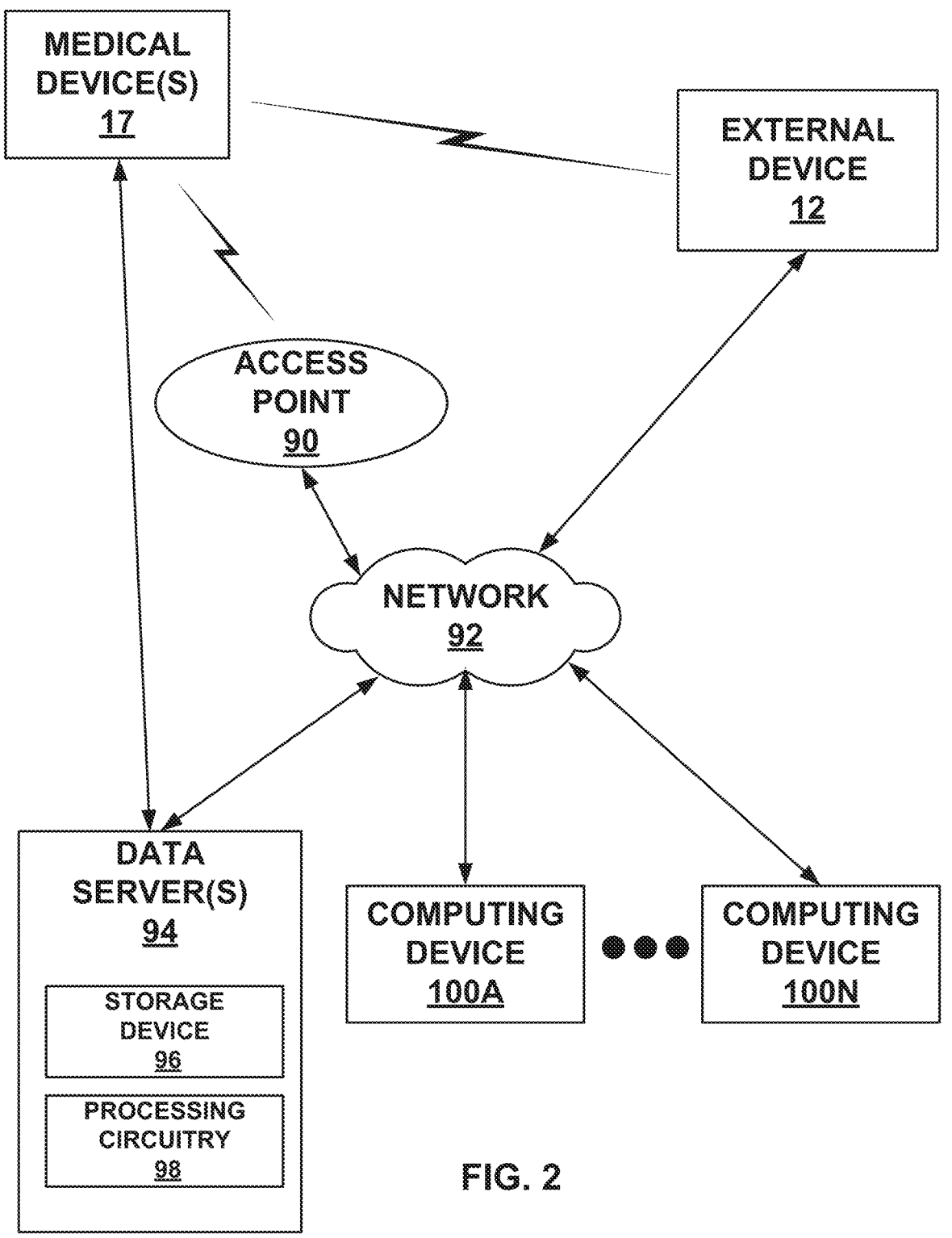
FIG. 2 is a block diagram illustrating an example system that includes medical device(s) used to obtain diagnostic states from the various physiological parameters for use as evidence nodes.

FIG. 2 is a block diagram illustrating an example system that includes one or more medical device(s) 17, an access point 90, a network 92, external computing devices, such as data servers 94, and one or more other computing devices 100A-100N (collectively, "computing devices 100"). In some examples, medical device(s) 17 may include an implantable medical device (IMD), such as IMD 10 described with reference to FIGS. 7-9. In this example, medical device(s) 17 may use communication circuitry 54 to communicate with external device 12 via a first wireless connection, and to communicate with an access point 90 via a second wireless connection.

In one or more of the various example techniques described with reference to FIG. 2, access point 90, external device 12, data server(s) 94, and computing devices 100 may be interconnected and may communicate with each other through network 92. Network 92 may include a local area network, wide area network, or global network, such as the Internet. The example system described with reference to FIG. 2 may be implemented, in some aspects, with general network technology and functionality similar to that provided by the Medtronic CareLink® Network, developed by Medtronic, Inc., of Minneapolis, MN.

Access point 90 may include a device that connects to network 92 via any of a variety of connections, such as telephone dial-up, digital subscriber line (DSL), or cable modem connections. In other examples, access point 90 may be coupled to network 92 through different forms of connections, including wired or wireless connections. In some examples, access point 90 may be a user device, such as a tablet or smartphone, that may be co-located with the patient.

Medical device(s) 17 may be configured to transmit data, such as sensed, measured, and/or determined values of physiological parameters (e.g., heart rates, impedance measurements, impedance scores, fluid indices, respiratory rate, activity data, cardiac electrograms (EGMs), historical physiological data, blood pressure values, etc.), to access point 90 and/or external device 12. In some examples, medical device(s) 17 may be configured to determine multiple physiological parameters. For example, medical device(s) 17 may include an IMD 10 configured to determine respiration rate values, subcutaneous tissue impedance values, EGM values. In such examples, IMD 10 may provide multiple physiological parameters to serve as evidence nodes to the probability model 19. Access point 90 and/or external device 12 may then communicate the retrieved data to data server(s) 94 via network 92.

In some instances, one or more of medical device(s) 17 may transmit data over a wired or wireless connection to data server(s) 94 or to external device 12. For example, data server(s) 94 may receive data from medical device(s) 17 or from external device 12. In another example, external device 12 may receive data from data server(s) 94 or from medical device(s) 17, such as physiological parameter values, diagnostic states, or probability scores, via network 92. In such examples, external device 12 may determine the data received from data server(s) 94 or from medical device(s) 17 and may store the data to storage device 84 (FIG. 3) accordingly.

In addition, one or more of medical device(s) 17 may serve as or include data server(s) 94. For example, medical device(s) 17 may include enough storage capacity or processing power to perform the techniques disclosed herein on a single one of medical device(s) 17 or on a network of medical device(s) 17 coordinating tasks via network 92 (e.g., over a private or closed network). In some examples, one of medical device(s) 17 may include at least one of the data server(s) 94. For example, a portable/bedside patient monitor may be able to serve as a data server, as well as serving as one of medical device(s) 17 configured to obtain physiological parameter values from patient 4. In other examples, data server(s) 94 may communicate with each of medical device(s) 17, via a wired or wireless connection, to receive physiological parameter values or diagnostic states from medical device(s) 17. In a non-limiting example, physiological parameter values may be transferred from medical device(s) 17 to data server(s) 94 and/or to external device 12.

In some cases, data server(s) 94 may be configured to provide a secure storage site for data that has been collected from medical device(s) 17 and/or external device 12. In some instances, data server(s) 94 may include a database that stores medical- and health-related data. For example, data server(s) 94 may include a cloud server or other remote server that stores data collected from medical device(s) 17 and/or external device 12. In some cases, data server(s) 94 may assemble data in web pages or other documents for viewing by trained professionals, such as clinicians, via computing devices 100. One or more aspects of the example system described with reference to FIG. 2 may be implemented with general network technology and functionality, which may be similar to that provided by the Medtronic CareLink® Network.

In some examples, one or more of computing devices 100 may be a tablet or other smart device located with a clinician, by which the clinician may program, receive alerts from, and/or interrogate medical device(s) 17. For example, the clinician may access data collected by medical device(s) 17 through a computing device 100, such as when patient 4 is in between clinician visits, to check on a status of a medical condition. In some examples, the clinician may enter instructions for a medical intervention for patient 4 into an application executed by computing device 100, such as based on a status of a patient condition determined by medical device(s) 17, external device 12, data server(s) 94, or any combination thereof, or based on other patient data known to the clinician.

One computing device 100 may transmit instructions for medical intervention to another of computing devices 100 located with patient 4 or a caregiver of patient 4. For example, such instructions for medical intervention may include an instruction to change a drug dosage, timing, or selection, to schedule a visit with the clinician, or to seek medical attention. In further examples, a computing device 100 may generate an alert to patient 4 (or relay an alert determined by a medical device 17, external device 12, or data sever 94) based on a probability score (e.g., posterior probability) determined from physiological parameter values of patient 4, which may enable patient 4 proactively to seek medical attention prior to receiving instructions for a medical intervention. In this manner, patient 4 may be empowered to take action, as needed, to address his or her medical status, which may help improve clinical outcomes for patient 4.

In the example illustrated by FIG. 2, data server(s) 94 includes a storage device 96 (e.g., to store data retrieved from medical device(s) 17) and processing circuitry 98. Although not illustrated in FIG. 2 computing devices 100 may similarly include a storage device and processing circuitry. Processing circuitry 98 may include one or more processors that are configured to implement functionality and/or process instructions for execution within data server(s) 94. For example, processing circuitry 98 may be capable of processing instructions stored in memory 96. Processing circuitry 98 may include, for example, microprocessors, DSPs, ASICs, FPGAs, or equivalent discrete or integrated logic circuitry, or a combination of any of the foregoing devices or circuitry. Accordingly, processing circuitry 98 may include any suitable structure, whether in hardware, software, firmware, or any combination thereof, to perform the functions ascribed herein to processing circuitry 98. Processing circuitry 98 of data server(s) 94 and/or the processing circuitry of computing devices 100 may implement any of the techniques described herein to analyze physiological parameters received from medical device(s) 17, e.g., to determine a probability score of patient 4.

In some examples, storage device 96 of data server(s) 94 may store a probability model 19. In some examples, external device 12 may store probability model 19. For example, data server(s) 94 may transmit probability model 19 to external device 12, where external device 12 may store the probability model 19 in a memory device of external device 12 (not shown in FIG. 2). External device 12 and/or data server(s) 94 may use the probability model 19 to determine a probability score with respect to a health risk for patient 4.

Processing circuitry 98 of data server(s) 94 and/or the processing circuitry of computing devices 100 may also retrieve instructions for utilizing a selected probability model (e.g., one selected using a known selection technique) and execute the probability model to determine the probability score. Processing circuitry 98 of data server(s) 94 and/or the processing circuitry of computing devices 100 may retrieve such data and instructions from storage device 96 or in some instances, from another storage device, such as from one of medical devices 17.

Storage device 96 may include a computer-readable storage medium or computer-readable storage device. In some examples, memory 96 includes one or more of a short-term memory or a long-term memory. Storage device 96 may include, for example, RAM, DRAM, SRAM, magnetic discs, optical discs, flash memories, or forms of EPROM or EEPROM. In some examples, storage device 96 is used to store data indicative of instructions for execution by processing circuitry 98.

Figure 3:
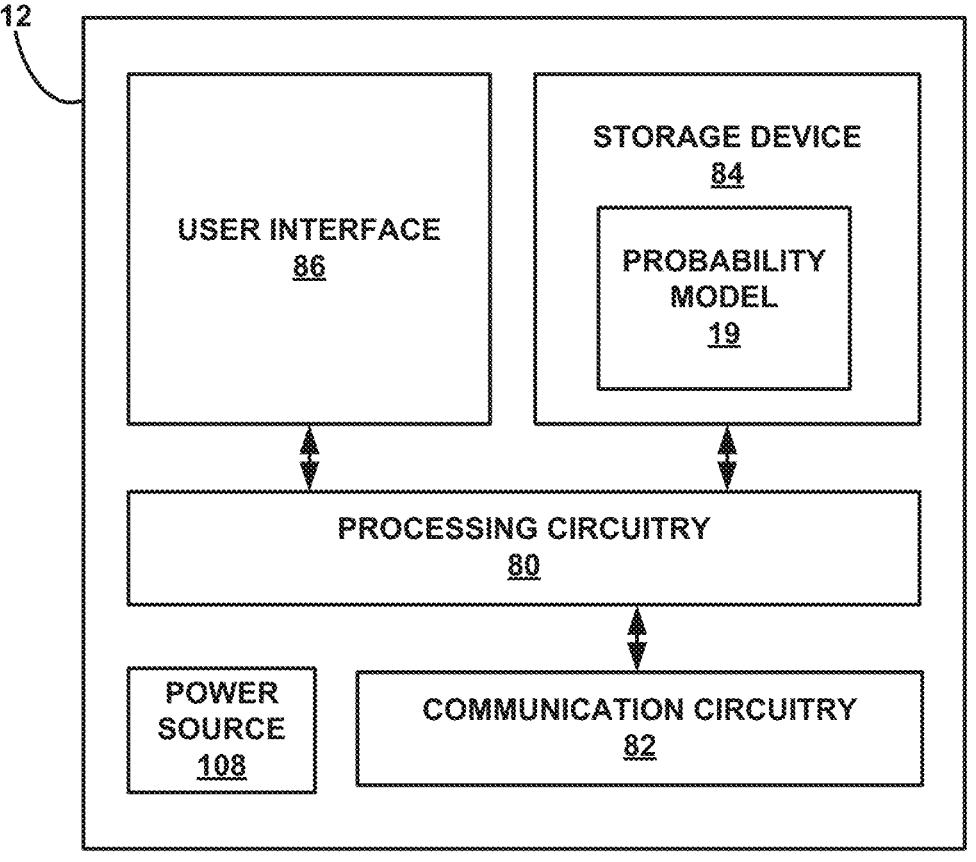
FIG. 3 is a functional block diagram illustrating an example configuration of the external device of FIG. 2.

FIG. 3 is a block diagram illustrating an example configuration of components of external device 12. In some examples, external device 12 includes processing circuitry 80, communication circuitry 82, storage device 84, and user interface 86.

Processing circuitry 80 may include one or more processors that are configured to implement functionality and/or process instructions for execution within external device 12. For example, processing circuitry 80 may be capable of processing instructions stored in storage device 84. Processing circuitry 80 may include, for example, microprocessors, DSPs, ASICs, FPGAs, or equivalent discrete or integrated logic circuitry, or a combination of any of the foregoing devices or circuitry. Accordingly, processing circuitry 80 may include any suitable structure, whether in hardware, software, firmware, or any combination thereof, to perform the functions ascribed herein to processing circuitry 80.

Communication circuitry 82 may include any suitable hardware, firmware, software or any combination thereof for communicating with another device, such as one of medical device(s) 17 (e.g., IMD 10). Under the control of processing circuitry 80, communication circuitry 82 may receive downlink telemetry from, as well as send uplink telemetry to, one of medical device(s) 17 (e.g., IMD 10), or another device (e.g., data server(s) 94). Communication circuitry 82 may be configured to transmit or receive signals via inductive coupling, electromagnetic coupling, near-field communication (NFC) technologies (e.g., inductive coupling, NFC or other communication technologies operable at ranges less than 10-20 cm), RF communication, Bluetooth®, Wi-Fi™, or other proprietary or non-proprietary wireless communication schemes. Communication circuitry 82 may also be configured to communicate with devices other than medical device(s) 17 via any of a variety of forms of wired and/or wireless communication and/or network protocols.

Storage device 84 may be configured to store information within external device 12 during operation. Storage device 84 may include a computer-readable storage medium or computer-readable storage device. In some examples, storage device 84 includes one or more of a short-term memory or a long-term memory. Storage device 84 may include, for example, RAM, DRAM, SRAM, magnetic discs, optical discs, flash memories, or forms of EPROM or EEPROM. In some examples, storage device 84 is used to store data indicative of instructions for execution by processing circuitry 80. Storage device 84 may be used by software or applications running on external device 12 to temporarily store information during program execution.

Storage device 84 may store one or more probability models 19. Storage device 84 may also store historical data, diagnostic state data, physiological parameter values, probability scores, etc.

Data exchanged between external device 12 and medical device(s) 17 may include operational parameters (e.g., physiological parameter values, diagnostic states, etc.). External device 12 may transmit data including computer readable instructions which, when implemented by medical device(s) 17, may control medical device(s) 17 to change one or more operational parameters and/or export collected data (e.g., physiological parameter values). For example, processing circuitry 80 may transmit an instruction to medical device(s) 17 which requests medical device(s) 17 to export collected data (e.g., impedance data, fluid index values, and/or impedance scores, blood pressure, ECG records, etc.) to external device 12.

In turn, external device 12 may receive the collected data from medical device(s) 17 and store the collected data in storage device 84. Processing circuitry 80 may implement any of the techniques described herein to model physiological parameter values received from medical device(s) 17 to determine diagnostic states, probability scores, etc. Using the modeling techniques disclosed herein, processing circuitry 80 may determine a likelihood that the patient is experiencing an adverse health event (e.g., heart failure decompensation) or is likely to experience an adverse health event within a predetermined amount of time (e.g., within the next 3 days, 7 days, 10 days, 30 days, 40 days, etc.). In an illustrative example, the predetermined amount of time may be at least approximately 7 days from when the probability score is determined, such that the probability score indicates the likelihood that an adverse health event will occur in the next 7 days or indicates that the patient is likely already experiencing an adverse health event, such as heart failure decompensation.

External device 12 may be a computing device with a display viewable by a user and an interface for providing input to external device 12 (i.e., a user input mechanism). The user may be a physician technician, surgeon, electrophysiologist, clinician, or patient 4. In some examples, external device 12 may be a notebook computer, tablet computer, computer workstation, one or more servers, cellular phone, personal digital assistant, handheld computing device, networked computing device, or another computing device that may run an application that enables the computing device to interact with IMD 10. External device 12 is configured to communicate with IMD 10 and, optionally, another computing device, via wired or wireless communication. External device 12, for example, may communicate via NFC technologies (e.g., inductive coupling, NFC or other communication technologies operable at ranges less than 10-20 cm) and far-field communication technologies (e.g., Radio Frequency (RF) telemetry according to the 802.11 or Bluetooth® specification sets, or other communication technologies operable at ranges greater than NFC technologies). In some examples, external device 12 may include a programming head that may be placed proximate to the body of patient 4 near the IMD 10 implant site in order to improve the quality or security of communication between IMD 10 and external device 12.

In one example, a user, such as a clinician or patient 4, may interact with external device 12 through user interface 86. User interface 86 includes a display (not shown), such as a liquid crystal display (LCD) or a light emitting diode (LED) display or other type of screen, with which processing circuitry 80 may present information related to medical device(s) 17 (e.g., cardiac EGMs, blood pressure, subcutaneous impedance values, RR, etc.). In addition, user interface 86 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 80 of external device 12 and provide input. In other examples, user interface 86 also includes audio circuitry for providing audible notifications, instructions or other sounds to the user, receiving voice commands from the user, or both.

In some examples, user interface 86 of external device 12 may receive input from the user. The user interface may include, for example, a keypad and a display, which may for example, be a cathode ray tube (CRT) display, an LCD, or an LED display. The keypad may take the form of an alphanumeric keypad or a reduced set of keys associated with particular functions. External device 12 can additionally or alternatively include a peripheral pointing device, such as a mouse, via which the user may interact with the user interface. In some examples, a display of external device 12 may include a touch screen display, and a user may interact with external device 12 via the display. It should be noted that the user may also interact with external device 12 remotely via a networked computing device.

External device 12 may be coupled to external electrodes, or to implanted electrodes via percutaneous leads. In some examples, external device 12 may monitor subcutaneous tissue impedance measurements from IMD 10. External device 12 may be used to configure operational parameters for IMD 10. For example, external device 12 may provide a parameter resolution for IMD 10 that indicates a resolution of data that IMD 10 should be obtaining. Examples of resolution parameters may include a frequency at which the electrodes process impedance measurements or a frequency at which impedance measurements should be considered in determining a diagnostic state.

Power source 108 delivers operating power to the components of external device 12. Power source 108 may include a battery and a power generation circuit to produce the operating power. In some embodiments, the battery may be rechargeable to allow extended operation. Recharging may be accomplished by electrically coupling power source 108 to a cradle or plug that is connected to an alternating current (AC) outlet. In addition or alternatively, recharging may be accomplished through proximal inductive interaction between an external charger and an inductive charging coil within external device 12. In other embodiments, traditional batteries (e.g., nickel cadmium or lithium ion batteries) may be used. In addition, external device 12 may be directly coupled to an alternating current outlet to power external device 12. Power source 108 may include circuitry to monitor power remaining within a battery. In this manner, user interface 86 may provide a current battery level indicator or low battery level indicator when the battery needs to be replaced or recharged. In some cases, power source 108 may be capable of estimating the remaining time of operation using the current battery.

Figure 4:
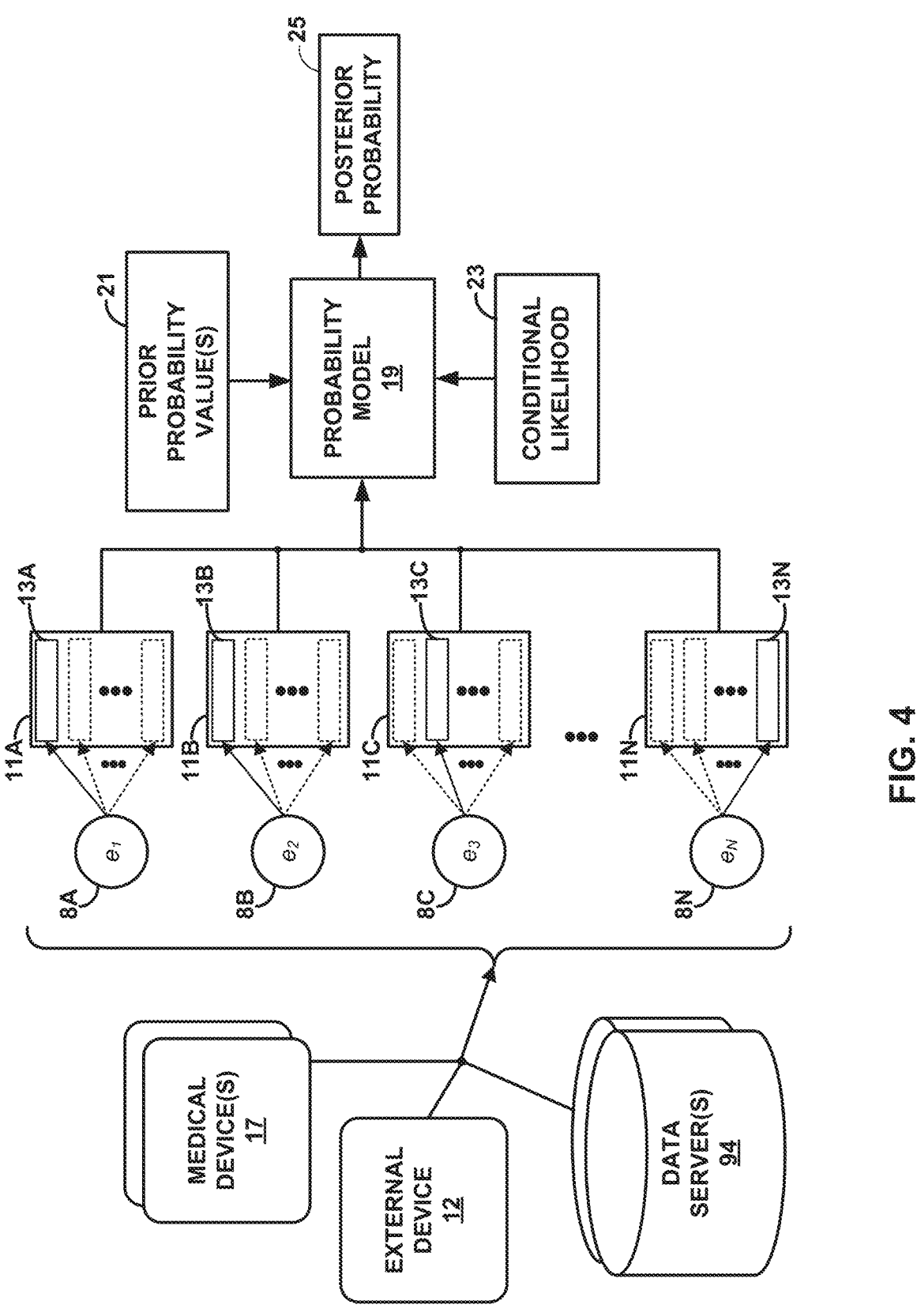
FIG. 4 is a functional block diagram illustrating an example framework for a probability model to determine health risk probabilities for a patient using evidence obtained from the system of FIG. 2.

FIG. 4 illustrates a framework that uses a medical system, such as system 2, to monitor health events and the likelihood of health events of patient 4. The medical system may include external device 12 or one or more of data server(s) 94. Although primarily described in terms of one or more data server(s) 94 determining the probability score, it will be understood that any one or more devices (e.g., processing circuitry of such devices), such as external device 12, one or more medical devices 17, or computing devices 100, may perform the probability determination using probability model 19 as described herein. In any event, FIG. 4 illustrates external device 12, medical device(s) 17, and/or data server(s) 94 as being configured to supply input to probability model 19.

In some examples, storage device 96 of data server(s) 94 may store the physiological parameter values that relate to one or more physiological parameters, which may have been received from one or more other devices of the system via network 92. Data server(s) 94 may store the physiological parameter values as raw data or as conditioned data via signal processing techniques. For example, data server(s) 94 may store, within storage device 96, fluid index values as values determined from subcutaneous tissue impedance data collected by one or more medical device(s) 17. In some examples, processing circuitry 98 of data server(s) determines fluid index values or scores based on subcutaneous impedance values measured by one or more medical device(s) 17. In some examples, processing circuitry of the medical device(s) or processing circuitry 80 of external device 12 determines the fluid index values or scores.

Processing circuitry, e.g., processing circuitry 98 of data server(s) 94, may store data received from medical device(s) 17 (e.g., from IMD 10) to a storage device, e.g., storage device 96 of data server(s) 94. In an example, storage device 96 may be configured to store measured and/or determined values of one or more subcutaneous tissue impedance parameters. The one or more subcutaneous tissue impedance parameters may include one or more subcutaneous tissue impedance scores or fluid index values. In some examples, data server 94 may receive impedance value measurements (e.g., raw or conditioned data) from medical device(s) 17, e.g., IMD 10, via network 92. In such examples, processing circuitry 98 of data server(s) 94 may determine the index or score values used to determine inputs to probability model 19. In some examples, medical device(s) 17, e.g., IMD 10, or external device 12 or another device may determine the index or score values from one or more subcutaneous tissue impedance measurements. IMD 10 (or another medical device 17) may determine one or more subcutaneous tissue impedance measurements via a plurality of electrodes of the medical device.

Processing circuitry 98 of data server(s) 94 may determine one or more subcutaneous tissue impedance scores using impedance value measurements. In some examples, data server(s) 94 may receive one or more subcutaneous tissue impedance scores, where another device, such as IMD 10, may determine the subcutaneous tissue impedance scores prior to transmitting the impedance scores to data server(s) 94. In any case, data server(s) 94 may receive data from medical device(s) 17 and determine, via probability model 19, a probability score based on the data.

With reference still to FIG. 4, processing circuitry 98 of data server(s) (or processing circuitry of any other device of the system) may, in some examples, perform the probability score determination using probability model 19 in accordance with the following. As described herein, processing circuitry 98 may be coupled to one or more storage devices such that processing circuitry 98 may leverage the various data repositories in order to determine the probability score.

In some examples, processing circuitry 98 may be configured to determine a respective one or more values for each of a plurality of physiological parameters. For instance, processing circuitry may determine one or more values for a first physiological parameter and one or more values for a second physiological parameter. In one example, the values may correspond to measurement readings determined via medical device(s) 17. For example, the values may include respiration rate values, ECG values, activity level values, etc. For example, the values may indicate at when patient 4 was active or when patient 4 was inactive. The values may include accelerometer values that indicate a posture of patient 4 or a change in the posture of patient 4 over time (e.g., a posture-change count). Posture change count may be based on z-axis accelerometer values. Other values may include periodic x, y, and z-axis accelerometer measurements.

In some examples, processing circuitry 98 may adjust the criteria for determining each diagnostic state as more information becomes available to processing circuitry 98 over time. For example, processing circuitry 98 may determine that one or more diagnostic states for one or more physiological parameters may be optimized. In some examples, processing circuitry 98 may determine such optimization potential based on the output of a ML model trained on posterior probability data, diagnostic states, and criteria performance data. In any event, processing circuitry 98 may adjust the criteria used (right-hand column below in Table 1) for determining the one or more diagnostic states for one or more physiological parameters.

In an illustrative and non-limiting example of how diagnostic states may be determined, Table 1 below shows diagnostic states in the left-hand column and criteria values (e.g., physiological parameter values) in the right-hand column. The criteria values provided below are merely to illustrate an example of how diagnostic states may correlate to criteria for determining a particular diagnostic state. Likewise, the physiological parameters below are provided as example physiological parameters, and in some examples, other physiological parameters may additionally or alternatively be used, such as heart sounds, stepping out of bed count, or other physiological parameters disclosed herein.

TABLE 1

| Diagnostic state | Physiological Parameter Values and Criteria |
|---|---|
| Impedance score | |
| H | ImpScore $\geq$ 7 |
| M | ImpScore $\geq$ 1 and ImpScore $\leq$ 6 |
| L | ImpScore = 0 |
| RR | |
| H | maxRR$_7$ $\geq$ 22 brpm OR cvarRR$_{30}$ $\geq$ 23 OR ND (RR$_{30}$ $\geq$ 20 brpm) $\geq$ 16 |
| M | minRR$_{30}$ $\geq$ 11.5 brpm and {Not 'H'} |
| L | {Not 'H' OR 'M'} |
| AF | |
| H | [{avgAFB$_7$ $\geq$ 1 hr OR ND(AFB$_{30}$ $\geq$ 6 hrs) $\geq$ 2} AND ND(AFB$_{30}$ $\geq$ 23 hrs) < 30] OR max2minAFB$_7$ > 3.5 hr OR max2minAFB$_{30}$ > 4.5 hr OR ND(AFB$_{30}$ > 6 hrs AND |

TABLE 1-continued

| Diagnostic state | Physiological Parameter Values and Criteria |
|---|---|
| | $VRAF_{30} \geq 90$ bpm) $\geq 1$ OR $ND(AFB_{30} > 23$ hrs AND $VRAF_{30} \geq 90$ bpm) $\geq 1$ |
| L | Not 'H' |
| NHR | |
| H | $ND(NHR_7 \geq 85$ bpm) $\geq 3$ OR $maxNHR_7 > 100$ bpm OR $avgNHR_{30} > 90$ bpm OR $avgNHR_7 > 90$ bpm OR $avgDHR\text{-}NHR_7 <- 1$ bpm |
| M | $\{ND(NHR_{30} \geq 85$ bpm) $\geq 3$ OR $maxNHR_{30} > 85$ bpm OR $maxNHR_7 > 85$ bpm OR $minNHR_{30} > 65$ bpm OR $avgDHR\text{-}NHR_7 < 3$ bpm$\}$ AND Not 'H' |
| L | $\{$Not 'H' OR 'M'$\}$ |
| HRV | |
| H | $ND(HRV_{30} \leq 60$ ms) $\geq 25$ OR $max2avgHRV_{30} \geq 85\%$ OR $minHRV_7 < 35$ ms OR $CSFRHRV_{30} <- 12$ |
| M | $\{ND(HRV_7 \leq 60$ ms) $\geq 2$ OR $ND(HRV_{30} \leq 60$ ms) $\geq 6$ OR $max2avgHRV_{30} \geq 65\%$ OR $minHRV_{30} < 55$ ms OR $avgHRV_{30} < 65$ ms OR $avgHRV_7 < 75$ ms OR $CSFRHRV_7 <- 2\}$ AND Not 'H' |
| L | $\{$Not 'H' OR 'M'$\}$ |
| ACT | |
| H | $ND(ACT_7 \leq 30$ min) $\geq 7$ OR$ND(ACT_{30} \leq 30$ min) $\geq 27$ OR $CSFRACT_7 < -43$ OR avg $ACT_7 < 10$ min |
| M | $\{ND(ACT_{30} \leq 30$ min) $\geq 11$ OR $max2avgACT_{30} \geq 150\%$ OR $CSFRACT_{30} <- 3$ OR $avgACT_{30} < 30$ min $\}$ AND Not 'H' |
| L | Not 'H' OR 'M' | where ND = number of days; bpm = beats per minute; CSAR = Cumulative Sum Adaptive Reference, IMP = impedance; CSFR = Cumulative Sum Fixed Reference, Thr = Threshold; AdapThr = Adaptive Threshold; Subscripts indicate preceding timeframe (e.g., look-back window) size.

In some examples, the impedance score (ImpScore) may be determined as follows:

The following elements add a score of 1:

$CSAR\text{-}IMP_{30} \geq 0.6*AdapThr$ for $\geq 1$ day $CSAR\text{-}IMP_7 \geq 0.6*AdapThr$ for $\geq 1$ day $CSAR\text{-}IMP_{30} \geq 1.7*AdapThr$ for $\geq 1$ day $CSAR\text{-}IMP_7 \geq 1.7*AdapThr$ for $\geq 1$ day $CSAR\text{-}IMP_{30} \geq 3.2*AdapThr$ for $\geq 1$ day $CSAR\text{-}IMP_7 \geq 1.5*AdapThr$ for $\geq 7$ days And the following elements add a score of 2:

$CSARIMP_7 \geq 3.2*AdapThr$ for $\geq 1$ day $CSARIMP_{30} \geq 1.5*AdapThr$ for $\geq 24$ days $AvgIMP_7 \leq 600\Omega$ $AvgIMP_{30} \leq 600\Omega$ Throughout this disclosure a day may generally refer to a 24-hour period. For example, a day may refer to midnight to midnight or some other 24-hour period. The same may generally be said about a week, month, or other time period.

As described herein, the plurality of physiological parameters may include one or more subcutaneous tissue impedance parameters identified from the one or more subcutaneous tissue impedance measurements. The one or more subcutaneous tissue impedance parameters may include a subcutaneous tissue impedance score, as well as fluid index values. The subcutaneous tissue impedance score may be determined in accordance with techniques described in a commonly-assigned and co-pending applications by Sarkar et al., entitled "DETERMINING HEART CONDITION STATUSES USING SUBCUTANEOUS IMPEDANCE MEASUREMENTS," and "DETERMINING HEALTH CONDITION STATUSES USING SUBCUTANEOUS IMPEDANCE MEASUREMENTS" filed on even date herewith, and incorporated herein by reference in their entirety. In other examples, the subcutaneous tissue impedance parameters may include subcutaneous tissue impedance measurements, fluid index values, statistical representations of subcutaneous tissue impedance measurements, respiration rate, etc. In some examples, fluid index values may be derived from other sensors, such as intra-cardiac pressure sensors. For example, an intra-cardiac pressure sensor may detect higher pressures, which may be indicative of a higher amount of fluid. The cardiac pressure data may be used to compute one or more fluid index values and/or scores based on fluid index values.

In some examples, the physiological parameters include at least one value corresponding to a RR of patient 4. The RR of patient 4 may be determined in a number of different ways (e.g., chest wall movement, acute changes in subcutaneous fluid with respiratory cycle induced venous return changes, etc.). In some examples, processing circuitry 80 is configured to identify, based on the one or more subcutaneous tissue impedance measurements, a periodic variation (e.g., increase and decrease) in subcutaneous tissue impedance. In such examples, processing circuitry 98 is configured to determine, based on the periodic variation (e.g., increase and decrease) in subcutaneous tissue impedance, the RR of patient 4. In some examples, one of medical device(s) 17 may determine RR in accordance with other techniques, such as by using R-wave amplitude changes or changes in R-R intervals. For example, one of medical device(s) 17 may use R-R interval parameters (e.g., R-wave to R-wave interval) to determine the RR of patient 4. R-R intervals may be derived from ECG measurements. In another example, one of medical device(s) 17 may determine RR from PPG, accelerometer, or optical sensors.

In such examples, IMD 10 or processing circuitry 98 may utilize the impedance measurements to determine a RR of patient 4. The subcutaneous tissue impedance values may include low-frequency fluctuations that correspond to the RR. Subcutaneous impedance is sensitive to conductivity of fluid around IMD 10. With each inhalation, the intrathoracic pressure reduces increasing pulmonary blood volume. An increase in pulmonary blood volume tends to lead to a reduction of pulmonary artery pressure. A reduction of pulmonary artery pressure tends to cause a reduction of right arterial pressure and an increase of venous return. This may cause a reduction of extracellular/extra-vascular volume and thus, an increase in impedance. The opposite sequence of events leads to reduction of impedance with exhalation. In another example, a movement of the chest wall of patient 4 may lead to changes in measured impedance, as well. In some examples, IMD 10 may determine respiration rate (RR) in accordance with U.S. application Ser. No. 16/450, 250 by Sarkar et al., entitled "SENSING RESPIRATION PARAMETERS BASED ON AN IMPEDANCE SIGNAL," filed on Jun. 24, 2019, incorporated herein by reference in its entirety.

In some examples, processing circuitry, e.g., processing circuitry 50 of IMD 10, processing circuitry 80 of external device 12, or processing circuitry 98 of server 94, may identify the occurrence of missing data (e.g., the occurrence of corrupt data, gaps in data series, etc.). For example, processing circuitry 98 may identify the occurrence of missing data. In some examples, processing circuitry 98 may identify the occurrence of missing data, such as when unable to access certain data from an expected storage location of storage device 96 or when a missed transmission from IMD 10 or medical devices 17 has occurred. In another example, processing circuitry 98 may determine that a data series includes a data gap indicating the occurrence of missing data (e.g., corrupt data). Processing circuitry 98 may identify the data gap, for example, based on a known transmission rate. In one example, medical device(s) 17 may transmit impedance values to processing circuitry 98 on a periodic basis (e.g., daily). In such examples, processing circuitry 98 may determine the occurrence of missing data based on data missing for a particular timeframe, where impedance data is available preceding and/or following the particular timeframe. In another example, processing circuitry 98 may determine that certain data is corrupt or that the data contains outlier data that may indicate a transmission error or error in obtaining the data. In any event, processing circuitry 98 may transmit a request to medical device(s) 17 for the missing data or may simply notify medical device(s) 17 of the identified discrepancy.

Missing data may occur for any number of different reasons, such as a failed data transmission or if one of medical device(s) 17 is unavailable at the time to perform measurements for a particular measurement cycle. For example, IMD 10 may be unavailable to perform certain impedance measurements due to processing circuitry 50 responding to competing measurement requests. Missing data may also occur when a transmission of data fails from one device to another device. In some examples, missing data may include missing diagnostic states for a particular physiological parameter, missing data used to determine the diagnostic states, etc.

In one example involving missing data, processing circuitry 80 or processing circuitry 98 may determine that certain data was expected to be received from one of medical device(s) 17, but that the data was not received. In some examples, processing circuitry 80 or processing circuitry 98 may determine that certain data was not received by detecting one or more dropped packets or by identifying gaps in data. In some examples, external device 12 or server 94 may determine inconsistencies in data indicating corrupt, misleading, or otherwise discrepant data. For example, external device 12 may compare data received from one of medical devices 17 to data received from another one of medical devices 17 to determine whether the data is aligned or in agreement. In examples where external device 12 or server 94 identifies missing data, external device 12 or server 94 may transmit a notification to a particular medical device 17 (e.g., via communication circuitry 54) identified with the missing data, notifying the medical device 17 of the missing data. In response, the particular medical device 17 may attempt to correct for the discrepancy, for example, by identifying a cause of the missing data and/or attempting to resend the missing data to external device 12 or server 94.

In some examples, upon identifying the occurrence of missing data, processing circuitry, e.g., processing circuitry 50 of IMD 10, processing circuitry 80 of external device 12, or processing circuitry 98 of server 94, may be configured to determine modified inputs to probability model 19, for example, based on an amount of data missing when determining average data values (e.g., $avgAFB_7 > 1$ hr, etc.) or based on threshold comparison types for determining minimum and maximum data values (e.g., $maxRR_7 \geq 22$ brpm, $minHRV_{30} < 55$ ms, $minRR_{30} > 11.5$ brpm, etc.).

In an illustrative example with reference to Table 1, processing circuitry 98 may determine average values with respect to a 30-day average or 7-day average. If processing circuitry 98 identifies the occurrence of missing data, processing circuitry 98 may determine how much data is missing. In a non-limiting example, if processing circuitry 98 determines that at least a portion of the data is available for a particular timeframe, processing circuitry 98 may proceed with determining the average for the particular timeframe. For example, processing circuitry 98 may determine that data for a particular parameter is available for at least 10 days out of the last 30 days. As such, processing circuitry 98 may determine that the portion of data available is sufficient to determine the 30-day average.

In a non-limiting example involving 7-day averages, processing circuitry 98 may determine that data for a particular parameter is available for at least 4 days out of the last 7 days. As such, processing circuitry 98 may determine that the 4-day portion of data for the particular parameter is sufficient to determine the 7-day average for the particular parameter. Various thresholds may be used for determining whether a portion of data is sufficient. In some examples, the various thresholds (e.g., 4 out of 7 days, 3 out of 7 days, etc.) may depend on the particular parameter at issue. In another example, the various thresholds may be set uniformly regardless of the parameter. In any event, if processing circuitry 98 determines that a threshold is not satisfied for a particular parameter (e.g., 3 days' worth of data available out of 30 days), processing circuitry 98 may exclude the data for the particular parameter from being used to determine the probability score.

In some examples, processing circuitry 98 may determine whether to use certain physiological parameters in determining the probability score based on the type of threshold comparison used to determine a respective diagnostic state (e.g., Table 1). With the occurrence of missing data, processing circuitry 98 may determine whether a sufficient amount of data is received to determine a diagnostic data based on the type of threshold comparison used. For example, processing circuitry 98 may utilize various types of threshold comparisons when determining diagnostic states, such as (a) whether a maximum data value in the last X number of days is greater than a threshold or (b) whether a minimum data value in the last X number of days is less than a threshold. For example, when determining diagnostic states, processing circuitry 98 may determine (a) whether the $maxRR_7 \geq 22$ brpm; or may determine (b) whether $minHRV_{30} < 55$ ms. For these particular threshold compari-
son types (e.g., max>threshold, min<threshold, etc.), if a
respective threshold is met of this type, processing circuitry
98 may determine that the availability of at least X number
of days' worth (e.g., 1 day) of data for the particular
parameter is sufficient to use the parameter in determining
the probability score. In an illustrative example, if process-
ing circuitry 98 determines that at least 1 day of data is
available for maxRR, and that the 1 day of maxRR data
satisfies the threshold of ≥22 brpm, then processing circuitry
98 may determine and use the RR diagnostic state as one of
the physiological parameter inputs to probability model 19,
assuming no other missing data issues with RR.

In the second example above, if processing circuitry 98
determines that, for example, 2 days of data are available for
minHRV in the past 30 days, but that at least one of the 2
days of minHRV data satisfies the threshold of <55 ms, then
processing circuitry 98 may determine and use the HRV
diagnostic state as one of the physiological parameter inputs
to probability model 19, assuming no other missing data
issues with HRV. In any event, processing circuitry 98 may
still use the HRV data or the RR data, in the above examples,
to determine diagnostic states regardless of whether the
threshold is met In addition, processing circuitry 98 may utilize other
threshold comparison types when determining diagnostic
states that may result in different outcomes with respect to
how processing circuitry 98 handles the occurrence of
missing data. For example, other types of threshold com-
parisons may include: (a) whether a minimum data value is
greater than a threshold or (b) whether a maximum data
value is less than a threshold. In one example, when deter-
mining diagnostic states, processing circuitry 98 may deter-
mine whether the $minRR_{30} > 11.5$ brpm. In such examples
having this type of threshold (e.g., minimum value greater
than threshold, maximum data less than threshold, etc.),
processing circuitry 98 may determine that if the occurrence
of missing data results in the availability of less than X
number of days' worth of data in the past 30 days, than the
particular physiological parameter may be excluded from
being used as one of the physiological parameter inputs to
probability model 19. In such instances, processing circuitry
98 may determine, similar to the example involving aver-
ages above, whether at least 10 of 30 days' worth of data is
available, whether at least 4 of 7 days' worth of data is
available, etc. If not, processing circuitry 98 may exclude the
particular physiological parameter from being used as one of
the physiological parameter inputs to probability model 19.

In some examples, instead of excluding a particular
physiological parameter where there is missing data, pro-
cessing circuitry 98 may skip a particular calculation involv-
ing the missing data where the diagnostic states may be
based on multiple other calculations. That is, processing
circuitry 98 may instead determine the diagnostic state for
the physiological parameter without using the particular
calculation that may cause skewed results due to the missing
data. In any event, processing circuitry 98 may employ one
or more of missing data algorithms, in order to avoid
skewing results based on overgeneralizations of incomplete
data. For example, a determination of whether a maximum
data value in the last 30 days is less than a threshold may be
skewed in the presence of only one data points for the 30
days, even if the one data point is less than the threshold. In
such instances, probability model 19 and the diagnostic state
calculations may benefit from one or more missing data
algorithms so as to avoid overgeneralizing an incomplete
data set or reaching a false conclusion based on the incomplete data set. In another example of missing data algo-
rithms, processing circuitry 98 may utilize interpolation or
extrapolation techniques where processing circuitry 98 is
missing data for a given physiological parameter, but where
a sufficient amount of data is available to interpolate or
extrapolate to arrive at a more complete data set.

In some examples, processing circuitry 98 may be con-
figured to identify diagnostic states 11A-11N (collectively,
"diagnostic states 11") for each of the physiological param-
eters based on the respective values. For example, various
thresholds may be used to determine a diagnostic state of a
physiological parameter. In some examples, processing cir-
cuitry 80 is configured to select, from at least three potential
diagnostic states, a single diagnostic state for each of evi-
dence nodes 8. For example, the diagnostic state may be
high, medium, low, where some physiological parameters
may include more or less diagnostic states (H and L). In the
example described with reference to FIG. 4, the diagnostic
states are selected from N number of diagnostic states. In a
few examples, diagnostic state 13A has a first diagnostic
state (e.g., high or very high), where diagnostic state 13C has
a second diagnostic state, where the first diagnostic state
may include a high risk categorization and the second
diagnostic state may include a medium risk categorization
depending on the respective one or more physiological
parameter values. Further, diagnostic state 13B correspond-
ing to evidence node 8B may be high or very high and
diagnostic state 13N corresponding to evidence node 8N
may be low or very low.

The diagnostic states may be determined independently
for each physiological parameter. For example, processing
circuitry 98 may compare the values obtained for a first
physiological parameter to one or more thresholds to deter-
mine a diagnostic state for the first physiological parameter
independently of processing circuitry comparing values
obtained for a second physiological parameter to one or
more thresholds to determine a diagnostic state for the
second physiological parameter. In some examples, data
server(s) 94 may receive the diagnostic state for one or more
of the diagnostic states 11. In other examples, data server(s)
94 may determine the diagnostic state for the diagnostic
state for one or more of the diagnostic states 11 based on the
respective values of the physiological parameters. In any
event, diagnostic states 11 define evidence nodes 8 for
probability model 19. In other words, diagnostic states 11
serve as evidence nodes 8 for probability model 19.

In some examples, the physiological parameters may
include long-term HRV, NHR, ACT, AF, or ventricular rate.
Moreover, the physiological parameters may include pos-
ture, respiratory effort, temperature, short term HRV,
R-wave amplitude, heart sound, nighttime rest versus day-
time active body angle, chronotropic incompetence, B-type
natriuretic peptide (BNP), renal dysfunction, or blood pres-
sure. In addition, physiological parameters may further
include RR interval, posture-change count and accelerom-
eter data values. In any event, the physiological parameters
may include subcutaneous tissue impedance parameters
from IMD 10 or another medical device 17.

In some examples, probability model 19 may include a
Bayesian framework or BBN. Other suitable probability
models may be used to determine probability scores given
diagnostic states of physiological parameters. For example,
a Bayesian ML model may be used to determine probability
scores based on diagnostic states of physiological param-
eters. Processing circuitry may train probability model 19 on
values associated with the physiological parameters. In other
examples, processing circuitry may include as input to probability model 19 prior probability value(s) 21 or conditional likelihood 23. For example, processing circuitry 98 may determine, from the plurality of physiological parameters, prior probability value 21. The prior probability value 21 may be determined from existing data. Processing circuitry 98 may also determine, from the plurality of physiological parameters, conditional likelihood parameter 23.

In some examples, processing circuitry 98 may determine the conditional likelihood, or P(e_i|d), from existing data. Processing circuitry 98 may utilize existing data from one or more patients or subjects, where the existing data is then used to determine conditional likelihood parameters of a model utilizing a probability theorem, such as Bayes rule.

In one example, the value of 'd' may represent the presence or absence of an HF event or other adverse health event. As such, processing circuitry 98 may use earlier data to determine whether a particular diagnostic criterion was satisfied before an HF event (e.g., $P(e_i|d=1)$) or whether the particular diagnostic criterion was satisfied when there was no HF event (e.g., $P(e_i|d=0)$). In an example, using a first evidence node $e_1$ as corresponding to 'impedance score', processing circuitry 98 may determine from a plurality of existing data points the conditional likelihood for: $P(e_1=H|d=1)$, $P(e_1=H|d=0)$, $P(e_1=M|d=1)$, $P(e_1=M|d=0)$, $P(e_1=L|d=1)$, and $P(e_1=L|d=0)$. That is, processing circuitry 98 may determine the conditional likelihood from data derived from True Positives, False Positives, False Negatives, and False Positives. In some examples, processing circuitry 98 use the same data to provide a desired sensitivity and specificity of HF detection. That is, posterior probability 25 may represent an estimate of positive predictive value (PPV) based on sensitivity, specificity and event rate (e.g., prior probability 21).

Processing circuitry 98 may determine the conditional likelihoods for each physiological parameter used as an input evidence node to probability model 19 (e.g., each of $e_i$). In some examples, processing circuitry 98 may then utilize the conditional likelihood probabilities to determine the probability model 19. In such examples, the determined probability model 19 may include a computable joint distribution.

As such, processing circuitry 98 may identify prior probability value 21 and/or the conditional likelihood parameter 23 as inputs to probability model 19 when determining the probability score. In such examples, the probability model may be expressed as:

$$P(d, e_1, \dots, e_N) = P(d) \prod\nolimits_{i=1}^{N} P(e_i \mid d),$$

wherein P(d) represents the prior probability value, P(e_i|d) represents the conditional likelihood parameter, d represents a parent node, and $e_1$-$e_N$ represent the evidence nodes.

In some examples, processing circuitry 98 may be configured to determine a probability score from probability model 19 based on evidence nodes 8. In an example, the BBN may have one or more child nodes (e.g., n-nodes as shown in FIG. 4) and a parent node, represented by posterior probability 25.

The probability score may include a likelihood that the patient is experiencing an adverse health event or is likely to experience the adverse health event within a predetermined amount of time. In an example, the adverse health event could be a worsening HF event (e.g., HF decompensation). The probability score may be expressed in terms of a percentage, a decimal number, or a threshold categorization, such as 50%, 0.5, or medium likelihood, where in this example, 50% corresponds to a threshold categorization of medium likelihood. In some examples, the probability score may be expressed in terms of a range such as >50% or between 50-60%.

In some examples, processing circuitry 98 may determine the probability score for predetermined amount of time in the future. This may be known as a look-forward period. In some examples, the predetermined amount of time is approximately 30 days relative to when the probability score is determined. For example, the probability score may indicate that patient 4 has a 50% chance of experiencing an adverse health event in the next 30 days. In some instances, the predetermined amount of time may be more or less than 30 days depending on the particular configuration of probability model 19. As such, probability model may determine a probability score that indicates the likelihood of an adverse health event, such as a heart failure worsening event, occurring within the predetermined timeframe (e.g., next 30 days).

Processing circuitry 98 may, in some instances, determine the predetermined amount of time, such that the predetermined amount of time serves as a buffer period. In other words, at the end of the predetermined amount of time (e.g., 30 days), processing circuitry 98 may determine another probability score using data received during a preceding timeframe (e.g., the last 30 or 60 days). Processing circuitry 98 may perform automatic probability determinations using probability model 19 after the predetermined amount of time and after each buffer period thereafter. In other examples, processing circuitry 98 may determine a probability score in response to receiving a command signal (e.g., from a user via a user interface). Processing circuitry 98 may alter the predetermined timeframe slightly to account for the different days in a month. For example, approximately 30 days may include 31 days, 29 days, or 28 days, for convenience of patient 4. That is, patient 4 may have an easier time tracking buffer periods based on months or weeks rather than based on strict 30-day periods.

In some examples, processing circuitry, e.g., processing circuitry 50 of IMD 10, processing circuitry 80 of external device 12, or processing circuitry 98 of data server(s) 94, may determine the probability score on a daily basis. For example, processing circuitry 98 may determine the probability score every day based on data corresponding to a previous X number of days. In some examples, processing circuitry 98 may store in storage device 96 diagnostic states for various parameters each day for a finite number of days, such as in a first in, first out (FIFO) buffer or sliding window. In some examples, processing circuitry 98 may store the last 30 diagnostic states for each parameter determined on a daily basis for the past 30 days. For example, processing circuitry 98 may store the last 30 diagnostic states for impedance scores determined on a daily basis for the past 30 days, store the last 30 diagnostic states for RR determined on a daily basis for the past 30 days, etc. Processing circuitry 98 may determine the probability score at a predefined time interval each day using the previous 30 diagnostic states of each parameter determined over the past 30 days as input to the probability model 19. In another example, processing circuitry 98 may determine the probability score at a predefined time interval each day using the previous 15 diagnostic states of each parameter determined over the past 15 days as input to the probability model 19. In any event, processing circuitry 98 may receive data from medical device(s) 17 on a periodic basis, such as on a daily, weekly, or biweekly basis, etc. In such examples, processing circuitry 98 may determine the probability score upon receiving the data from medical device(s) 17 according to the periodic transmission rate of medical device(s) 17 (e.g., daily, weekly, biweekly, etc.). That is, in one example, processing circuitry 98 may determine diagnostic states (e.g., risk states) for each physiological parameter. In such examples, processing circuitry 98 may combine the last X number of days of diagnostic states together to determine a probability score using probability model 19.

In another example, processing circuitry 98 may determine the probability score (e.g., risk score) and diagnostic states on a periodic basis. In addition, processing circuitry 98 may determine the status of the health condition of patient 4 using the probability score and a threshold on a periodic basis. In a non-limiting example, processing circuitry 98 may compute the probability score, diagnostic states, and status on a daily basis. In such examples, processing circuitry 98 may store the probability score and/or diagnostic state for the last X number of days, such as for the last 30 days. In some examples, processing circuitry 98 may determine the probability score on a day basis using diagnostic data from the past X number of days, such as the last 30 days. In such examples, processing circuitry 98 may determine, on any given day, that the probability score satisfies a threshold. For example, processing circuitry 98 may determine that the probability score exceeds a threshold. In such examples where processing circuitry 98 determines that probability score satisfies a threshold, processing circuitry 98 may transmit an alert externally, such as to a physician device or patient device.

Although described with reference to processing circuitry 98, the techniques of this disclosure are not so limited. In some examples, other processing circuitry (e.g., processing circuitry 80, processing circuitry 50, or processing circuitry of another one of medical device(s) 17, such as a CPU of one of medical device(s) 17) may perform one or more of the techniques of this disclosure and may coordinate with other devices accordingly. For example, processing circuitry of one of medical device(s) 17 may determine the probability score on a daily basis, compare the probability score to a threshold, and cause the transmission of an alert where the probability score satisfies the threshold. In such examples, a particular medical device from one of medical device(s) 17 may receive data (e.g., diagnostic data) from network 92, such as from other medical device(s) 17, external device 12, or data server(s) 94, and may determine the probability score using processing circuitry included with the particular medical device.

In examples where storage device 96 does not have data corresponding to a particular timeframe, processing circuitry 98 may extrapolate data or interpolate data or in some examples, processing circuitry 98 may determine an extent to which the data for a physiological parameter is missing and determine whether to use the physiological parameter when determining the probability score, as discussed herein.

In another example, processing circuitry 98 may determine the probability score based on determined values of the physiological parameters that correspond to a preceding timeframe relative to when the probability score is determined. For example, processing circuitry 98 may identify diagnostic states based on physiological parameter values determined during a preceding timeframe prior to determining the probability score. In one example, the preceding timeframe may be approximately 30 days relative to when the probability score is determined. In some examples, the preceding timeframe and the predetermined amount of time may include the same amount of time relative to when the probability score is determined. For example, where the predetermined amount of time is 30 days in the future, the preceding timeframe may be 30 days of past data, and where the predetermined amount of time is 29 days in the future, the preceding timeframe may be 29 days in the past.

In some examples, the amount of time for each of the predetermined amount of time and the preceding timeframe may be different based on the number of days in each month. For example, processing circuitry 98 may determine a probability score on the last day of each month and for convenience, may forecast for the next month based on the physiological parameters determined for the preceding month, in which case the predetermined amount of time and the preceding timeframe may include a different amount of time. In other examples, the amount of time for each may remain constant regardless of convenience factors (e.g., 60 days on either end, or 30 days for the predetermined amount of time in the future and 45 days for the preceding timeframe).

In some examples, the amount of time for the preceding timeframe may be dependent on values associated with the physiological parameters. For example, processing circuitry 98 may determine diagnostic states for subcutaneous tissue impedance scores on a 30-day preceding timeframe basis, whereas processing circuitry 98 may determine diagnostic states for respiration rate on a shorter or longer preceding timeframe basis. In such examples, processing circuitry 98 may use a plurality of preceding timeframes for various physiological parameters. In other examples, processing circuitry 98 may use a common preceding timeframe regardless of any resolution parameters used to determine the physiological parameter values (e.g., impedance scores, NHR, etc.), where resolution parameters may include filters, time constraints, or activity determinations.

With reference still to FIG. 4, processing circuitry 98 is configured to identify, from the respective one or more values for each physiological parameter, a plurality of physiological parameter features that encode amplitude, out-of-normal range values, and temporal changes. In the example of amplitude, a physiological parameter feature may encode R-wave amplitudes, accelerometer signal amplitudes, etc. For example, processing circuitry 98 may determine whether a particular physiological parameter satisfies an absolute threshold. In an illustrative example, processing circuitry 98 may determine whether an average NHR of patient 4 is greater than a predefined threshold of 90 bpm. In the example of out-of-range values, a physiological parameter feature may encode use range values to determine whether a physiological parameter includes out-of-range values to encode. For example, processing circuitry 98 may determine a high heart rate based on expected heart rate values.

In an illustrative example, processing circuitry 98 may determine NHR out-of-range values by comparing the average NHR to determine how many data NHR has been greater than 90 bpm or less than 55 bpm. In the example of temporal changes, a physiological parameter feature may encode changes in a physiological parameter over time. In one example, processing circuitry 98 may encode a feature of subcutaneous impedance measurements with changes in impedance over a period of days or weeks. Similar to calculating the fluid index using impedance values, processing circuitry 98 may determine relative changes in a physiological parameter value to determine temporal changes, rather than absolute changes. In an illustrative example, processing circuitry 98 may determine whether an average or current-day NHR value has increased in a sustained manner over the last 7 days or 30 days relative to NHR values in the last 7 days or 30 days.

In such examples, processing circuitry 98 is configured to identify the evidence nodes based at least in part on the plurality of physiological parameter features. For example, processing circuitry 98 may extract features that encode information regarding out-of-normal range values, as well as temporal changes at weekly and monthly time scale for the physiological parameters. In a non-limiting example, processing circuitry 98 may determine diagnostic categories based on a combination of features, such that the HFH rates increase from one category to the next. For example, the category with the largest number of HFH rates may be designed to have the lowest occurrence rate through the feature extraction process.

In some examples, processing circuitry 98 is configured to identify a plurality of physiological parameter features based on the respective one or more values for each physiological parameter. The physiological parameter features are configured to, upon analysis, yield a same number of potential diagnostic states for each physiological parameter. In some examples, the same number of potential diagnostic states may be three potential diagnostic states (e.g., H, M, and L). In other examples, one or more physiological parameters may have a different number of potential diagnostic states, such as one or two potential diagnostic states. For example, AF may have two diagnostic states of high and low. In such examples, processing circuitry 98 is configured to identify, from the potential diagnostic states, the diagnostic state for each of the physiological parameters.

Processing circuitry 98 may extract features from the physiological parameters and/or from the physiological parameter values. For example, processing circuitry 98 may analyze a large set of time series data for each physiological parameter for time windows including the number of days the values are outside a normal amplitude range, cumulative sum of difference between the raw measurement and an adaptive reference (CSAR), cumulative sum of difference between the raw measurement in a fixed reference (CSFR), number of days CSAR or CSFR were above a threshold, slope or rate of change of raw measurement values, or mean, median, minimum, and maximum measurement values. Processing circuitry 80 may extract such features for each physiological parameter to encode amplitude and temporal characteristics with respect to particular temporal scales.

In some examples, processing circuitry 98 may determine a MVN as one of the evidence nodes. For instance, multiple physiological parameters may factor into determining a single child node of evidence nodes 8. In a non-limiting example, processing circuitry 98 is configured to determine an input to a first child node of evidence nodes 8 based on a combination of one or more values. For example, one evidence node may be based on a combination of an indication of atrial fibrillation (AF) extent in patient 4 during a time period and one or more values indicating a ventricular rate during the time period (e.g., during AF). In addition, processing circuitry 98 may be configured to determine an input to a second child node of the plurality of evidence nodes based on the respective one or more values of the one or more subcutaneous tissue impedance parameters. In such instances, evidence node 8A may include a combination of an AF extent indication value(s) and ventricular rate value (s), whereas evidence node 8A may indicate one or more subcutaneous tissue impedance parameter values (e.g., subcutaneous tissue impedance score, fluid indices, etc.).

With reference still to FIG. 4, processing circuitry 98 may determine, for each of the plurality of physiological parameters or evidence nodes 8, the respective one or more parameter values at various frequencies. For example, processing circuitry 98 may determine the values for evidence node 8A at a different frequency than for evidence node 8B. Thus, diagnostic states 11 may update at different frequencies. In such examples, processing circuitry 98 may delay execution of probability model 19 until an appropriate number of diagnostic states are deemed current or updated. In any event, processing circuitry 80 may determine the diagnostic states using the respective one or more values. Processing circuitry 98 may use the diagnostic states to determine posterior probability 25. Processing circuitry 98 may then store, the respective one or more values and/or the probability score to, as examples, storage device 96, storage device 84, and/or storage device 56 of medical device(s) 17 (e.g., IMD 10).

Figure 5:
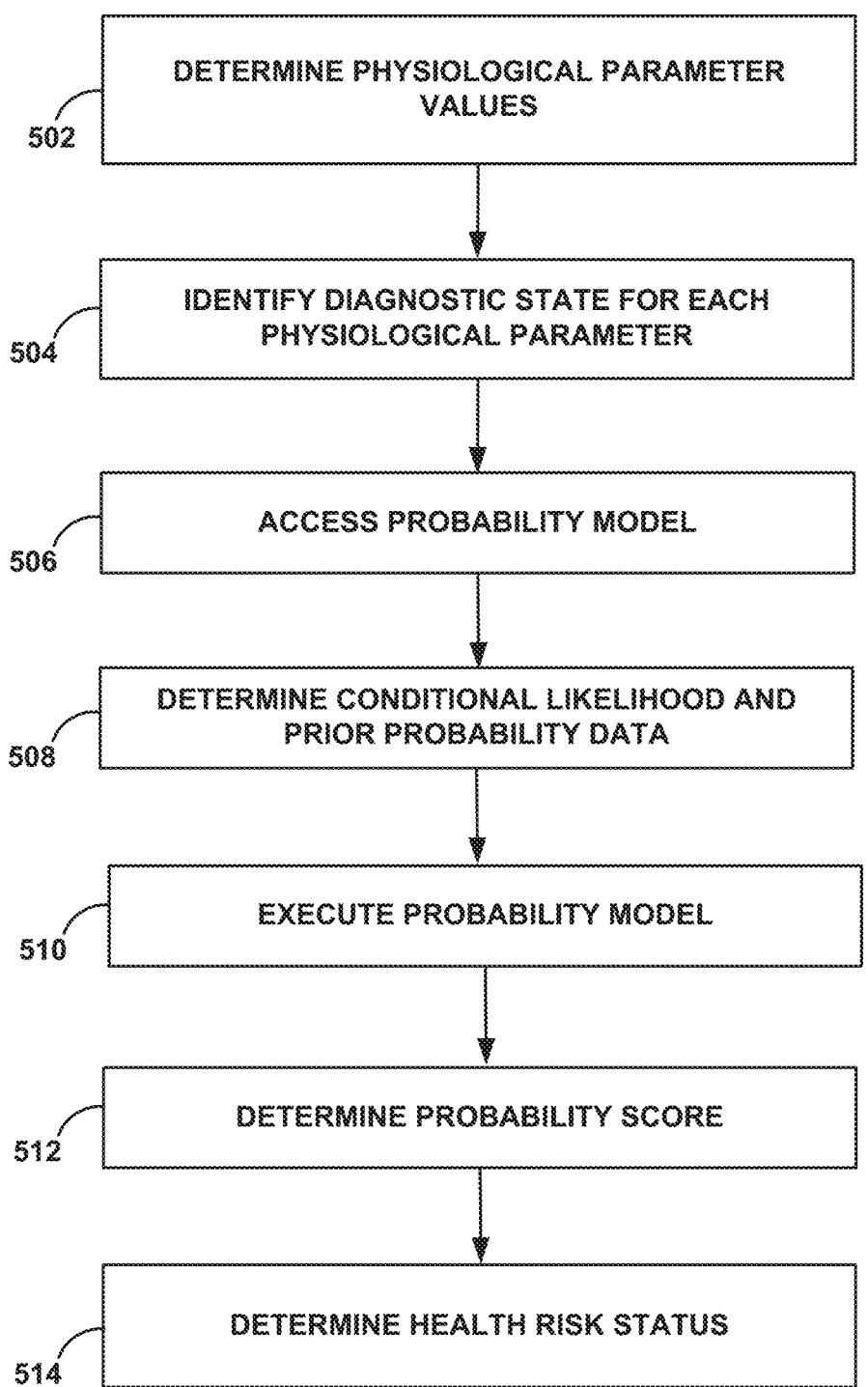
FIG. 5 is a flow diagram illustrating an example method that may be performed by one or more medical devices (e.g., IMDs) and/or a computing device, in conjunction with probability model 19 of FIGS. 2-4, to determine a probability score with respect to the patient, in accordance with one or more techniques disclosed herein.

Turning now to FIG. 5, FIG. 5 illustrates an example method that may be performed by one or more of medical devices 17, external device 12, and/or data server(s) 94 in conjunction with probability model 19 described with reference to FIGS. 2-4, to determine a probability score with respect to the patient, in accordance with one or more techniques disclosed herein. Although described as being performed by data server(s) 94, one or more of the various example techniques described with reference to FIG. 5 may be performed by any one or more of IMD 10, external device 12, or data server(s) 94, e.g., by the processing circuitry of any one or more of these devices.

In some examples, processing circuitry, e.g., processing circuitry 50 of IMD 10, processing circuitry 80 of external device 12, or processing circuitry 98 of data server(s) 94, may determine values of physiological parameters, such as those physiological parameters described herein (502). For each of the physiological parameters, processing circuitry 98 may identify diagnostic states 11 (504). In some instances, processing circuitry 98 may filter irrelevant physiological parameters or parameter values prior to identifying diagnostic states or after identifying diagnostic states. For example, certain physiological parameters or values thereof may not be relevant to the purpose of deploying probability model 19. In such instances, those physiological parameters or values may still be available to processing circuitry 80, but processing circuitry 98 may determine those parameters should not be used as evidence nodes 8. At any point in time, processing circuitry 98 may access probability model 19 (506). For example, processing circuitry 98 may access probability model 19 stored in storage device 96.

In some examples, processing circuitry 98 may determine conditional likelihood and prior probability data (508). For example, processing circuitry 98 may determine conditional likelihood and prior probability data in accordance with the techniques described in U.S. application Ser. No. 13/391, 376 by Sarkar et al., entitled "METHOD AND APPARATUS FOR MONITORING TISSUE FLUID CONTENT FOR USE IN AN IMPLANTABLE CARDIAC DEVICE," filed on Feb. 20, 2012, and incorporated herein by reference in its entirety. For example, the conditional likelihood parameters may take the form of conditional likelihood tables defined for each diagnostic state for each physiological parameter. The posterior probability may then be tabulated for all possible combinations of diagnostic states to determine a posterior probability, or in some instances, a probability table, as described in U.S. application Ser. No. 13/391,376.

In some examples, processing circuitry 98, or other processing circuitry, may have previously used prior probability value(s) 21 and conditional likelihood 23, e.g., based on prior data of one or more subjects, to create probability model 19. For example, probability model 19 may include a look-up table (LUT) that the processing circuitry generated using prior probability value(s) 21 and conditional likelihood 23. That is, probability value(s) 21 and conditional likelihood 23 may be used to create probability model 19 but not to determine posterior probability 25 for a given patient.

Processing circuitry 98 may then execute probability model 19 (510). Processing circuitry 98 may execute probability model 19 in response to a user command or may do so automatically in response to a triggering event. For example, processing circuitry 98 may determine that all necessary diagnostic states have been determined and that the probability model 19 is ready for execution. In some examples, processing circuitry 98 may receive data for various physiological parameters or processing circuitry 98 may access data from storage device 96. Processing circuitry 98 may determine the diagnostic state (L/M/H) for each parameter. For the particular set of physiological parameters used (e.g., parameters having sufficient data), processing circuitry 98 may use the diagnostic states to map to a particular row of the LUT. Processing circuitry 98 may identify the posterior probability 25 that is mapped to the particular row. Processing circuitry 98 may subsequently utilize the data that was used to determine the posterior probability 25 to train the probability model 19 for future rounds of determining probability scores. For example, processing circuitry 98 may use the current or incoming data to determine the prior probability value(s) 21.

In some examples, processing circuitry 98 may execute probability model a number of times in a finite period of time in order to determine an average probability score for the finite period of time. In some instances, processing circuitry 98 may execute probability model in accordance with a Monte Carlo simulation (e.g., using repeated random sampling to obtain numerical results).

As such, processing circuitry 98 may determine one or more probability scores from probability model 19 (512). Processing circuitry 98 may use evidence nodes 8 as input to probability model 19 to determine a posterior probability score that indicates a likelihood that a patient will experience an adverse health event within a predetermine period of time (e.g., within 30 days of determining the probability score). As discussed herein, the probability model may use the prior probability value and a conditional likelihood parameter as additional inputs to determine the posterior probability score. The probability score (p-value) may be represented as a decimal value. In some examples, processing circuitry may then update the probability model using the determined posterior probability score. In some examples, a Bayesian ML model may determine the probability score, where the ML model may be trained on prior probability values and feedback received regarding the accuracy of the probability score in predicting adverse health events.

As discussed in more detail with reference to FIG. 10, processing circuitry 98 may compare the probability score to at least one risk threshold. Based on the comparison, processing circuitry 98 may determine one of plurality of discrete risk categorizations. For example, discrete risk categorizations may be high risk, low risk, or medium risk. Although described as being performed by server 94, one or more of the various example techniques described with reference to FIG. 5 may be performed by any one or more of IMD 10, external device 12, or server 94, e.g., by the processing circuitry of any one or more of these devices. In this way, processing circuitry 98 may determine a health risk status for a patient based at least in part on the probability score (514). In an example, processing circuitry 98 may be configured to monitor a patient, for example, with heart failure for a developing heart failure decompensation in accordance with one or more of the various techniques disclosed herein to then allow for early intervention potentially before clinical symptoms are experienced or hospitalization is needed. In another example, through implementation of the disclosed probability model (e.g., a Bayesian model), processing circuitry 98 may combine information from multiple "orthogonal" parameters, that alone may not be very specific, to ultimately gain a more specific classification.

It should be noted that one or more of the various example techniques described with reference to FIG. 5 may be performed on a periodic basis. For example, the probability score may be determined according to a resolution parameter setting of medical device(s) 17 and/or for patient 4. In other examples, the probability score may be calculated irrespective of the resolution parameter. Data server(s) 94 may calculate the probability score once a day, each week, every two weeks, each month, etc. In some examples, data server(s) 94 may also calculate the probability score in response to a user command (e.g., from a physician, from a user interface) or in response to a satisfaction of another condition, such as upon receiving or determining a particular number of diagnostic states, or an indication of a change in the condition of patient from a source other than the application of the probability model.

Data server(s) 94 may also trigger a probability score determination when an activity level or other physiological parameter of patient 4 satisfies a threshold (e.g., low activity when patient 4 is resting or sleeping). In one other example, data server(s) 94 or medical device 17, e.g., IMD 10, may determine the probability score of patient 4 on a per measurement basis, such as on a per impedance score determination basis. A person of skill in the art would appreciate that various periods may exist for when IMD 10 or external device 12 may determine a probability score in accordance with FIG. 5, transmit a probability score, etc. In some examples, data server(s) 94 may determine the probability score of patient 4 in response to receipt of physiological parameter data for patient via network 92, e.g., from medical device(s) 17.

In addition, although described in terms of data server(s) 94 performing one or more of the various example techniques of this disclosure, it is to be understood that any number of different components described with reference to, for example, FIGS. 4, 5, 7, and 8, and combinations thereof, may perform one or more of the various example techniques of this disclosure. For example, IMD 10 or external device 12 may determine diagnostic states 11 or physiological parameter values. In addition, data server(s) 94 may include multiple computing devices (e.g., a remote cloud server) that collectively determines probability scores of patient 4 experiencing an adverse health event within a predetermined period of time. In addition, it is to be understood that the example components described with reference to FIGS. 4, 5, 7, and 8 may perform some or all of the example techniques described with reference to FIGS. 4, 5, and 10 in parallel or in conjunction with one another.

Figure 6A:
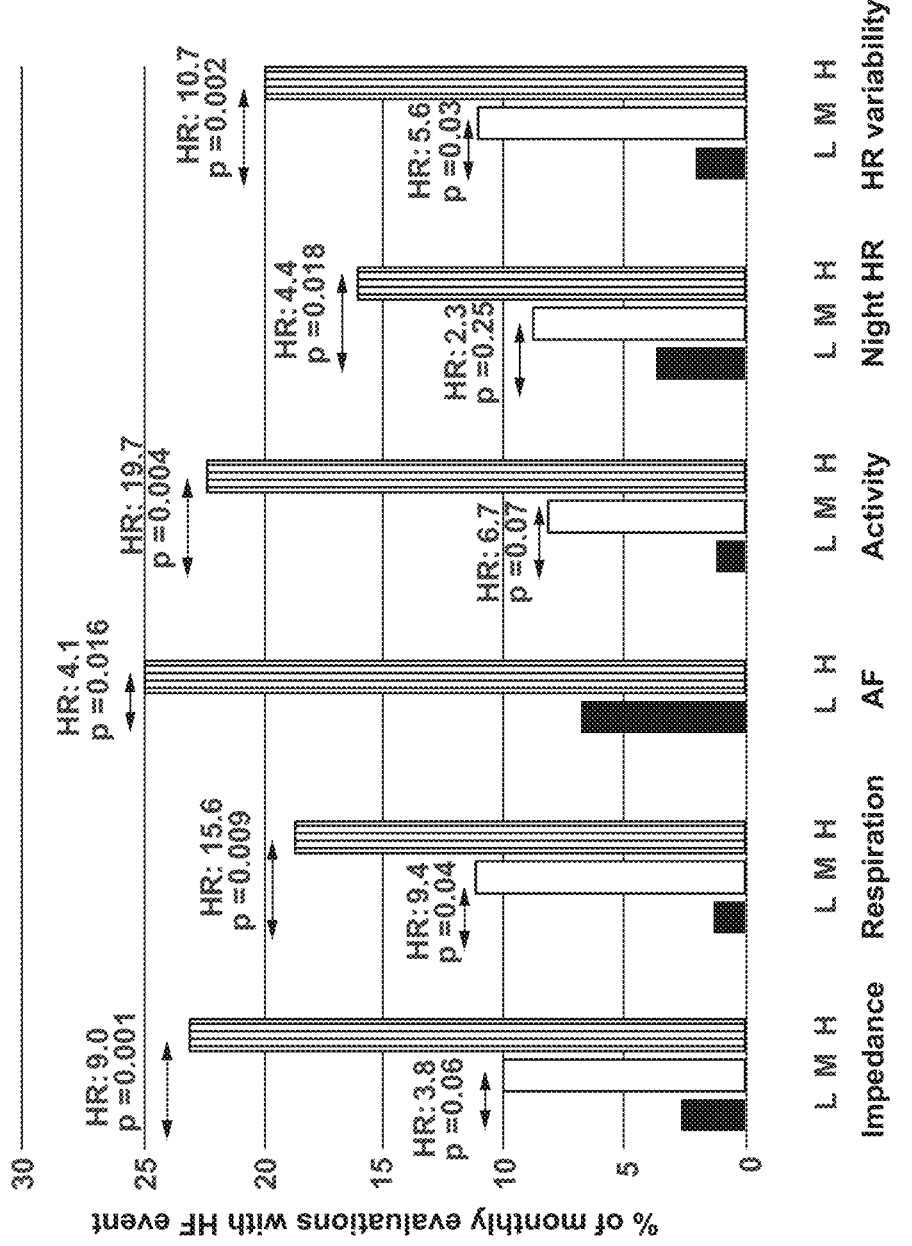
FIG. 6A illustrates a chart of individual physiological parameters that may serve as evidence nodes to the probability model of FIG. 4.
Figure 6B:
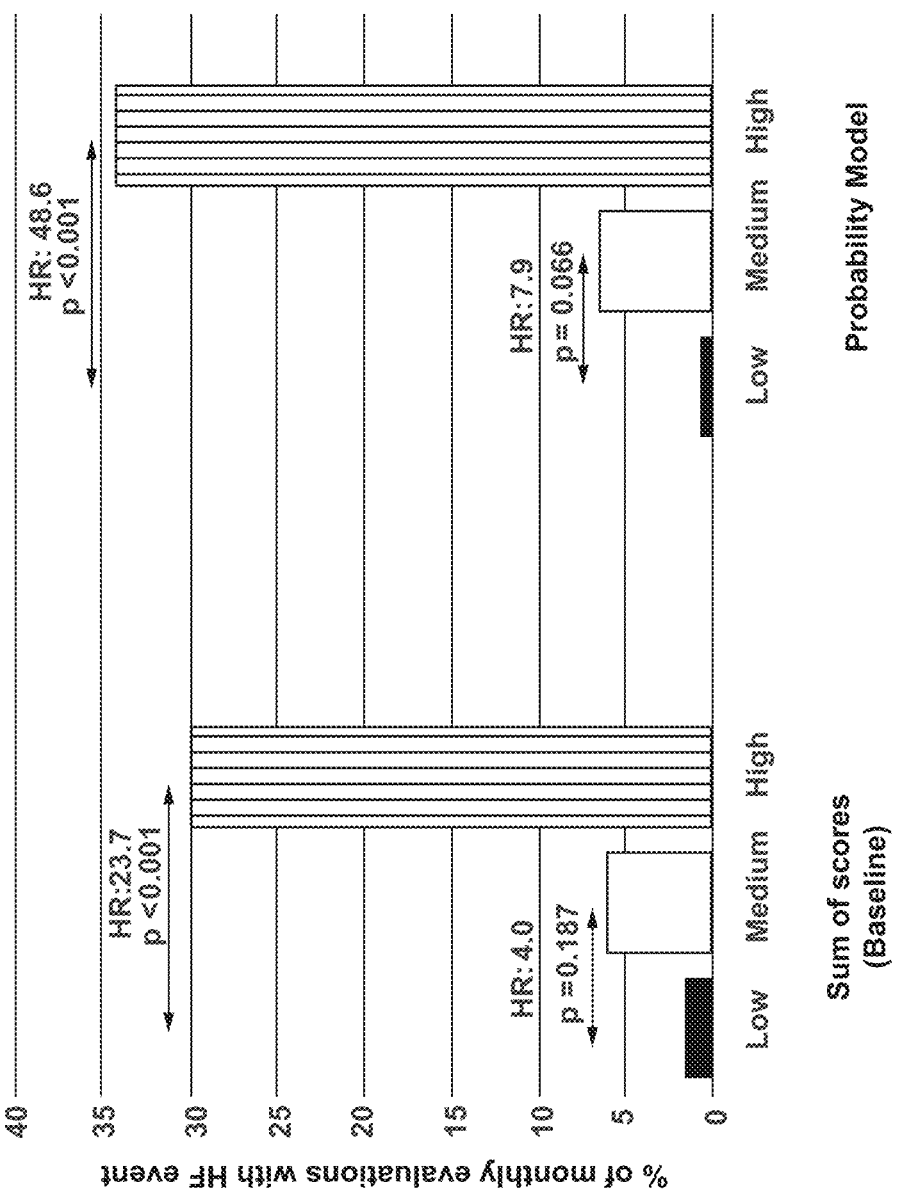
FIG. 6B illustrates a sum of individual probability scores of FIG. 6A on the left and a chart of combined probability scores using a probability model based on various evidence nodes of FIG. 4 on the right.

FIG. 6A illustrates a chart of individual physiological parameters that may serve as evidence nodes to the example probability model described with reference to FIG. 4. Each physiological parameter is independent of one another meaning processing circuitry 98 could identify from each individual parameter a risk level for patient 4. However, the accuracy would be less than when using probability model 19 as illustrated in FIG. 6B and Table 2 below. The values for each physiological parameter from FIG. 6A are illustrated in Table 1 below.

patient with a high diagnostic evidence score at a follow-up is 48 times more likely to be have an HF event in the next 30 days compared to patients with a low diagnostic evidence score at a follow-up.

TABLE 2

| Physiological parameter | # evaluations (% of total of 225 evals) | #HF hosp (% of evals in each risk group) | Hazard Ratio (HR) | prob-value ("p-value") |
|---|---|---|---|---|
| Impedance |  |  |  | 0.006 |
| 0 (L) | 107 (47.6%) | 3 (2.8%) | Reference |  |
| 1 (M) | 79 (35.1%) | 8 (10.1%) | 3.84 (0.94-15.62) | 0.061 |
| 2 (H) | 39 (17.3%) | 9 (23.1%) | 9.00 (2.34-34.70) | 0.001 |
| Respiration |  |  |  | 0.029 |
| 0 | 78 (34.7%) | 1 (1.3%) | Reference |  |
| 1 | 115 (51.1%) | 13 (11.3%) | 9.39 (1.12-78.60) | 0.039 |
| 2 | 32 (14.2%) | 6 (18.8%) | 15.55 (1.97-122.63) | 0.009 |
| AF |  |  |  | 0.016 |
| 0 | 201 (89.3%) | 14 (7.0%) | Reference |  |
| 2 | 24 (10.7%) | 6 (25.0%) | 4.08 (1.30-12.79) |  |
| Activity |  |  |  | 0.004 |
| 0 | 79 (35.1%) | 1 (1.3%) | Reference |  |
| 1 | 97 (43.1%) | 8 (8.2%) | 6.74 (0.87-52.03) | 0.067 |
| 2 | 49 (21.8%) | 11 (22.4%) | 19.65 (2.55-151.46) | 0.004 |
| NHR |  |  |  | 0.057 |
| 0 | 78 (34.7%) | 3 (3.8%) | Reference |  |
| 1 | 91 (40.4%) | 8 (8.8%) | 2.33 (0.55-9.78) | 0.248 |
| 2 | 56 (24.9%) | 9 (16.1%) | 4.40 (1.29-15.02) | 0.018 |
| HRV |  |  |  | 0.010 |
| 0 | 96 (42.7%) | 2 (2.1%) | Reference |  |
| 1 | 89 (39.6%) | 10 (11.2%) | 5.59 (1.23-25.37) | 0.026 |
| 2 | 40 (17.8%) | 8 (20.0%) | 10.67 (2.32-49.06) | 0.002 |

FIG. 6B illustrates a sum of individual probability scores from FIG. 6A on the left and a chart of combined probability scores using a probability model based on various evidence nodes of FIG. 4 on the right. For example, FIG. 6B illustrates the advantage of using probability model 19 to model the risk stratification performance for an integrated set of diagnostic states. In the example of FIG. 6B, a Bayesian approach was used to model the probability score shown on the right and an unweighted sum of individual diagnostic states(e.g., PARTNERS-HF or sum of scores) was used on the left. In a non-limiting example, sample results may be summarized in a Table 3 as follows showing a Bayesian approach in comparison to a "sum of scores" approach.

TABLE 3

| | # evaluations | #HF hosp (% of evals) | Hazard Ratio (HR) | prob-value ("p-value") |
|---|---|---|---|---|
| Sum of scores |  |  |  | <0.001 |
| 0-4 | 137 (60.9%) | 2 (1.5%) | Reference |  |
| 5 | 34 (15.1%) | 2 (5.9%) | 4.01 (0.51-31.59) | 0.187 |
| 6-12 | 54 (24.0%) | 16 (29.6%) | 23.72 (5.15-109.24) | <0.001 |
| Posterior probability |  |  |  | <0.001 |
| <1.1% | 119 (59.9%) | 1 (0.8%) | Reference |  |
| 1.1%-10% | 62 (27.6%) | 4 (6.5%) | 7.86 (0.87-70.99) | 0.066 |
| >10% | 44 (19.6%) | 15 (34.1%) | 48.61 (6.5-363.51) | <0.001 |

Figure 7:
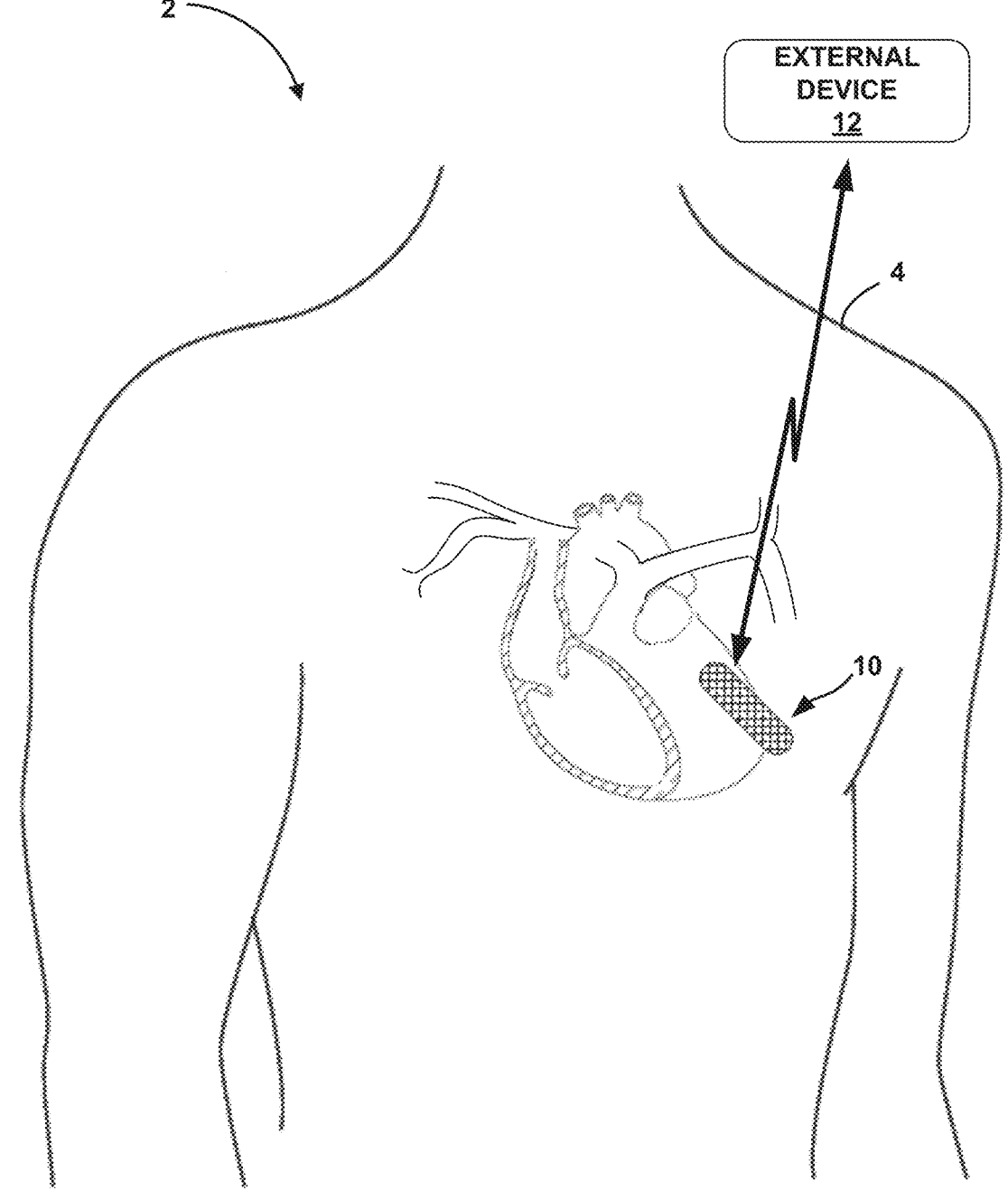
FIG. 7 illustrates the environment of an example medical system in conjunction with the patient, including an example implantable medical device (IMD) used to determine physiological parameters of the patient.

Due to the dynamic nature of the probability score the same patient may have very high evidence at one follow-up and low evidence at another follow-up. The high diagnostic evidence group consisted of evaluations with around the top 20% of risk scores. The combined low evidence group consisted of cases where each or multiple of the diagnostic parameters had low evidence. The results indicate that a FIG. 7 illustrates the environment of an example medical system 2 in conjunction with a patient 4, in accordance with one or more techniques of this disclosure. Patient 4 ordinarily, but not necessarily, will be a human. For example, patient 4 may be an animal needing ongoing monitoring for cardiac conditions.

In some examples, system 2 may include IMD 10. In other examples, system 2 may not include IMD 10 and may instead include other medical device(s) 17 (not shown in FIG. 7). IMD 10 may include one or more electrodes (not shown) on its housing, or may be coupled to one or more leads that carry one or more electrodes. System 2 may also include external device 12 and, although not depicted in FIG. 7, the various other devices illustrated in one or more of the various example techniques described with reference to FIG. 2. Example system 2 may be used to measure subcutaneous impedance to provide to patient 4 other users an early warning for the onset of a heart failure decompensation event.

The example techniques may be used with an IMD 10, which may be in wireless communication with at least one of external device 12 or data server(s) 94. In some examples, IMD 10 is implanted outside of a thoracic cavity of patient 4 (e.g., subcutaneously in the pectoral location illustrated in FIG. 7). IMD 10 may be positioned near the sternum near or just below the level of the heart of patient 4, e.g., at least partially within the cardiac silhouette. IMD 10 may include a plurality of electrodes and may be configured for subcutaneous implantation outside of a thorax of patient 4.

Figure 8:
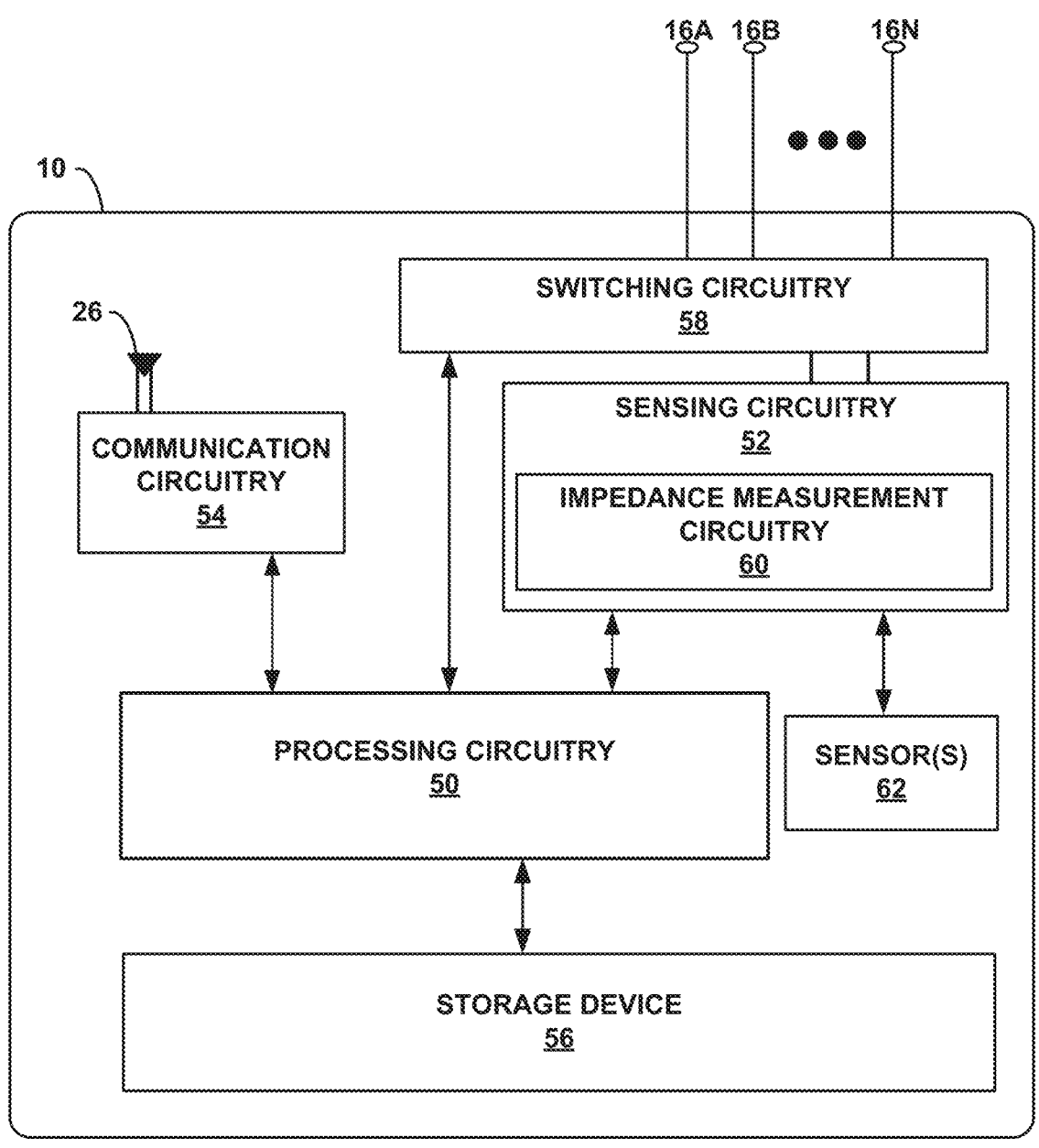
FIG. 8 is a functional block diagram illustrating an example configuration of an IMD of FIG. 7.
Figure 9:
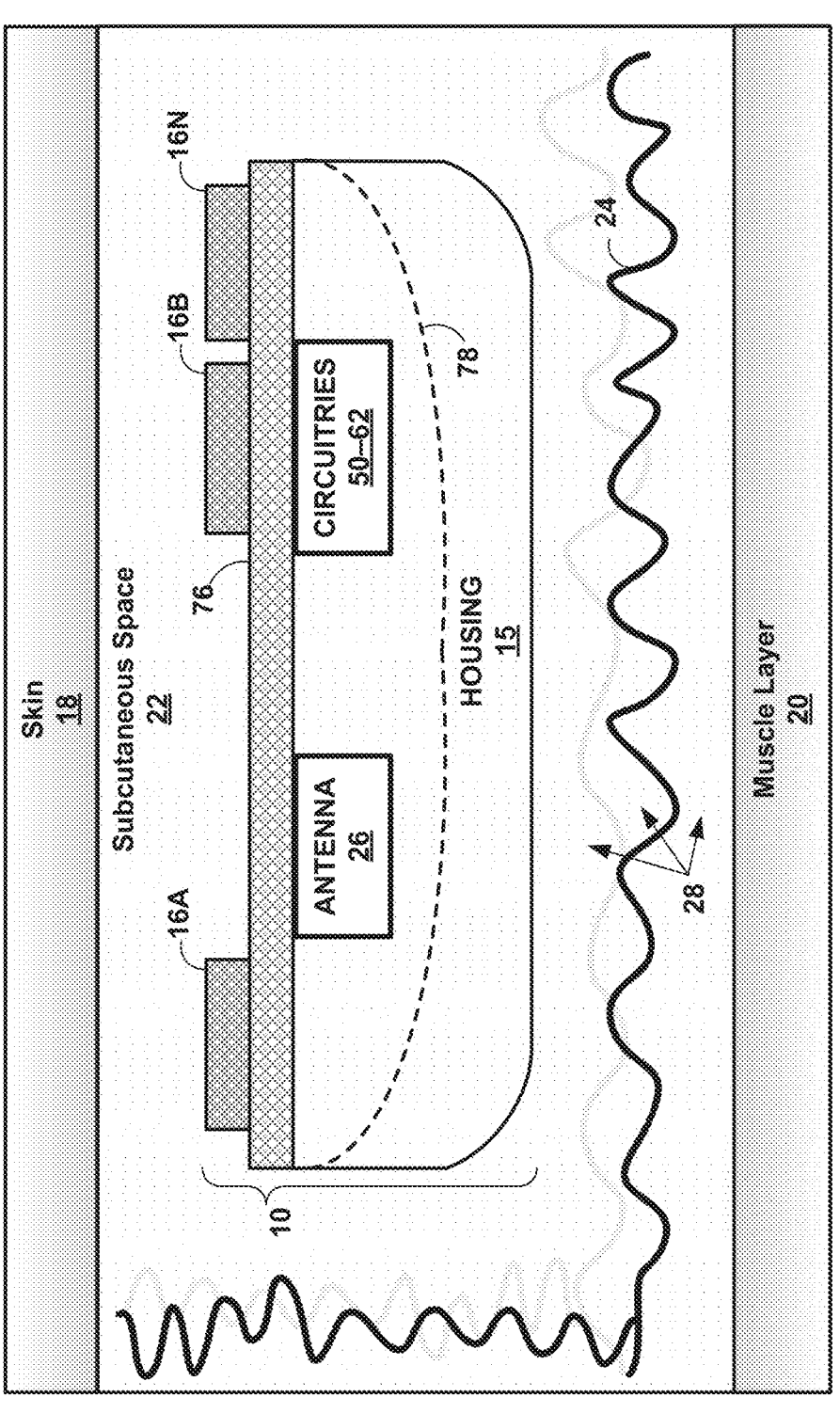
FIG. 9 is a conceptual side-view diagram illustrating an example IMD of the medical system of FIGS. 7 and 8 in greater detail.

Accordingly, impedance measurements taken via electrodes in the subcutaneous space, e.g., electrodes on a subcutaneously implanted medical device as shown in FIGS. 7-9, may be measurements of the impedance of interstitial fluid and subcutaneous tissue. In an example, during a heart failure decompensation event, reduction in cardiac output can tend to increase venous pressure. An increase in venous pressure tends to lead to an increase in pressure with respect to capillaries compared to the interstitial space. The combination of such tendencies may then lead to a net outflow of fluid from the capillaries into the interstitium or interstitial space of a patient. In such instances, the interstitium will have an increase in fluid accumulation. An increase in fluid accumulation tends to provide a reduction in impedance measured between electrodes.

Implantable medical devices (IMDs) can sense and monitor impedance signals and use those signals to determine a health condition status of a patient or other health condition status of a patient (e.g., edema, preeclampsia, hypertension, etc.). The electrodes used by IMDs to sense impedance signals are typically integrated with a housing of the IMD and/or coupled to the IMD via one or more elongated leads. Example IMDs that include electrodes include the Reveal LINQ™ Insertable Cardiac Monitor (ICM), developed by Medtronic, Inc., of Minneapolis, MN, which may be inserted subcutaneously. Other example IMDs may include electrodes on a subcutaneous lead connected to another one of medical device(s) 17, such as a subcutaneous implantable cardioverter-defibrillator (ICD) or an extravascular ICD. Such IMDs may facilitate relatively longer-term monitoring of patients during normal daily activities and may periodically transmit collected data to a network service, such as the Medtronic CareLink® Network.

Medical devices configured to measure impedance via implanted electrodes, including the examples identified herein, may implement the techniques of this disclosure for measuring impedance changes in the interstitial fluid of a patient to determine whether the patient is experiencing worsening heart failure or decompensation. The techniques include evaluation of the impedance values using criteria configured to provide a desired sensitivity and specificity of heart failure detection. The techniques of this disclosure for identifying heart failure worsening may facilitate determinations of cardiac wellness and risk of sudden cardiac death and may lead to clinical interventions to suppress heart failure worsening, such as with medications.

As such, IMD 10 may be configured to measure, in some cases among other physiological parameter values, impedance values within the interstitial fluid of patient 4. For example, IMD 10 may be configured to receive one or more signals indicative of subcutaneous tissue impedance from electrodes 16. In some examples, IMD 10 may be a purely diagnostic device. For example, IMD 10 may be a device that only determines subcutaneous impedance parameters of patient 4, or a device that determines subcutaneous impedance parameters as well as other physiological parameter values of patient 4. IMD 10 may use the impedance value measurements to determine one or more fluid index values, impedance scores, and/or various thresholds, such as adaptive thresholds, scoring thresholds, weighting factors for thresholds, and/or cardiac risk thresholds.

Subcutaneous impedance may be measured by delivering a signal through an electrical path between electrodes. In some examples, the housing of IMD 10 may be used as an electrode in combination with electrodes located on leads. For example, system 2 may measure subcutaneous impedance by creating an electrical path between a lead and one of the electrodes. In additional examples, system 2 may include an additional lead or lead segment having one or more electrodes positioned subcutaneously or within the subcutaneous layer for measuring subcutaneous impedance. In some examples, two or more electrodes usable for measuring subcutaneous impedance may be formed on or integral with the housing of IMD 10.

System 2 measures subcutaneous impedance of patient 4 and processes impedance data to accumulate evidence of decreasing impedance. The accumulated evidence is referred to as a fluid index and may be determined as function of the difference between measured impedance values and reference impedance values. The fluid index may then be used to determine impedance scores that are indicative of a heart condition of patient 4. In an example, an impedance score may be measured against a risk threshold that identifies diagnostic states of the subcutaneous tissue impedance physiological parameters, which may be applied to probability model 19 as described herein. In some examples, subcutaneous impedance may provide information about fluid volume in the subcutaneous space (e.g., subcutaneous space 22 of FIG. 9), and in some instances, total blood volume, as well. In such examples, subcutaneous impedance measurements allow system 2 via probably model 19 to identify patients that have accumulated threshold levels of peripheral fluid as determined based on a plurality of evidence nodes, where at least one evidence node is based at least in part on a subcutaneous impedance measurement or subcutaneous impedance score.

In some examples, IMD 10 may also sense cardiac electrogram (EGM) signals via the plurality of electrodes and/or operate as a therapy delivery device. For example, IMD 10 may additionally operate as a therapy delivery device to deliver electrical signals to the heart of patient 4, such as an implantable pacemaker, a cardioverter, and/or defibrillator, a drug delivery device that delivers therapeutic substances to patient 4 via one or more catheters, or as a combination therapy device that delivers both electrical signals and therapeutic substances.

In some examples, system 2 may include any suitable number of leads coupled to IMD 10, and each of the leads may extend to any location within or proximate to a heart or in the chest of patient 4. For example, other examples therapy systems may include three transvenous leads and an additional lead located within or proximate to a left atrium of a heart. As other examples, a therapy system may include a single lead that extends from IMD 10 into a right atrium or right ventricle, or two leads that extend into a respective one of a right ventricle and a right atrium.

In some examples, IMD 10 may be implanted subcutaneously in patient 4. Furthermore, in some examples, external device 12 may monitor subcutaneous impedance values. In some examples, IMD 10 takes the form of the Reveal LINQ™ ICM, or another ICM similar to, e.g., a version or modification of, the LINQ™ ICM, which may be inserted subcutaneously. Such IMDs may facilitate relatively longer-term monitoring of patients during normal daily activities, and may periodically transmit collected data to a network service, such as the Medtronic CareLink® Network.

Although described in the context of examples in which IMD 10 includes an insertable or implantable IMD, example systems including one or more external devices of any type configured to sense subcutaneous tissue impedances may be configured to implement the techniques of this disclosure. In some examples, IMD 10 may be a device configured to measure impedances of a fluid and shifts in impedances of the fluid, such as interstitial fluid. For example, IMD 10 may have one or more electrodes disposed within one layer of patient 4 (e.g., subcutaneous layer), whereas at least one other electrode may be disposed within another layer of patient 4 (e.g., dermis layer, muscle layer, etc.). In such examples, IMD 10 may be able to measure impedances and shifts in impedances of the interstitial fluid of the subcutaneous layer. In another example, IMD 10 may be a cutaneous patch device having electrodes on the outside of the skin. In such examples, IMD 10 may use the cutaneous patch device to measure impedances and shifts in impedances of the interstitial fluid in the subcutaneous layer.

In examples in which IMD 10 also operates as a pacemaker, a cardioverter, and/or defibrillator, or otherwise monitors the electrical activity of the heart, IMD 10 may sense electrical signals attendant to the depolarization and repolarization of the heart of patient 4 via electrodes of or coupled to IMD 10, e.g., which may include the electrodes used to determine subcutaneous impedance. In some examples, IMD 10 can provide pacing pulses to the heart of patient 4 based on the electrical signals sensed within the heart of patient 4. The configurations of electrodes used by IMD 10 for sensing and pacing may be unipolar or bipolar. IMD 10 may also provide defibrillation therapy and/or cardioversion therapy via electrodes located on at least one lead, as well as a housing electrode. IMD 10 may detect tachyarrhythmia of the heart of patient 4, such as fibrillation of atria or ventricles, and deliver defibrillation or other tachyarrhythmia therapy to the heart of patient 4 in the form of electrical pulses. In some examples, IMD 10 may be programmed to deliver a progression of therapies, e.g., pulses with increasing energy levels, until a fibrillation of the heart of patient 4 is stopped. IMD 10 detects fibrillation or other tachyarrhythmias employing tachyarrhythmia detection techniques known in the art.

FIG. 8 is a functional block diagram illustrating an example configuration of IMD 10. IMD 10 may include an example of one of medical device(s) 17 described with reference to FIGS. 2-4. In the illustrated example, IMD 10 includes electrodes 16A-16N (collectively, "electrodes 16"), antenna 26, processing circuitry 50, sensing circuitry 52, impedance measurement circuitry 60, communication circuitry 54, storage device 56, switching circuitry 58, sensors 62. IMD 10, along with other medical device(s) 17, may also include a power source. In general, the power source may include a rechargeable or non-rechargeable battery. Each of medical device(s) 17 may include components common to those of IMD 10. For example, each of medical device(s) 17 may include processing circuitry 50. For sake of brevity, each configuration of each medical device(s) 17 will not be described in this application. That is, certain components of IMD 10 may serve as representative components of other medical device(s) 17 (e.g., storage device 56, communication circuitry 54, sensor(s) 62, etc.).

Processing circuitry 50 may include fixed function circuitry and/or programmable processing circuitry. Processing circuitry 50 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof.

Sensing circuitry 52 may be selectively coupled to electrodes 16 via switching circuitry 58, e.g., to select the electrodes 16 and polarity, referred to as the sensing vector, used to sense impedance and/or cardiac signals, as controlled by processing circuitry 50. Sensing circuitry 52 may sense signals from electrodes 16, e.g., to produce a cardiac EGM, in order to facilitate monitoring the electrical activity of the heart. Sensing circuitry 52 also may monitor signals from sensors 62, which may include one or more accelerometers, pressure sensors, and/or optical sensors, as examples. In some examples, sensing circuitry 52 may include one or more filters and amplifiers for filtering and amplifying signals received from electrodes 16 and/or sensors 62.

In some examples, processing circuitry 50 may use switching circuitry 58 to select, e.g., via a data/address bus, which of the available electrodes are to be used to obtain impedance measurements of interstitial fluid and to sense cardiac signals, and to select the polarities of the electrodes. Switching circuitry 58 may include a switch array, switch matrix, multiplexer, transistor array, microelectromechanical switches, or any other type of switching device suitable to selectively couple sensing circuitry 58 to selected electrodes. In some examples, sensing circuitry 52 includes one or more sensing channels, each of which may include an amplifier. In response to the signals from processing circuitry 50, switching circuitry 58 may couple the outputs from the selected electrodes to one of the sensing channels.

In some examples, one or more channels of sensing circuitry 52 may include one or more R-wave amplifiers that receive signals from electrodes 16. In some examples, the R-wave amplifiers may take the form of an automatic gain-controlled amplifier that provides an adjustable sensing threshold as a function of the measured R-wave amplitude. In addition, in some examples, one or more channels of sensing circuitry 52 may include a P-wave amplifier that receives signals from electrodes 16. Sensing circuitry may use the received signals for pacing and sensing in the heart of patient 4. In some examples, the P-wave amplifier may take the form of an automatic gain-controlled amplifier that provides an adjustable sensing threshold as a function of the measured P-wave amplitude. Other amplifiers may also be used.

In some examples, processing circuitry 50 may be configured to record an R-wave amplitude for an ECG sensed by sensing circuitry 52. For example, sensing circuitry 52 may be configured to sense a subcutaneous ECG, and processing circuitry 50 may be configured to record an R-wave amplitude of the subcutaneous ECG. In another example, sensing circuitry 52 may be configured to record cardiac electrogram using leads in the heart of patient 4 and as measured between the housing of one of medical device(s) 17 (e.g., a can) and the leads in the heart of patient 4, and processing circuitry 50 may be configured to record an R-wave amplitude of the cardiac electrogram. Similarly, sensing processing circuitry 50 may record a R-wave slopes or R-wave widths for an ECG or other cardiac electrogram.

In some examples, sensing circuitry 52 includes a channel that includes an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in storage device 56. In some examples, processing circuitry 50 may employ digital signal analysis techniques to characterize the digitized signals stored in storage device 56 to detect P-waves (e.g., within ventricular or far-field signals and instead of or in addition to use of P-wave amplifiers) and classify cardiac tachyarrhythmias from the digitized electrical signals.

Based on the detection R-waves and P-waves, e.g., their rates, processing circuitry 50 may identify atrial and ventricular tachyarrhythmias, such as AF or VF. Processing circuitry may employ digital signal analysis techniques to detect or confirm such tachyarrhythmias in some examples. Processing circuitry 50 may determine values of physiological parameters based on detection of such tachyarrhythmias, and a probability of a health event may be determined based on the physiological parameter values according to the techniques described herein. Example physiological parameters determined based on detection of tachyarrhythmia include an extent, e.g., frequency and/or duration during a time period, of AF or other tachyarrhythmias.

Processing circuitry 50 may also determine other physiological parameter values that can be used to determine probability of a health event based on the cardiac EGM and detection of depolarizations therein. As examples, processing circuitry 50 may determine one or more heart rate values, such as night heart rate values, one or more heart rate variability values. As other examples, processing circuitry 50 may determine magnitudes of or intervals between features within the cardiac EGM, such as depolarization amplitudes, depolarization widths, or intervals between depolarizations and repolarizations.

In some examples, sensors 62 include one or more accelerometers or other sensors configured to generate signals that indicate motion and orientation of patient 4, e.g., that indicate activity level or posture of the patient. In some examples, processing circuitry 50 processes such signals to determine values of one or more physiological parameters that can be used to determine probability of a health event. For example, processing circuitry 50 may quantify duration, frequency, and/or intensity of activity and/or posture changes, e.g., daily or during some other period. In some examples, processing circuitry 50 may determine an amount of time patient spends inactive, e.g., sleeping, but not in a supine posture based on such signals.

Sensing circuitry 52 includes impedance measurement circuitry 60. Processing circuitry 50 may control impedance circuitry 60 to periodically measure an electrical parameter to determine an impedance, such as a subcutaneous impedance indicative of fluid found in interstitium 28. For a subcutaneous impedance measurement, processing circuitry 50 may control impedance measurement circuitry 60 to deliver an electrical signal between selected electrodes 16 and measure a current or voltage amplitude of the signal. Processing circuitry 50 may select any combination of electrodes 16, e.g., by using switching circuitry 58 and sensing circuitry 52. Impedance measurement circuitry 60 includes sample and hold circuitry or other suitable circuitry for measuring resulting current and/or voltage amplitudes. Processing circuitry 50 determines an impedance value from the amplitude value(s) received from impedance measurement circuitry 60.

Because either IMD 10 or external device 12 may be configured to include sensing circuitry 52, impedance measurement circuitry 60 may be implemented in one or more processors, such as processing circuitry 50 of IMD 10 or processing circuitry 80 of external device 12. Impedance measurement circuitry 60 is, in this example, shown in conjunction with sensing circuitry 52 of IMD 10. Impedance measurement circuitry 60 may be embodied as one or more hardware modules, software modules, firmware modules, or any combination thereof. Impedance measurement circuitry 60 may analyze impedance measurement data on a periodic basis to identify a decrease in subcutaneous impedance in patient 4 and alert patient 4 when the decrease indicates onset of a possible heart failure decompensation event.

In some examples, processing circuitry 50 may perform an impedance measurement by causing impedance measurement circuitry 60 (via switching circuitry 58) to deliver a voltage pulse between at least two electrodes 16 and examining resulting current amplitude value measured by impedance measurement circuitry 60. In some examples, switching circuitry 58 delivers signals that do deliver stimulation therapy to the heart of patient 4. In other examples, these signals may be delivered during a refractory period, in which case they may not stimulate the heart of patient 4.

In some examples, processing circuitry 50 may perform an impedance measurement by causing impedance measurement circuitry 60 (via switching circuitry 58) to deliver a current pulse across at least two selected electrodes 16. Impedance measurement circuitry 60 holds a measured voltage amplitude value. Processing circuitry 50 determines an impedance value based upon the amplitude of the current pulse and the amplitude of the resulting voltage that is measured by impedance measurement circuitry 60. IMD 10 may use defined or predetermined pulse amplitudes, widths, frequencies, or electrode polarities for the pulses delivered for these various impedance measurements. In some examples, the amplitudes and/or widths of the pulses may be sub-threshold, e.g., below a threshold necessary to capture or otherwise activate tissue, such as cardiac tissue, subcutaneous tissue, or muscle tissue. In some examples, IMB 10 may use an amplifier circuit according to certain techniques described in U.S. application Ser. No. 12/872,552 by Denison et al., entitled "CHOPPER-STABILIZED INSTRUMENTATION AMPLIFIER FOR IMPEDANCE MEASUREMENT," filed on Aug. 31, 2010, incorporated herein by reference in its entirety, to for physiological signal sensing, impedance sensing, telemetry, etc.

In certain cases, IMB 10 may measure subcutaneous impedance values that include both a resistive component and a reactive component (e.g., X, XL, XC), such as in an impedance triangle. In such cases, IMD 10 may measure subcutaneous impedance during delivery of a sinusoidal or other time varying signal by impedance measurement circuitry 60, for example. Thus, as used herein, the term "impedance" is used in a broad sense to indicate any collected, measured, and/or calculated value that may include one or both of resistive and reactive components. In some examples, subcutaneous tissue impedance parameters are derived from subcutaneous tissue impedance signals received from electrodes 16.

Sensing circuitry 52 may also provide one or more impedance signals to processing circuitry 50 for analysis, e.g., for analysis to determine respiration and impedance parameters, e.g., impedance scores. In some examples, processing circuitry 50 may store the impedance values, impedance score factors (e.g., fluid indices, average impedance values, reference impedance values, buffer values, etc.), and impedance scores in storage device 56. Processing circuitry 50 of IMD 10, and/or processing circuitry of another device that retrieves data from IMD 10, may analyze the impedance values to determine a diagnostic state of the subcutaneous tissue impedance parameter.

Communication circuitry 54 may include any suitable hardware, firmware, software or any combination thereof for communicating with another device, such as external device 12, another networked computing device, or another IMD or sensor. Under the control of processing circuitry 50, communication circuitry 54 may receive downlink telemetry from, as well as send uplink telemetry to external device 12 or another device with the aid of an internal or external antenna, e.g., antenna 26. In addition, processing circuitry 50 may communicate with a networked computing device via an external device (e.g., external device 12) and a computer network, such as the Medtronic CareLink® Network.

Antenna 26 and communication circuitry 54 may be configured to transmit and/or receive signals via inductive coupling, electromagnetic coupling, NFC technologies, RF communication, Bluetooth®, Wi-Fi™, or other proprietary or non-proprietary wireless communication schemes. In some examples, processing circuitry 50 may provide data to be uplinked to external device 12 via communication circuitry 54 and control signals using an address/data bus. In another example, communication circuitry 54 may provide received data to processing circuitry 50 via a multiplexer.

In some examples, processing circuitry 50 may send impedance data to external device 12 or data server(s) 94 via communication circuitry 54. For example, IMD 10 may send external device 12 or data server(s) 94 collected impedance measurements. External device 12 and/or data server(s) 94 may then analyze those impedance measurements.

In some examples, storage device 56 includes computer-readable instructions that, when executed by processing circuitry 50, cause IMD 10 and processing circuitry 50 to perform various functions attributed to IMD 10 and processing circuitry 50 herein. Storage device 56 may include any volatile, non-volatile, magnetic, optical, or electrical media. For example, storage device 56 may include random access memory (RAM), read-only memory (ROM), non-volatile RAM (NVRAM), electrically-erasable programmable ROM (EEPROM), erasable programmable ROM (EPROM), flash memory, or any other digital media. Storage device 56 may store, as examples, programmed values for one or more operational parameters of IMD 10 and/or data collected by IMD 10 for transmission to another device using communication circuitry 54. Data stored by storage device 56 and transmitted by communication circuitry 54 to one or more other devices may include impedance values and/or digitized cardiac EGMs, as examples.

In some examples, processing circuitry, e.g., processing circuitry 50 of IMD 10, processing circuitry 80 of external device 12, or processing circuitry 98 of data server(s) 94, may determine RRs or other respiration parameters based on analysis of impedance values determined as described herein but, in some cases, sampled at a higher rate than for detecting changes in the fluid status of patient 4. For example, processing circuitry 50 (or processing circuitry of another device) may employ any of a variety of techniques to detect the frequency, period between, or magnitude of fluctuations in the impedance values associated with respiration of patient 4. In some examples, processing circuitry 50 may control impedance measurements for determining respiration parameters to occur when certain conditions are satisfied, e.g., time of day, such as night, or patient activity level or posture.

In some examples, processing circuitry, e.g., processing circuitry 50 of IMD 10, processing circuitry 80 of external device 12, or processing circuitry 98 of data server(s) 94, may determine an impedance score based on triggering events that indicate a subcutaneous tissue impedance event of patient 4. For example, processing circuitry 98 may increment the impedance score by a first value in response to a first group of one or more triggering events. In some examples, processing circuitry 98 may increment the impedance score by a second value in response to a second group of one or more triggering events. The first value, in some examples, may increment the impedance score by one point, whereas the second value, in some examples, may increment the impedance score by two points. Other point values may be used that are greater than or less than the first value or the second value. In some examples, processing circuitry 98 may detect multiple triggering events during a single iteration of the scoring cycle, in which case a sum of values may be applied to the impedance score. For example, processing circuitry 98 may increment the impedance score by four points when processing circuitry 98 determines that two triggering events are present, one triggering event corresponding to a two-point incremental value and where another triggering event also corresponds to a two-point incremental value. In some examples, processing circuitry 98 may determine a total impedance score between a value of 0 on the low end and 7 on the high end, as discussed herein.

In some examples, processing circuitry, e.g., processing circuitry 50 of IMD 10, processing circuitry 80 of external device 12, or processing circuitry 98 of data server(s) 94, may determine a diagnostic state based on the impedance score. For example, processing circuitry 98 may periodically compare the impedance score to one or more risk thresholds. For example, processing circuitry 98 may perform a comparison of the impedance score to the risk thresholds at a same time each day (e.g., at the end of the day). In some examples, processing circuitry 98 may determine the diagnostic state at multiple intervals each day. In yet another example, processing circuitry 98 may determine the diagnostic state at longer intervals, such as once a week or once every two weeks.

In some examples, processing circuitry 98 may determine a diagnostic state as a heart failure risk status. The risk status may be determined as low, medium, high, etc. In some examples, processing circuitry 98 may use a different number of risk categories, such as including a category for very high risk in some instances or very low risk. In addition, processing circuitry 98 may not include certain categories, such as the medium risk category, and instead only monitor low and high-risk categories. In some examples, processing circuitry 98 may compare the impedance score to risk thresholds to determine a diagnostic state for the subcutaneous tissue impedance parameter.

In a non-limiting example, processing circuitry 98 may determine diagnostic states for the subcutaneous tissue impedance parameter as follows: low risk if the impedance score is 0, medium risk if the impedance score is greater than or equal to 1 but less than or equal to 6, and high if the impedance score is greater than or equal to 7. Risk thresholds may be set (e.g., programmably by a user) based on optimization considerations and may be based on the specific values used to determine fluid index values.

In some examples, processing circuitry, e.g., processing circuitry 50 of IMD 10, processing circuitry 80 of external device 12, or processing circuitry 98 of data server(s) 94, may determine satisfaction of at least one of: a scoring threshold and an impedance threshold, with respect to one or more time windows. For example, processing circuitry 98 modify the impedance score in response to the one or more fluid index values satisfying one or more scoring thresholds for at least one of: a predetermined amount of time and a predetermined number of times (e.g., number of days, etc.). In an illustrative example, processing circuitry 98 may increment the impedance score by a point value (e.g., a 1 point value) in response to the following example conditions (e.g., scoring thresholds) being satisfied with respect to the first time period: (1) the fluid index values in the last 30 days have been greater than or equal to the adaptive threshold (multiplied by 0.6) for one or more days; (2) the fluid index values in the last 30 days have been greater than or equal to the adaptive threshold (multiplied by 1.7) for one or more days; or (3) the fluid index values in the last 30 days have been greater than or equal to the adaptive threshold (multiplied by 3.2) for one or more days. In this example, processing circuitry 98 determined the weighting factors as 0.6, 1.7, and 3.2. In this example, the first time period is the last 30 days. However, as discussed herein, the time periods and the weighting factors may vary depending on specifics related to patient 4, for example.

In another example, processing circuitry 98 may also increment the impedance score by a point value of greater than one (e.g., two points) in response to the average impedance satisfying an impedance value threshold and the fluid index satisfying scoring thresholds. In some examples, processing circuitry 98 may modify the impedance score in response to the average impedance value satisfying an impedance value threshold. The impedance value threshold may, in some examples, be less than or equal to approximately 600 ohms or another comparable ohm value.

For example, processing circuitry 98 may increment the impedance score by two points in response to the following example conditions (e.g., scoring thresholds and impedance value thresholds) being met with respect to the first time period: (1) the fluid index values in the last 30 days have been greater than or equal to the adaptive threshold (multiplied by 1.5) for 24 or more days; or (2) the average impedance in the last 30 days has been less than or equal to approximately 600 ohms. For the first condition, the 24 or more days may be consecutive days or instead may be a cumulative 24 days. For the average impedance, the average impedance in the last 30 days may refer to a set of daily average impedances in the last 30 days. In some examples, the average impedance in the last 30 days may refer to a single average of the impedance values measured over time. In another example, the average impedance may refer to a single average of the daily average impedance values determined over time.

In some examples, processing circuitry 98 may determine anew or modify an impedance score when the fluid index values during the second time period satisfy the adaptive threshold multiplied by the corresponding weighting factors. In addition, processing circuitry 98 may determine anew or modify an impedance score when the average impedance satisfies an impedance threshold during the second time period.

In an illustrative example, processing circuitry 98 may increment the impedance score by a point value equal to one in response to the following example conditions being satisfied with respect to the second time period: (1) the fluid index values in the last seven days have been greater than or equal to the adaptive threshold (multiplied by 0.6) for one or more days; (2) the fluid index values in the last seven days have been greater than or equal to the adaptive threshold (multiplied by 1.7) for one or more days; or (3) the fluid index values in the last seven days have been greater than or equal to the adaptive threshold (multiplied by 1.5) for seven or more days. In this example, IMD 10 determined the weighting factors as 0.6, 1.7, and 1.5. In this example, the second time period is the last seven days. However, as discussed herein, the time periods and the weighting factors may vary depending on specifics related to patient 4, for example. In addition, for the last condition, the 7 or more days may be consecutive days or instead may be a cumulative 7 days.

In another example, IMD 10 may also increment the impedance score by a point value of greater than one (e.g., two points) in response to other example conditions being met with respect to the second time period: (1) the fluid index values in the last seven days have been greater than or equal to the adaptive threshold (multiplied by 3.2) for one or more days; or (2) the average impedance in the last seven days has been less than or equal to approximately 600 ohms. For the average impedance, the average impedance in the last 7 days may refer to a set of daily average impedances in the last 7 days. In some examples, the average impedance in the last 7 days may refer to a single average of the impedance values measured over time. In another example, the average impedance may refer to a single average of the daily average impedance values determined over time.

In some examples, where overlaps exist between conditions, only the higher point value would be added to the impedance score so as to avoid any compounding affects to the modification of the impedance score. In keeping with the example described above, where two conditions are met (e.g., average impedance in last 7 days and in the last 30 days has been greater than or equal to approximately 600 ohms), the impedance score may only increment by two and not by four. In other examples, where two conditions are met (e.g., average impedance in last 7 days and in the last 30 days has been greater than or equal to approximately 600 ohms), IMD 10 may increment the impedance score based on both conditions being satisfied. The impedance score may be then be used to determine a diagnostic state of the subcutaneous tissue impedance physiological parameter to serve as one of evidence nodes 8.

As noted before with reference to FIGS. 4 and 5, the above techniques of determining an impedance score may also be performed on a periodic basis. For example, the impedance scores may be determined according to a resolution parameter setting of processing circuitry 50 (e.g., the resolution parameter used to signal a frequency at which electrodes 16 should probe for impedance measurements). In other examples, the impedance score may be calculated irrespective of the resolution parameter, which, for example, may apply to the fluid index determination and/or the reference impedance value determination, but not the impedance score determination. For instance, processing circuitry 50 may calculate the impedance scores at several time intervals each day (e.g., once in the morning, once in the afternoon, once in the evening, once after meals, etc.). In some examples, processing circuitry 50 may calculate the impedance score once a day, each week, every two weeks, each month, etc. In some examples, processing circuitry 50 may also calculate the impedance score in response to a user command (e.g., from a physician, from a user interface) or in response to a satisfaction of another condition (e.g., based on activity level or other physiological parameters). For example, processing circuitry 50 may determine impedance score on a per measurement basis, such as on a per fluid index determination basis or on a per impedance measurement basis. A person of skill in the art should appreciate that various periods may exist for when IMD 10, data server(s) 94, or external device 12 may transmit impedance scores, receive impedance scores, receive fluid index values, and/or otherwise, calculate impedance scores for subsequent analysis.

FIG. 9 is a conceptual side-view diagram illustrating an example configuration of an IMB, such as IMD 10 described with reference to FIGS. 7 and 8. The conceptual side-view diagram illustrates a muscle layer 20 and a skin layer 18 (e.g., dermis layer, epidermis layer). The region between muscle layer 20 and skin layer 18 includes subcutaneous space 22. Subcutaneous space includes blood vessels 24, such as capillaries, arteries, or veins, and interstitial fluid in the interstitium 28 of subcutaneous space 22. Subcutaneous space 22 has interstitial fluid that is commonly found between skin 18 and muscle layer 20. Subcutaneous space 22 may include interstitial fluid that surrounds blood vessels 24. For example, interstitial fluid surrounds capillaries and allows the passing of capillary elements (e.g., nutrients) between the different layers of a body through interstitium 28.

In the example shown in FIG. 9, IMD 10 may include a leadless, subcutaneously implantable monitoring device having a housing 15 and an insulative cover 76. Electrodes 16 may be formed or placed on an outer surface of cover 76. Although the illustrated example includes three electrodes 16, IMDs including or coupled to more or less than three electrodes 16 may implement the techniques of this disclosure in some examples. In some examples, electrodes 16 may be disposed all within a single layer, such as subcutaneous space 22 and contact interstitial fluid in subcutaneous space 22. In some examples, at least one of electrodes 16 of IMD 10 may disposed within another layer, such as muscle layer 20 or skin layer 18. In other examples, electrodes 16 may be disposed all within a single layer, such as subcutaneous space 22. In any event, at least one of electrodes 16 will contact interstitial fluid in subcutaneous space 22, whereas other electrodes 16 may not contact interstitial fluid. In other examples, each of electrodes 16 or at least two of electrodes 16 will contact interstitial fluid in subcutaneous space 22. In addition, at least two of the electrodes 16 may be positioned approximately 3 cm-5 cm apart, such as at 4 cm apart. In another example, some or all of electrodes 16 may be positioned closer or farther away than 4 cm.

Circuitries 50-62 may be formed or placed on an inner surface of cover 76, or within housing 15. In the illustrated example, antenna 26 is formed or placed on the inner surface of cover 76, but may be formed or placed on the outer surface in some examples. In some examples, one or more of sensors 62 may be formed or placed on the outer surface of cover 76. In some examples, insulative cover 76 may be positioned over an open housing 15 such that housing 15 and cover 76 enclose antenna 26 and circuitries 50-62, and protect antenna 26 and circuitries from fluids such as interstitial fluids or other bodily fluids.

One or more of antenna 26 or circuitries 50-62 may be formed on the inner side of insulative cover 76, such as by using flip-chip technology. Insulative cover 76 may be flipped onto a housing 15. When flipped and placed onto housing 15, the components of IMD 10 formed on the inner side of insulative cover 76 may be positioned in a gap 78 defined by housing 15. Electrodes 16 may be electrically connected to switching circuitry 58 through one or more vias (not shown) formed through insulative cover 76. Insulative cover 76 may be formed of sapphire (i.e., corundum), glass, parylene, and/or any other suitable insulating material.

Housing 15 may be formed from titanium or any other suitable material (e.g., a biocompatible material). Electrodes 16 may be formed from any of stainless steel, titanium, platinum, iridium, or alloys thereof. In addition, electrodes 16 may be coated with a material such as titanium nitride or fractal titanium nitride, although other suitable materials and coatings for such electrodes may be used.

Figure 10:
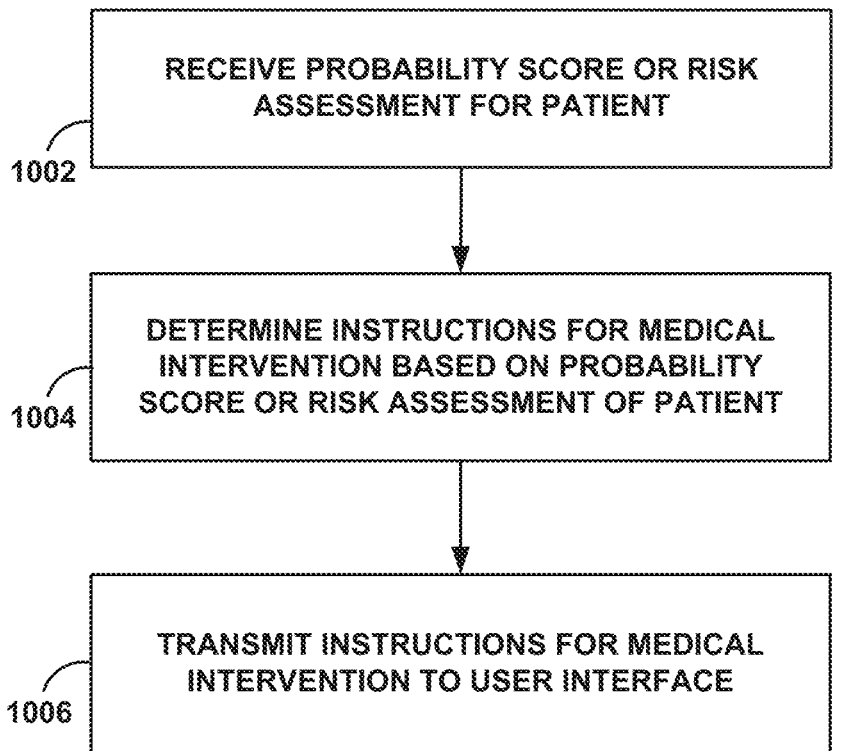
FIG. 10 is a flow diagram illustrating an example method that may be performed by one or both the medical device(s) and external device shown in FIG. 2 to provide an alert to the patient with respect to a health status of the patient, in accordance with one or more techniques disclosed herein.

Turning now to FIG. 10, data server(s) 94 may determine or receive the probability score or risk assessment for patient 4 from probability model 19 (1002). In some examples, the probability score may include a discrete risk categorization. For example, processing circuitry 98 may compare the probability score to at least one risk threshold. In some examples, processing circuitry 98 may perform such comparisons on a daily basis, weekly basis, monthly basis, etc. with or without real-time alerts and/or notifications. The risk thresholds may include discrete risk categorizations, such as above 20%=high risk, above 5%=medium risk and below 5%=low risk. Thus, processing circuitry 98 may determine, based on the comparison of the probability score to at least one risk threshold, a discrete risk categorization (e.g., high risk) from a plurality of discrete risk categorizations. As such, a risk assessment includes either the probability score or the risk categorization based on a risk threshold determination.

In some examples, data server(s) 94 may receive the probability score or risk assessment of patient 4 (1002). In some examples, data server(s) 94 may determine the probability score (>20%) or risk assessment (high risk). Data server(s) 94 may determine instructions for medical intervention based on the probability score or risk assessment of patient 4 (1004). For example, if the probability score is greater than a high-risk threshold, data server(s) 94 may determine instructions for medical intervention based on the high-risk determination. In other examples, data server(s) 94 may determine different instructions for different risk levels or categories. For example, data server(s) 94 may determine a first set of instructions for a high-risk patient and a second set of instructions for a medium-risk patient. In some examples, data server(s) 94 may not determine any instructions for a low risk patient (e.g., probability score less than 20%). In some examples, data server(s) 94 may generate an alert notification or sound an audible or tactile alarm alerting of the high-risk determination. In one example, the alert may include text or graphics information that communicates the probability score to an interested party. In addition, data server(s) 94 may provide information regarding the risk determination, such as a summary or detailed report of the alert. In a non-limiting example, the information may state that processing circuitry 98 determined high fluid based on impedance scores, high RR, and new onset AF, but that NHR and HRV was indicated as being normal, with activity being in the OK range. In some examples, external device 12 may provide a visual light indication, such as emitting a red light for high risk or a yellow light for medium risk. The alert may indicate a possible or predicted heart failure decompensation event that is likely to occur within a predetermined period of time.

In general, one cause of HF hospitalization (HFH) involves volume overload in which the body of a patient retains an excess amount of fluid. In such instances, the primary HF management strategy is to control excess fluid volume using diuretic and/or vasodilator or nitrate therapy. Further, ACE-Inhibitors, which control blood pressure, and β-blockers, which control heart rate, may reduce mortality in HF patients. As such, posterior probability 25 may indicate how much therapy should be administered. For example, a medical device 17 may be configured to deliver a therapy and/or data server(s) 94 may be configured to provide a therapy instruction based on a posterior probability 25 that satisfies a particular risk threshold. Posterior probability 25 may include a percentage (e.g., 20%) or a decimal value (0.2) or a probability score (e.g., high, medium, low; intervention, light intervention, no intervention; etc.) determined from the percentage or decimal value. In some examples, posterior probability 25 may include a probability distribution, such as a Gaussian distribution, where processing circuitry 98 may determine a likelihood percentage, decimal value, or probability score, from the probability distribution.

In some examples, data server(s) 94 may transmit the instructions for medical intervention to a user interface (1006). In other examples, data server(s) 94 may transmit the instructions to a device of a caretaker, such as a pager. In examples where IMD 10 generates the instructions based on a probability score, processing circuitry 50 may transmit the instructions for medical intervention to a user interface. The instructions may include the probability score or may include the diagnostic states that factored into determining the probability score. In some instances, a physician or caretaker may not need to know the diagnostic states and may only want to receive the probability score determined from the diagnostic states or vice versa. In any event, processing circuitry may compare the probability score against at least one risk threshold on a periodic or semi-periodic basis. In some examples, medical intervention techniques may be assessed or processing circuitry, e.g., processing circuitry 50 of IMD 10, processing circuitry 80 of external device 12, or processing circuitry 98 of data server(s) 94, may provide adjustments to patient treatment in accordance with certain techniques described in commonly-assigned U.S. application Ser. No. 15/402,839 by Sharma et al., entitled "MEDICAL SYSTEM FOR SEAMLESS THERAPY ADJUSTMENT," filed on Jan. 10, 2017, incorporated herein by reference in its entirety.

Various examples have been described. However, one of ordinary skill in the art will appreciate that various modifications may be made to the described examples without departing from the scope of the claims. For example, additional physiological parameters may be considered to determine probability scores of worsening heart failure or other adverse health events. Examples of other physiological parameters are described in commonly-assigned U.S. application Ser. Nos. 12/184,149 and 12/184,003 by Sarkar et al., entitled "USING MULTIPLE DIAGNOSTIC PARAMETERS FOR PREDICTING HEART FAILURE EVENTS," and "DETECTING WORSENING HEART FAILURE BASED ON IMPEDANCE MEASUREMENTS," both filed on Jul. 31, 2008, both of which are incorporated herein by reference in their entirety.

Illustrative examples of this disclosure include:

Example 1: A system for monitoring health events, the system including: an implantable medical device (IMD) including a plurality of electrodes and configured for subcutaneous implantation in a patient, wherein the IMD is configured to determine one or more subcutaneous tissue impedance measurements via the electrodes; and processing circuitry coupled to the one or more storage devices, and configured to: determine a respective one or more values for each of a plurality of physiological parameters, the plurality of physiological parameters including one or more subcutaneous tissue impedance parameters determined from the one or more subcutaneous tissue impedance measurements; identify a diagnostic state for each of the physiological parameters based on the respective values, the diagnostic states defining a plurality of evidence nodes for a probability model; and determine, from the probability model, a probability score indicating a likelihood that the patient (a) is experiencing an adverse health event or (b) is likely to experience the adverse health event within a predetermined amount of time.

Example 2: A system according to Example 1, wherein the processing circuitry is further configured to: select, from at least three potential diagnostic states, a single diagnostic state for each evidence node.

Example 3: A system according to any one of Examples 1 or 2, wherein the predetermined amount of time is at least approximately 7 days relative to when the probability score is determined.

Example 4: A system according to any one or more of Examples 1 through 3, wherein the determined values of the physiological parameters correspond to a preceding timeframe relative to when the probability score is determined.

Example 5: A system according to Example 4, wherein the preceding timeframe is approximately 30 days relative to when the probability score is determined.

Example 6: A system according to any one of Examples 4 or 5, wherein the predetermined amount of time and the preceding timeframe include a same amount of time relative to when the probability score is determined.

Example 7: A system according to any one or more of Examples 1 through 6, wherein the one or more subcutaneous tissue impedance parameters include a subcutaneous tissue impedance score.

Example 8: A system according to any one or more of Examples 1 through 7, wherein the physiological parameters include values corresponding to at least one of: heart rate variability (HRV), night heart rate (NHR), patient activity (ACT), atrial fibrillation (AF), R-wave amplitude, heart sounds, or ventricular rate.

Example 9: A system according to any one or more of Examples 1 through 8, wherein the physiological parameters include values corresponding to at least one of: respiratory effort, temperature, short term HRV, chronotropic incompetence, B-type natriuretic peptide (BNP), renal dysfunction, blood pressure, body posture, posture change, posture-change count, cough parameters, day activity, night activity, stepping-out-of-bed count, or accelerometer data values.

Example 10: A system according to any one or more of Examples 1 through 9, wherein the physiological parameters include at least one value corresponding to a respiration rate (RR) of the patient.

Example 11: A system according to Example 10, wherein the processing circuitry is configured to: identify, based on the one or more subcutaneous tissue impedance measurements, a periodic variation in subcutaneous tissue impedance; and determine, based on the periodic variation in subcutaneous tissue impedance, the RR of the patient.

Example 12: A system according to any one or more of Examples 1 through 11, wherein the processing circuitry is configured to: identify a plurality of physiological parameter features based on the respective one or more values for each physiological parameter, wherein the features are configured to, upon analysis, yield a same number of potential diagnostic states for each physiological parameter; and identify, from the potential diagnostic states, the diagnostic state for each of the physiological parameters.

Example 13: A system according to any one or more of Examples 1 through 12, wherein the processing circuitry is configured to: identify, from the respective one or more values for each physiological parameter, a plurality of physiological parameter features that encode amplitude, out-of-normal range values, and temporal changes; and identify the evidence nodes based at least in part on the plurality of physiological parameter features.

Example 14: A system according to any one or more of Examples 1 through 13, wherein the probability model represents a Bayesian Network (e.g., a BBN, etc.) including at least two child nodes and a parent node.

Example 15: A system according to any one or more of Examples 1 through 14, wherein the processing circuitry is configured to: determine an input to a first child node of the plurality of evidence nodes based on the respective one or more values of the one or more subcutaneous tissue impedance parameters; and determine an input to a second child node of the plurality of evidence nodes based on a combination of one or more values indicating an extent of atrial fibrillation (AF) in the patient during a time period and one or more values indicating a ventricular rate during the time period.

Example 16: A system according to any one or more of Examples 1 through 15, wherein the processing circuitry is further configured to: determine, from the plurality of physiological parameters, at least one of: a prior probability value or a conditional likelihood parameter; include at least one of: the prior probability value or the conditional likelihood parameter, as input to the probability model when determining the probability score.

Example 17: A system according to Example 16, wherein the probability model is expressed as:

$$P(d, e_1, \ldots , e_N) = P(d) \prod_{i=1}^{N} P(e_i \mid d),$$

wherein P(d) represents the prior probability value, P(e$_i$|d) represents the conditional likelihood parameter, d represents a parent node, and e$_1$-e$_N$ represent the evidence nodes.

Example 18: A system according to any one or more of Examples 1 through 17, wherein the probability score includes at least one of: a joint probability distribution or a discrete risk categorization.

Example 19: A system according to any one or more of Examples 1 through 18, wherein the probability score indicates the likelihood of a heart failure worsening event occurring within the predetermined timeframe.

Example 20: A system according to any one or more of Examples 1 through 19, wherein the processing circuitry is further configured to: generate an alert in response to the probability score satisfying a risk threshold.

Example 21: A system according to any one or more of Examples 1 through 20, wherein the processing circuitry is further configured to: compare the probability score to at least one risk threshold; and determine one of a plurality of discrete risk categorizations based on the comparison.

Example 22: A system according to any one or more of Examples 1 through 21, wherein the processing circuitry is further configured to: transmit, to another device, the probability score.

Example 23: A system according to any one or more of Examples 1 through 22, wherein the processing circuitry is further configured to: receive, from another device, the plurality of physiological parameters.

Example 24: A system according to any one or more of Examples 1 through 23, wherein the processing circuitry is further configured to: receive, from another device, the one or more subcutaneous tissue impedance parameters.

Example 25: A system according to any one or more of Examples 1 through 24, wherein the processing circuitry is further configured to: determine, for each of the plurality of physiological parameters, the respective one or more values determined at various frequencies; determine the diagnostic states using the respective one or more values; and store, to a memory device, at least one of: the respective one or more values or the probability score.

Example 26: A system according to any one or more of Examples 1 through 25, wherein the processing circuitry is further configured to: identify an occurrence of missing data, the missing data corresponding to a particular physiological parameter; determine an extent to which the data for the physiological parameter is missing; and determine whether to use the physiological parameter when determining the probability score based on the extent to which the data is missing.

Example 27: A method including: determining a respective one or more values for each of a plurality of physiological parameters, the plurality of physiological parameters including one or more subcutaneous tissue impedance parameters determined from one or more subcutaneous tissue impedance measurements; identifying a diagnostic state for each of the physiological parameters based on the respective values, the diagnostic states defining a plurality of evidence nodes for a probability model; and determining, from the probability model, a probability score indicating a likelihood that the patient (a) is experiencing an adverse health event or (b) is likely to experience the adverse health event within a predetermined amount of time.

Example 28: A method according to Example 27, further including: selecting, from at least three potential diagnostic states, a single diagnostic state for each evidence node.

Example 29: A method according to any one of Examples 27 or 28, wherein the predetermined amount of time is at least approximately 7 days relative to when the probability score is determined.

Example 30: A method according to any one or more of Examples 27 through 29, wherein the determined values of the physiological parameters correspond to a preceding timeframe relative to when the probability score is determined.

Example 31: A method according to Example 30, wherein the preceding timeframe is approximately 30 days relative to when the probability score is determined.

Example 32: A method according to any one of Examples 30 or 31, wherein the predetermined amount of time and the preceding timeframe include a same amount of time relative to when the probability score is determined.

Example 33: A method according to any one or more of Examples 27 through 32, wherein the one or more subcutaneous tissue impedance parameters include a subcutaneous tissue impedance score.

Example 34: A method according to any one or more Examples 27 through 33, wherein the physiological parameters include values corresponding to at least one of: heart rate variability (HRV), night heart rate (NHR), patient activity (ACT), atrial fibrillation (AF), heart sounds, or ventricular rate.

Example 35: A method according to any one or more of Examples 27 through 34, wherein the physiological parameters include values corresponding to at least one of: respiratory effort, temperature, short term HRV, R-wave amplitude, chronotropic incompetence, B-type natriuretic peptide (BNP), renal dysfunction, blood pressure, body posture, posture change, posture-change count, cough parameters, day activity, night activity, stepping-out-of-bed count, or accelerometer data values.

Example 36: A method according to any one or more of Examples 27 through 35, wherein the physiological parameters include at least one value corresponding to a respiration rate (RR) of the patient.

Example 37: A method according to Example 36, further including: identifying, based on the one or more subcutaneous tissue impedance measurements, a periodic variation in subcutaneous tissue impedance; and determining, based on the periodic variation in subcutaneous tissue impedance, the RR of the patient.

Example 38: A method according to any one or more of Examples 27 through 37, further including: identifying a plurality of physiological parameter features based on the respective one or more values for each physiological parameter, wherein the features are configured to, upon analysis, yield a same number of potential diagnostic states for each physiological parameter; and identifying, from the potential diagnostic states, the diagnostic state for each of the physiological parameters.

Example 39: A method according to any one or more of Examples 27 through 38, further including: identifying, from the respective one or more values for each physiological parameter, a plurality of physiological parameter features that encode amplitude, out-of-normal range values, and temporal changes; and identifying the evidence nodes based at least in part on the plurality of physiological parameter features.

Example 40: A method according to any one or more of Examples 27 through 39, wherein the probability model represents a Bayesian Network (e.g., a BBN, etc.) including at least two child nodes and a parent node.

Example 41: A method according to any one or more of Examples 27 through 40, further including: determining an input to a first child node of the plurality of evidence nodes based on the respective one or more values of the one or more subcutaneous tissue impedance parameters; and determining an input to a second child node of the plurality of evidence nodes based on a combination of one or more values indicating an extent of atrial fibrillation (AF) in the patient during a time period and one or more values indicating a ventricular rate during the time period.

Example 42: A method according to any one or more of Examples 27 through 41, further including: determining, from the plurality of physiological parameters, at least one of: a prior probability value or a conditional likelihood parameter; and including at least one of: the prior probability value or the conditional likelihood parameter, as input to the probability model when determining the probability score.

Example 43: A method according to Example 42, wherein the probability model is expressed as:

$$P(d, e_1, \ldots, e_N) = P(d) \prod_{i=1}^{N} P(e_i \mid d),$$

wherein P(d) represents the prior probability value, $P(e_i|d)$ represents the conditional likelihood parameter, d represents a parent node, and $e_1$-$e_N$ represent the evidence nodes.

Example 44: A method according to any one or more of Examples 27 through 43, wherein the probability score includes at least one of: a joint probability distribution or a discrete risk categorization.

Example 45: A method according to any one or more of Examples 27 through 44, wherein the probability score indicates the likelihood of a heart failure worsening event occurring within the predetermined timeframe.

Example 46: A method according to any one or more of Examples 27 through 45, wherein the processing circuitry is further configured to: generate an alert in response to the probability score satisfying a risk threshold.

Example 47: A method according to any one or more of Examples 27 through 46, further including: comparing the probability score to at least one risk threshold; and determining one of a plurality of discrete risk categorizations based on the comparison.

Example 48: A method according to any one or more of Examples 27 through 47, further including: transmitting, to another device, the probability score.

Example 49: A method according to any one or more of Examples 27 through 48, further including: receiving, from another device, the plurality of physiological parameters.

Example 50: A method according to any one or more of Examples 27 through 49, further including: receiving, from another device, the one or more subcutaneous tissue impedance parameters.

Example 51: A method according to any one or more of Examples 27 through 50, further including: determining, for each of the plurality of physiological parameters, the respective one or more values determined at various frequencies; determining the diagnostic states using the respective one or more values; and storing, to a memory device, at least one of: the respective one or more values or the probability score.

Example 52: A non-transitory computer-readable storage medium having stored thereon instructions that, when executed, cause one or more processors to at least: determine a respective one or more values for each of a plurality of physiological parameters, the plurality of physiological parameters including one or more subcutaneous tissue impedance parameters identified from one or more subcutaneous tissue impedance measurements; identify a diagnostic state for each of the physiological parameters based on the respective values, the diagnostic states defining a plurality of evidence nodes for a probability model; and determine, from the probability model, a probability score indicating a likelihood that the patient (a) is experiencing an adverse health event or (b) is likely to experience the adverse health event within a predetermined amount of time.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry (as in QRS complex), as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, ROM, NVRAM, DRAM, SRAM, Flash memory, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD or other medical device, an external programmer, a combination of a medical device and external programmer, an integrated circuit (IC) or a set of ICs, and/or discrete electrical circuitry, residing in a medical device and/or external programmer.

Furthermore, although described primarily with reference to examples that provide a probability score to indicate worsening heart failure, other examples may additionally or alternatively automatically modify a therapy in response to the probability score exceeding a predetermined threshold. The therapy may be, as examples, a substance delivered by an implantable pump, cardiac resynchronization therapy, refractory period stimulation, or cardiac potentiation therapy. These and other examples are within the scope of the following claims.

The invention claimed is:

1. A system comprising:
an implantable medical device (IMD) comprising a housing and a plurality of electrodes on the housing, wherein the TNID, the housing, and the plurality of electrodes are configured for subcutaneous implantation in a patient, wherein the plurality of electrodes are positioned within 5 centimeters (cm) apart on the housing and the IMD is configured to determine one or more subcutaneous tissue impedance measurements of interstitial fluid in an interstitium of a subcutaneous space of the patient measured using only the electrodes on the housing; and processing circuitry coupled to one or more storage devices, and configured to:
receive the one or more subcutaneous tissue impedance measurement of the interstitial fluid determined via the electrodes;
determine a respective one or more values for each of a plurality of physiological parameters, the plurality of physiological parameters including:
a first period of time subcutaneous tissue impedance parameter determined from the one or more subcutaneous tissue impedance measurements of the interstitial fluid over the first period of time, and
a second period of time subcutaneous tissue impedance parameter determined from the one or more subcutaneous tissue impedance measurements of the interstitial fluid over the second period of time, the second period of time being longer in duration than the first period of time;
determine a diagnostic state for each of the physiological parameters based on the respective values, the diagnostic states defining a plurality of evidence nodes for a probability model; and
apply the plurality of evidence nodes to the probability model to determine a probability score indicating a likelihood that the patient (a) is experiencing an adverse health event or (b) is likely to experience the adverse health event within a predetermined amount of time, wherein the first period of time is up to 7 days and the second period of time is up to 30 days.

2. The system of claim 1, wherein the determined values of the physiological parameters correspond to a preceding timeframe relative to when the probability score is determined.

3. The system of claim 1, wherein the physiological parameters include values corresponding to at least one of: heart rate variability (HRV), night heart rate (NHR), patient activity (ACT), atrial fibrillation (AF), R-wave amplitude, heart sounds, or ventricular rate.

4. The system of claim 1, wherein the processing circuitry is configured to:
determine, from the respective one or more values for each physiological parameter, a plurality of physiological parameter features that encode amplitude, out-of-normal range values, and temporal changes; and
determine the evidence nodes based at least in part on the plurality of physiological parameter features.

5. The system of claim 1, wherein the probability model is a Bayesian Network comprising at least two child nodes and a parent node.

6. The system of claim 1, wherein the processing circuitry is configured to:
determine an input to a first child node of the plurality of evidence nodes based on the respective one or more values of the first period of time subcutaneous tissue impedance parameter and the second period of time subcutaneous tissue impedance parameter; and
determine an input to a second child node of the plurality of evidence nodes based on a combination of one or more values indicating an extent of atrial fibrillation (AF) in the patient during a time period and one or more values indicating a ventricular rate during the time period.

7. The system of claim 1, wherein the processing circuitry is further configured to:
compare the probability score to at least one risk threshold; and
determine one of a plurality of discrete risk categorizations based on the comparison.

8. The system of claim 1, wherein the processing circuitry is further configured to:
determine an occurrence of missing data, the missing data corresponding to a particular physiological parameter;
determine an extent to which the data for the physiological parameter is missing; and
determine whether to use the physiological parameter when determining the probability score based on the extent to which the data is missing.

9. A method comprising:
obtaining, via a plurality of electrodes on a housing of an implantable medical device (IMD) implanted subcutaneously in a patient, one or more subcutaneous tissue impedance measurements of interstitial fluid in an interstitium of a subcutaneous space of the patient wherein the plurality of electrodes are positioned within 5 centimeters (cm) apart on the housing;
determining, by processing circuitry of a computing device, a respective one or more values for each of a plurality of physiological parameters, the plurality of physiological parameters including:
a first period of time subcutaneous tissue impedance parameter determined from the one or more subcutaneous tissue impedance measurements of interstitial fluid measured over the first period of time, and a second period of time subcutaneous tissue impedance parameter determined from the one or more subcutaneous tissue impedance measurements of the interstitial fluid measured over the second period of time, the first period of time is up to 7 days, and the second period of time is up to 30 days;

determining, by the processing circuitry, a diagnostic state for each of the physiological parameters based on the respective values, the diagnostic states defining a plurality of evidence nodes for a probability model; and applying, by the processing circuitry, the plurality of evidence nodes to the probability model to determine a probability score indicating a likelihood that the patient (a) is experiencing an adverse health event or (b) is likely to experience the adverse health event within a predetermined amount of time.

10. The method of claim 9, wherein the determined values of the physiological parameters correspond to a preceding timeframe relative to when the probability score is determined.

11. The method of claim 9, wherein the physiological parameters include values corresponding to at least one of: heart rate variability (HRV), night heart rate (NHR), patient activity (ACT), atrial fibrillation (AF), heart sounds, or ventricular rate.

12. The method of claim 9, further comprising:
determining, by the processing circuitry, based on the one or more subcutaneous tissue impedance measurements, a periodic variation in subcutaneous tissue impedance; and determining, by the processing circuitry, based on the periodic variation in subcutaneous tissue impedance, a parameter value for at least one of the physiological parameters.

13. The method of claim 9, further comprising:
determining, by the processing circuitry, a plurality of physiological parameter features based on the respective one or more values for each physiological parameter, wherein the features are configured to, upon analysis, yield a same number of potential diagnostic states for each physiological parameter; and determining, by the processing circuitry, from the potential diagnostic states, the diagnostic state for each of the physiological parameters.

14. The method of claim 9, wherein the probability model is a Bayesian Network comprising at least two child nodes and a parent node.

15. The method of claim 9, further comprising:
determining, by the processing circuitry, an input to a first child node of the plurality of evidence nodes based on the respective one or more values of the first period of time subcutaneous tissue impedance parameter and the second period of time subcutaneous tissue impedance parameter; and determining, by the processing circuitry, an input to a second child node of the plurality of evidence nodes based on a combination of one or more values indicating an extent of atrial fibrillation (AF) in the patient during a time period and one or more values indicating a ventricular rate during the time period.

16. The method of claim 9, further comprising:
comparing, by the processing circuitry, the probability score to at least one risk threshold; and determining, by the processing circuitry, one of a plurality of discrete risk categorizations based on the comparison.

17. The method of claim 9, further comprising:
determining, by the processing circuitry, for each of the plurality of physiological parameters, the respective one or more values determined at various frequencies;

determining, by the processing circuitry, the diagnostic states using the respective one or more values; and storing, by the processing circuitry, to a memory device, at least one of: the respective one or more values or the probability score.

18. A non-transitory computer-readable storage medium having stored thereon instructions that, when executed, cause one or more processors to at least:
obtain, via a plurality of electrodes on a housing of an implantable medical device (IMD) implanted subcutaneously in a patient, one or more subcutaneous tissue impedance measurements of interstitial fluid in an interstitium of a subcutaneous space of the patient, wherein the plurality of electrodes are positioned within 5 centimeters (cm) apart on the housing;

determine a respective one or more values for each of a plurality of physiological parameters, the plurality of physiological parameters including:
a first period of time subcutaneous tissue impedance parameter identified from the one or more subcutaneous tissue impedance measurements of interstitial fluid measured over the first period of time, and a second period of time subcutaneous tissue impedance parameter determined from the one or more subcutaneous tissue impedance measurements of the interstitial fluid measured over the second period of time, the first period of time is up to 7 days, and the second period of time is up to 30 days;

determine a diagnostic state for each of the physiological parameters based on the respective values, the diagnostic states defining a plurality of evidence nodes for a probability model; and apply the plurality of evidence nodes to the probability model to a probability score indicating a likelihood that the patient (a) is experiencing an adverse health event or (b) is likely to experience the adverse health event within a predetermined amount of time.

19. The system of claim 1, wherein the plurality of electrodes are positioned on the housing to face a skin layer of the patient when the IMD is subcutaneously implanted.

20. The system of claim 1, wherein at least two electrodes of the plurality of electrodes are separated by a fixed distance.

21. The system of claim 1, wherein the processing circuitry is configured to:
determine the probability score satisfies a health condition worsening threshold; and generate a remediation action in response to the determination that the probability score satisfies the health condition worsening threshold.

22. The system of claim 21, wherein the remediation action includes modifying a therapy.

23. The system of claim 1, wherein the processing circuitry is configured to:
perform the one or more subcutaneous tissue impedance measurement of the interstitial fluid by delivering an electrical signal between at least two electrodes of the plurality of electrodes, determining a value of a resulting current amplitude or a value of a resulting voltage amplitude, and determining the subcutaneous tissue impedance measurement based on at least one of the value of the resulting current amplitude or the value of the resulting voltage amplitude.

24. The system of claim 1, wherein the processing circuitry is configured to:

perform the one or more subcutaneous tissue impedance measurement of the interstitial fluid by at least one of:

delivering a voltage pulse between at least two electrodes of the plurality of electrodes, determining a resulting current amplitude value, and determining the subcutaneous tissue impedance measurement based on the resulting current amplitude value; or delivering a current pulse across at least two electrodes of the plurality of electrodes, determining an amplitude of a resulting voltage, and determining the subcutaneous tissue impedance measurement based on an amplitude of the current pulse and the amplitude of the resulting voltage.

25. The system of claim 1, wherein the first period of time is within the second period of time.

\* \* \* \* \*